US012678457B2

(12) United States Patent
Wu et al.

(10) Patent No.: US 12,678,457 B2
(45) Date of Patent: Jul. 14, 2026

(54) BLOOD-BRAIN BARRIER-PENETRATING NANOTHERANOSTICS FOR ACUTE AND CHRONIC NEURODEGENERATIVE DISEASES AND THE LIKE

(71) Applicant: THE GOVERNING COUNCIL OF THE UNIVERSITY OF TORONTO, Toronto (CA)

(72) Inventors: Xiaoyu Wu, Toronto (CA); Chunsheng He, Toronto (CA); Azhar Abbasi, Milton (CA); Taksim Ahmed, Toronto (CA); Jeffrey Henderson, Toronto (CA); Ping Cai, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 385 days.

(21) Appl. No.: 18/027,773

(22) PCT Filed: Sep. 29, 2021

(86) PCT No.: PCT/CA2021/051356
§ 371 (c)(1),
(2) Date: Mar. 22, 2023

(87) PCT Pub. No.: WO2022/067430
PCT Pub. Date: Apr. 7, 2022

(65) Prior Publication Data
US 2023/0330136 A1      Oct. 19, 2023

Related U.S. Application Data

(60) Provisional application No. 63/085,729, filed on Sep. 30, 2020.

(51) Int. Cl.
| | |
|---|---|
| *A61K 33/32* | (2006.01) |
| *A61K 9/00* | (2006.01) |
| *A61K 47/54* | (2017.01) |
| *A61K 47/68* | (2017.01) |
| *A61K 49/18* | (2006.01) |
| *A61P 25/28* | (2006.01) |
| *B82Y 5/00* | (2011.01) |
| *C07K 16/18* | (2006.01) |

(52) U.S. Cl.
CPC ............ *A61K 33/32* (2013.01); *A61K 9/0019* (2013.01); *A61K 47/543* (2017.08); *A61K 47/6843* (2017.08); *A61K 49/1875* (2013.01); *A61P 25/28* (2018.01); *B82Y 5/00* (2013.01); *C07K 16/18* (2013.01)

(58) Field of Classification Search
CPC .. A61K 33/32; A61K 47/6843; A61K 47/543; A61K 9/0019; A61K 49/1875; A61P 25/28; B82Y 5/00; C07K 16/18
See application file for complete search history.

(56) References Cited

U.S. PATENT DOCUMENTS

2015/0078995 A1 *  3/2015  Kandimalla ......... A61K 31/726
424/1.49

FOREIGN PATENT DOCUMENTS

| WO | 2009136763 | 11/2009 | |
| WO | WO-2009136763 A2 * | 11/2009 | ......... A61K 49/1857 |
| WO | 2016073348 | 5/2016 | |
| WO | WO-2016073348 A1 * | 5/2016 | ............ A61B 5/055 |
| WO | 2016090092 | 6/2016 | |
| WO | WO-2016191544 A1 * | 12/2016 | .......... A61K 31/573 |
| WO | 2021111364 | 10/2021 | |

OTHER PUBLICATIONS

Google Search; theranostic nanoparticles (accessed May 2025) (Year: 2025).*
Muthu et al.; Nanotheranostics—Application and Further Development of Nanomedicine Strategies for Advanced Theranostics; Ivyspring International Publisher; Theranostics 2014, vol. 4, Issue 6, 660-677 (Year: 2014).*
Li et al.; Functional Nanoparticles in Targeting Glioma Diagnosis and Therapies; American Scientific Publishers; Journal of Nanoscience and Nanotechnology vol. 14, 415-432, 2014 (Year: 2014).*
Yu et al.; H2O2-responsive theranostic nanomedicine; Elsevier; Chinese Chemical Letters 28 (2017) 1841-1850 (Year: 2017).*
Ahmad et al.; Nanotechnology Based Theranostic Approaches in Alzheimer's Disease Management: Current Status and Future Perspective; Bentham Science; Current Alzheimer Research, 2017, 14, 1-18 (Year: 2017).*
H.L. Wong, X.Y. Wu, R. Bendayan, Nanotechnological advances for the delivery of CNS therapeutics, Adv Drug Deliv Rev, 64 (2012) 686-700.
D. Mehta, R. Jackson, G. Paul, J. Shi, M. Sabbagh, Why do trials for Alzheimer's disease drugs keep failing? A discontinued drug perspective for 2010-2015, Expert Opin. Investig. Drugs, 26 (2017) 735-739.
K. Blennow, H. Zetterberg, The Past and the Future of Alzheimer's Disease Fluid Biomarkers, J. 30 Alzheimers Dis., 62 (2018) 1125-1140.
G.B. Frisoni, et al., Strategic roadmap for an early diagnosis of Alzheimer's disease based on biomarkers, Lancet Neurol., 16 (2017) 661-676.

(Continued)

*Primary Examiner* — Robert A Wax
*Assistant Examiner* — John W Lippert, III
(74) *Attorney, Agent, or Firm* — Eduardo Krupnik

(57) ABSTRACT

Brain-targeted (BT) and ROS-activable nanoconstructs (NC) comprising a metal oxide nanoparticle embedded in a matrix of lipid and a brain targeted polymer (BTP)/platform configured to facilitate blood brain barrier (BBB) penetration and accumulation in a disease area of the central nervous system (CNS), as well as compositions having the BT and ROS-activable NC and methods of using the BT and ROS-activable NC to treat and diagnose a CNS disease or condition.

23 Claims, 27 Drawing Sheets

(56) References Cited

OTHER PUBLICATIONS

K.A. Johnson, N.C. Fox, R.A. Sperling, W.E. Klunk, Brain imaging in Alzheimer disease, Cold Spring Harb. Perspect. Med., 2 (2012) a006213.

K.L. Viola, J. Sbarboro, R. Sureka, M. De, M.A. Bicca, J. Wang, S. Vasavada, S. Satpathy, S. Wu, H. 10 Joshi, P.T. Velasco, K. MacRenaris, E.A. Waters, C. Lu, J. Phan, P. Lacor, P. Prasad, V.P. Dravid, W.L. Klein, Towards non-invasive diagnostic imaging of early-stage Alzheimer's disease, Nat Nano, 10 (2015) 91-98.

H. Rusinek, S. De Santi, D. Frid, W.H. Tsui, C.Y. Tarshish, A. Convit, M.J. de Leon, Regional brain atrophy rate predicts future cognitive decline: 6-year longitudinal MR imaging study of normal aging, Radiology, 229 (2003) 691-696.

A. Weller, J.L. Barber, Ø.E. Olsen, Gadolinium and nephrogenic systemic fibrosis: an update, Pediatr. Nephrol., 29 (2014) 1927-1937.

J.A. Rees, G.J. Deblonde, D.D. An, C. Ansoborlo, S.S. Gauny, R.J. Abergel, Evaluating the potential of chelation therapy to prevent and treat gadolinium deposition from MRI contrast agents, Sci. Rep., 8 (2018) 4419.

W.A. Banks, From blood-brain barrier to blood-brain interface: new opportunities for CNS drug delivery, Nat Rev Drug Discov, 15 (2016) 275-292.

Y. Su, P.T. Chang, Acidic pH promotes the formation of toxic fibrils from beta-amyloid peptide, Brain Res., 893 (2001) 287-291.

D. Pan, S.D. Caruthers, A. Senpan, A.H. Schmieder, S.A. Wickline, G.M. Lanza, Revisiting an old friend: manganese-pased MRI contrast agents, Wiley Interdiscip Rev Nanomed Nanobiotechnol, 3 (2011) 162-173.

M.A. Chishti, et al., Early-onset amyloid deposition and cognitive 30 deficits in transgenic mice expressing a double mutant form of amyloid precursor protein 695, J. Biol. Chem., 276 (2001) 21562-21570.

Written Opinion of the International Searching Authority (Dec. 16, 2021), PCT/CA2021/051356, WO2022067430.

Li, M., et al., Functional Nanoparticles in Targeting Glioma Diagnosis and Therapies, Journal of Nanoscience and Nanotechnology, vol. 14, 415-432, 2014.

Ahmad, J., et al., Nanotechnology Based Theranostic Approaches in Alzheimer's Disease Management: Current Status and Future Perspective, Current Alzheimer Research, 2017, 14, 1-18.

Muthu, M., et al., Nanotheranostics—Application and Further Development of Nanomedicine Strategies for Advanced Theranostics, Theranostics 2014, vol. 4, Issue 6, 660-677.

Mukherjee, A., et al., Recent Advancements of Nanomedicine towards Antiangiogenic Therapy in Cancer, Int. J. Mol. Sci. 2020, 21, 455; doi:10.3390/ijms21020455.

Barbara, R., et al., Novel Curcumin loaded nanoparticles engineered for Blood-Brain Barrier crossing and able to disrupt Abeta aggregates, International Journal of Pharmaceutics 526 (2017) 413-424.

Siddhardha, B. and Parasuraman, P., Theranostics application of nanomedicine in cancer detection and treatment, Nanomaterials for Drug Delivery and Therapy; 2019; Chapter 03; p. 59-89.

Gordijo, C.R., et al., Design of Hybrid MnO2-Polymer-Lipid Nanoparticles with Tunable Oxygen Generation Rates and Tumor Accumulation for Cancer Treatment, Adv. Func. Mater 25 (2015) 1858-1872.

Shaw, L.M., et al., Biomarkers of neurodegeneration for diagnosis and monitoring therapeutics, Nat. Rev. Drug Discov., 6 (2007) 295-303. 5.

Feng, X., et al., Central nervous system toxicity of metallic nanoparticles, Int J Nanomedicine, 10 (2015) 4321-4340.

Tanaka, Y., et al., The effects of cutting solutions on the viability of GABAergic interneurons in cerebral cortical slices of adult mice, J. Neurosci. Methods, 171 (2008) 118-125.

Sciarretta, C. and Minichiello, L., The preparation of primary cortical neuron cultures and a practical application using immunofluorescent cytochemistry, Methods Mol. Biol., 633 (2010) 221-231.

Singhal, A., et al., Nanoparticle-mediated catalase delivery protects human neurons from oxidative stress, Cell Death Dis., 4 (2013) e903.

J.S. Lunn, S.A. Sakowski, J. Hur, E.L. Feldman, Stem cell technology for neurodegenerative diseases, 25 Ann. Neurol., 70 (2011) 353-361.

C. Soto, S. Pritzkow, Protein misfolding, aggregation, and conformational strains in neurodegenerative diseases, Nat. Neurosci., 21 (2018) 1332-1340.

J.A. Bertout, S.A. Patel, M.C. Simon, The impact of O2 availability on human cancer, Nat. Rev. Cancer, 8 (2008) 967-975. 30.

J.W. Shim, J.R. Madsen, VEGF Signaling in Neurological Disorders, International journal of molecular sciences, 19 (2018) 275.

K. Hu, S. Babapoor-Farrokhran, M. Rodrigues, M. Deshpande, B. Puchner, F. Kashiwabuchi, S.J. Hassan, L. Asnaghi, J.T. Handa, S. Merbs, C.G. Eberhart, G.L. Semenza, S. Montaner, A. Sodhi, Hypoxia-inducible factor 1 upregulation of both VEGF and ANGPTL4 is required to promote the angiogenic 5 phenotype in uveal melanoma, Oncotarget, 7 (2016) 7816-7828.

E. Storkebaum, P. Carmeliet, VEGF: a critical player in neurodegeneration, The Journal of clinical investigation, 113 (2004) 14-18.

K.J. Barnham, C.L. Masters, A.I. Bush, Neurodegenerative diseases and oxidative stress, Nature reviews. Drug discovery, 3 (2004) 205-214.

M. Schieber, N.S. Chandel, ROS function in redox signaling and oxidative stress, Curr. Biol., 24 (2014) R453-462.

A.A. Dayem, H.Y. Choi, J.H. Kim, S.G. Cho, Role of oxidative stress in stem, cancer, and cancer stem cells, Cancers (Basel), 2 (2010) 859-884.

F. Panza, M. Lozupone, G. Logroscino, B.P. Imbimbo, A critical appraisal of amyloid-beta-targeting 15 therapies for Alzheimer disease, Nat. Rev. Neurol., 15 (2019) 73-88.

D.G. Smith, R. Cappai, K.J. Barnham, The redox chemistry of the Alzheimer's disease amyloid beta peptide, Biochim. Biophys. Acta, 1768 (2007) 1976-1990.

M. Rosini, E. Simoni, A. Milelli, A. Minarini, C. Melchiorre, Oxidative stress in Alzheimer's disease: are we connecting the dots?, J. Med. Chem., 57 (2014) 2821-2831.

F. Zhang, R. Zhong, H. Qi, S. Li, C. Cheng, X. Liu, Y. Liu, W. Le, Impacts of Acute Hypoxia on Alzheimer's Disease-Like Pathologies in APP(swe)/PS1(dE9) Mice and Their Wild Type Littermates, Front. Neurosci., 12 (2018) 314-314.

V.W. Chow, M.P. Mattson, P.C. Wong, M. Gleichmann, An overview of APP processing enzymes and products, Neuromolecular Med., 12 (2010) 1-12.

C. Kerridge, D.I. Kozlova, N.N. Nalivaeva, A.J. Turner, Hypoxia Affects Neprilysin Expression Through Caspase Activation and an APP Intracellular Domain-dependent Mechanism, Front. Neurosci., 9 (2015) 426-426.

S. Varadarajan, S. Yatin, M. Aksenova, D.A. Butterfield, Review: Alzheimer's amyloid beta-peptide-associated free radical oxidative stress and neurotoxicity, J. Struct. Biol., 130 (2000) 184-208.

T. Chitnis, H.L. Weiner, CNS inflammation and neurodegeneration, J. Clin. Invest., 127 (2017) 3577-3587.

M.T. Heneka, et al., Neuroinflammation in 5 Alzheimer's disease, Lancet Neurol., 14 (2015) 388-405.

N. Pankratz, T. Foroud, Genetics of Parkinson disease, Genet. Med., 9 (2007) 801-811.

A.R. Green, B.D. Mitchell, A.F. Tordoff, M.B. Youdim, Evidence for dopamine deamination by both type A and type B monoamine oxidase in rat brain in vivo and for the degree of inhibition of enzyme necessary for increased functional activity of dopamine and 5-hydroxytryptamine, Br. J. Pharmacol., 60 10 (1977) 343-349.

T. Nagatsu, M. Sawada, Molecular mechanism of the relation of monoamine oxidase B and its inhibitors to Parkinson's disease: possible implications of glial cells, J. Neural Transm. Suppl., (2006) 53-65.

H.-L. Sun, B.-L. Sun, D.-W. Chen, Y. Chen, W.-W. Li, M.-Y. Xu, Y.-Y. Shen, Z.-Q. Xu, Y.-J. Wang, X.-L. Bu, 15 Plasma α-synuclein levels are increased in patients with obstructive sleep apnea syndrome, Annals of Clinical and Translational Neurology, 6 (2019) 788-794.

(56) References Cited

OTHER PUBLICATIONS

Q. Xu, H. Guo, X. Zhang, B. Tang, F. Cai, W. Zhou, W. Song, Hypoxia regulation of ATP13A2 (PARK9) gene transcription, J. Neurochem., 122 (2012) 251-259.

F. Shephard, O. Greville-Heygate, S. Liddell, R. Emes, L. Chakrabarti, Analysis of Mitochondrial 20 haemoglobin in Parkinson's disease brain, Mitochondrion, 29 (2016) 45-52.

K.C. Arthur, A. Calvo, T.R. Price, J.T. Geiger, A. Chio, B.J. Traynor, Projected increase in amyotrophic lateral sclerosis from 2015 to 2040, Nature communications, 7 (2016) 12408-12408.

J.D. Rothstein, Current hypotheses for the underlying biology of amyotrophic lateral sclerosis, Ann. Neurol., 65 Suppl 1 (2009) S3-9.

S.-M. Kim, H. Kim, J.-S. Lee, K.S. Park, G.S. Jeon, J. Shon, S.-W. Ahn, S.H. Kim, K.M. Lee, J.-J. Sung, K.-W. Lee, Intermittent hypoxia can aggravate motor neuronal loss and cognitive dysfunction in ALS mice, PLoS One, 8 (2013) e81808-e81808.

S.M. Kim, H. Kim, U.S. Lee, K.S. Park, G.S. Jeon, J. Shon, S.W. Ahn, S.H. Kim, K.M. Lee, J.J. Sung, K.W. Lee, Intermittent hypoxia can aggravate motor neuronal loss and cognitive dysfunction in ALS mice, PLoS 30 One, 8 (2013) e81808.

F.O. Walker, Huntington's disease, The Lancet, 369 (2007) 218-228.

T. Velusamy, A.S. Panneerselvam, M. Purushottam, M. Anusuyadevi, P.K. Pal, S. Jain, M.M. Essa, G.J. Guillemin, M. Kandasamy, Protective Effect of Antioxidants on Neuronal Dysfunction and Plasticity in Huntington's Disease, Oxid. Med. Cell. Longev., 2017 (2017) 3279061.

U. Bayani, V.S. Ajay, Z. Paolo, R.T. Mahajan, Oxidative Stress and Neurodegenerative Diseases: A Review of Upstream and Downstream Antioxidant Therapeutic Options, Curr. Neuropharmacol., 7 5 (2009) 65-74.

R. Rodrigo, R. Fernández-Gajardo, R. Gutiérrez, J.M. Matamala, R. Carrasco, A. Miranda-Merchak, W. Feuerhake, Oxidative stress and pathophysiology of ischemic stroke: novel therapeutic opportunities, CNS Neurol. Disord. Drug Targets, 12 (2013) 698-714.

C. Saraiva, C. Praça, R. Ferreira, T. Santos, L. Ferreira, L. Bernardino, Nanoparticle-mediated brain 10 drug delivery: Overcoming blood-brain barrier to treat neurodegenerative diseases, J. Control. Release, 235 (2016) 34-47.

W. Li, S. Yang, Targeting oxidative stress for the treatment of ischemic stroke: Upstream and downstream therapeutic strategies, Brain circulation, 2 (2016) 153-163.

C.L. Allen, U. Bayraktutan, Oxidative stress and its role in the pathogenesis of ischaemic stroke, Int. 15 J. Stroke, 4 (2009) 461-470.

F. Lupoli, T. Vannocci, G. Longo, N. Niccolai, A. Pastore, The role of oxidative stress in Friedreich's ataxia, FEBS Lett., 592 (2018) 718-727.

J. Tamarit, É. Obis, J. Ros, Oxidative stress and altered lipid metabolism in Friedreich ataxia, Free Radic. Biol. Med., 100 (2016) 138-146.

Y.J. Yu, R.J. Watts, Developing therapeutic antibodies for neurodegenerative disease, Neurotherapeutics : the journal of the American Society for Experimental Neuro Therapeutics, 10 (2013) 459-472.

A. Compston, A. Coles, Multiple sclerosis, The Lancet, 372 (2008) 1502-1517.

X.M. Wang, B. Walitt, L. Saligan, A.F. Tiwari, C.W. Cheung, Z.J. Zhang, Chemobrain: a critical review 25 and causal hypothesis of link between cytokines and epigenetic reprogramming associated with chemotherapy, Cytokine, 72 (2015) 86-96.

J. Zhao, H. Zuo, K. Ding, X. Zhang, Z. Bi, H. Cheng, Changes in plasma IL-1β, TNF-α and IL-4 levels are involved in chemotherapy-related cognitive impairment in early-stage breast cancer patients, American journal of translational research, 12 (2020) 3046-3056.

R.W. Paterson, et al., The emerging spectrum of 5 COVID-19 neurology: clinical, radiological and laboratory findings, Brain 143 (2020) 3104-3120.

M.A. Ellul, L. Benjamin, B. Singh, S. Lant, B.D. Michael, A. Easton, R. Kneen, S. Defres, J. Sejvar, T. Solomon, Neurological associations of COVID-19, Lancet Neurol., 19 (2020) 767-783.

P. Mehta, D.F. McAuley, M. Brown, E. Sanchez, R.S. Tattersall, J.J. Manson, COVID-19: consider cytokine storm syndromes and immunosuppression, Lancet, 395 (2020) 1033-1034.

S.G. Schutz, J. Robinson-Papp, HIV-related neuropathy: current perspectives, HIV AIDS (Auckl.), 5 (2013) 243-251.

L. Al-Harthi, E. Campbell, J.A. Schneider, D.A. Bennett, What HIV in the Brain Can Teach US About SARS-CoV-2 Neurological Complications?, AIDS Res. Hum. Retroviruses, 37 (2021) 255-265 (Epub Aug. 10, 2020).

J. Lee, S. Giordano, J.H. Zhang, Autophagy, mitochondria and oxidative stress: cross-talk and redox 15 signalling, Biochem. J., 441 (2012) 523-540.

A. Kaus, D. Sareen, ALS Patient Stem Cells for Unveiling Disease Signatures of Motoneuron Susceptibility: Perspectives on the Deadly Mitochondria, ER Stress and Calcium Triad, Front. Cell. Neurosci., 9 (2015) 1-26.

D.P. Gelain, G. Antonio Behr, R. Birnfeld de Oliveira, M. Trujillo, Antioxidant therapies for 20 neurodegenerative diseases: mechanisms, current trends, and perspectives, Oxid. Med. Cell. Longev., 2012 (2012) 895153-895153.

H. Fritz, D. Kennedy, D. Fergusson, R. Fernandes, S. Doucette, K. Cooley, A. Seely, S. Sagar, R. Wong, D. Seely, Vitamin A and retinoid derivatives for lung cancer: a systematic review and meta analysis, PLoS One, 6 (2011) e21107.

* cited by examiner

TgCRND8 Mice+Saline          TgCRND8 Mice+aAβ-BTRA-NC a)

b)

a) Whole body Biodistribution b) Ex vivo Brain Accumulation

BLOOD-BRAIN BARRIER-PENETRATING NANOTHERANOSTICS FOR ACUTE AND CHRONIC NEURODEGENERATIVE DISEASES AND THE LIKE

CROSS REFERENCE TO RELATED APPLICATIONS

This application is a national stage application under 35 U.S.C. 371 of International Application No. PCT/CA2021/051356, filed Sep. 29, 2021, which in turn claims the benefit under 35 U.S.C. 119(e) of U.S. Provisional Ser. No. 63/085,729, filed Sep. 30, 2020, the contents of each of which are hereby incorporated by reference into the present disclosure.

FIELD OF THE INVENTION

The present invention is related to novel activatable particles for use in diagnostic and therapeutic application, particularly to metal oxide containing particles that cross the blood-brain barrier (BBB) and reduce ROS and oxidative stress in the brain and serve as a magnetic resonance imaging contrast enhancer to diagnose and treat acute/chronic neuroinflammatory and neurodegenerative diseases arising from a variety of causes.

BACKGROUND

Neurodegenerative disorders exemplified by conditions such as Alzheimer disease (AD), Parkinson disease (PD), Huntington's disease (HD), stroke, Amyotrophic Lateral Sclerosis (ALS), Friedreich's ataxia (FRDA) and Multiple sclerosis (MS) are characterized by the loss of particular populations or loci of neural cells [1]. The progressive loss of specific neuronal and support cell population, protein misfolding and aggregates are linked to neurodegenerative diseases [2]. Low oxygen supply (hypoxia) is observed during the progression of neurodegenerative diseases. Hypoxia leads to chronic up regulation of hypoxia-inducible factor-1 (HIF-1), a transcriptional activator which plays a pivotal role in adaptive responses by binding to many genes and regulation of genes involved in red blood cell production, energy metabolism, angiogenesis, apoptosis, pH balance and anaerobic glycolysis [3, 4]. Upon activation, HIF-1 binds to the hypoxic responsive element, thereby promoting transcription of various genes including vascular endothelial growth factor (VEGF) and genes encoding for glucose transporters [5]. Recent advances in neurodegenerative disease have shown that VEGF is a key player in neurological disorder and has direct effects on neural cells [6]. The expression of VEGF further induces angiogenesis and plays a key role in promoting neurodegenerative diseases [4]. AD, PD, stroke and ALS are the most common age-related neurodegenerative diseases [1]. Hypoxia has been implicated in the progression of many of these diseases [7] and plays a significant role in promoting oxidative stress within the brain. Oxidative stress is characterized by excessive production of reactive oxygen species (ROS) [8]. Added to this is the fact that for many developmental stages including adult state the brain expresses substantially lowered levels of ROS detoxifying enzymes compared to other tissues. Reactive nitrogen and reactive oxygen species (ROS) may be generated in several forms (hydroxyl radicals, superoxide anions and hydrogen peroxide being the most widely recognized and studied) through a variety of both pathologic and natural metabolic processes affecting the above states.

Such radicals diffuse locally depending upon temporal half-life modifying cellular function [9].

Among different neurodegenerative diseases, AD is the most common cause of dementia in the elderly affecting 40-50 million people worldwide, including ~5.8 million Americans [10]. AD has been centered on amyloid beta (Aβ), a peptide of 39-43 amino acids that appear to be the main constituent of amyloid plaques in the brains of AD patients [11]. Increasing evidence has shown that early events in AD are associated with hypoxia and oxidative stress [12]. Hypoxia up regulates Aβ production and modifies the tau phosphorylation [13]. Aβ is generated through the sequential actions of β- and γ-secretases on amyloid precursor protein (APP) [14]. Hypoxic microenvironment favors the progression of AD by elevating the APP and presenilin-1 (PS-1) [13]. Hypoxia also leads to reduced expression of neprilysin (NEP), an enzyme responsible for Aβ degeneration [15]. In addition, hypoxia results in a more acidic environment that gives rise to tau hyperphosphorylation. Many studies have concluded that the Aβ peptide is capable of generating free radicals through the generation of $H_2O_2$ as well as through stimulating inflammatory cells [16]. Neuropathology such as neuro-inflammation induced by ROS, e.g. $H_2O_2$, reportedly occur prior to overt amyloid plaque accumulation and cognitive AD progression [17]. In addition, ROS, Aβ oligomers and fibrils are known to activate microglia and astrocytes, triggering the secretion of pro-inflammatory cytokines that promote disease progression [18].

PD is also another neurodegenerative disorder affecting 1% of the population over 55 years of age [19]. The loss of dopamine (DA) and presence of intracytoplasmic proteinaceous inclusions called Lewy bodies (LB) are considered as the main deficit in PD [19]. A major degradative pathway for DA is its oxidative deamination by monoamine oxidases A and B [20]. This process results in the enzymatic production of $H_2O_2$[21]. High ROS concentrations are associated with a decline in cognitive functions [21]. Hypoxia has shown to enhance the α-synuclein expression that is a key protein in neuroinflammatory diseases, including LB dementia [22]. Similarly, ATP13A2 (PARKS) are reported to be associated with PD. Research has shown that hypoxia up regulates ATP13A2 transcription via HIF-1alpha (HIF-1α) in dopaminergic cells [23]. The mitochondrial localization of hemoglobin as a result of hypoxic microenvironment is also linked to PD [24]. ALS is a progressive and fetal neurodegenerative disease that affects nerve cells in the brain and spinal cord, causing loss of muscle control [25]. The worldwide ALS incidence is estimated around 2 per 100,000 people [25]. Pathogenic themes in ALS include excitotoxicity, oxidative stress, mitochondrial dysfunction, neuroinflammation, altered energy metabolism, and most recently RNA mis-processing [25]. There are three genes being identified to be linked with ALS, TARDBP, FUS and C9orf72, which play substantial role in RNA misprocessing in the pathogenesis of ALS. Studies on the cellular biology of downstream events over the last two decades have led to development of multiple interconnected pathogenic themes in ALS [26]. Studies have shown that patients with ALS frequently experience hypoxia, which accelerates disease progression. Motor neurons under hypoxic conditions fail to survive and undergo degeneration [27]. Pre-clinical studies performed on an ALS mice model have shown higher levels of oxidative stress, aggravation in motor neuronal loss, and neuromuscular weakness [28].

HD is a complex and severe disorder characterized by the gradual and progressive loss of neurons, predominantly in the striatum, which leads to typical motor and cognitive impairments associated with this pathology [29]. It is reported that polyglutamine expansion associated oxidative stress that leads to caspase mediated neuronal cell death is considered as a potential cause of neuropathological changes in HD [30]. ROS targets neuronal cells by promoting formation of DNA-protein cross-linked harmful adducts through oxidation of both the backbone, and the side chain of protein and DNA molecules [31]. Various indices of free radical mediated damage have been identified as etiologies of HD associated neurodegenerative conditions [31].

Ischemic stroke is a serious health, social, and economic problem of current societies. It is the third leading cause of death, after cancer and myocardial infarction, and the first cause of disability in patients in western world [32]. During stroke, the brain is deprived of blood supply by a bleeding vessel (hemorrhagic stroke) or occlusion of a vessel due to a blood clot (ischemic stroke) [33]. Oxidative stress is thought to play a key role in pathogenesis of acute ischemic stroke [34]. ROS produced during ischemic and reperfusion phases of ischemic stroke can attack cerebral tissue [35]. There is evidence that a rapid increase in the production of ROS immediately after acute ischemic stroke rapidly overwhelm antioxidant defenses, causing further tissue damage [32].

FRDA is a rare mitochondrial neurodegenerative disease and characterized by a progressive degeneration of large sensory neurons and cardiomyopathies [36]. FRDA comprises an autosomal recessive disease that causes progressive damage to the nervous system resulting in symptoms ranging from Gait disturbance and speech problems to heart disease [36]. It is shown that FDDA pathology is associated with the presence of iron deposits and oxidative stress [36]. Although the mechanism causing oxidative stress in FRDA is not completely understood, many evidences suggest that oxidative stress plays a central role in the pathophysiology of FRDA. It has been suggested that oxidative stress would be the consequence of altered cellular iron metabolism, caused by deficiency in iron-sulfur cluster biogenesis [37].

MS is another multifactorial autoimmune disease of the central nervous system (CNS) that is characterized by chronic inflammation, demyelination, and axon and neuronal loss. Depending on the location of demyelinating lesions, MS patients can develop almost any neurological signs or symptoms, including motor, sensory, and cognitive impairment [38]. The most common symptoms are numbness, muscle spasms, ataxia, walking difficulties, bladder or visual problems, fatigue, pain, depression, and MS-related dementia [39]. However, inflammation is a major driver of the pathology. In addition, oxidative stress contributes to tissue injury and promotes existing inflammatory response. Due to the inflammatory nature of MS, targeting of the immune response is the most widely used therapeutic approach.

"Chemobrain", refers to irreversible and severe side effects of chemotherapy that causes long-term cognitive impairment [40]. Although many chemodrugs are not permeable to the brain, cytokines, along with their systemic effects, as adverse effects of chemotherapy, could induce peripheral and CNS neuropathy [40]. There is strong evidence that changes in peripheral cytokines are correlated with the development of chemobrain in patients of different types of cancers treated with commonly used chemotherautic drugs [40]. Studies have shown that the plasma level of inflammatory cytokines e.g. IL-1β, TNF-α and IL-4 levels were higher in early stage breast cancer patients who underwent chemotherapy and showed chemotherapy-related cognitive impairment (CRCI) [41]. Thus, early diagnosis and intervention of neuroinflammation induced by chemotherapeutic drugs are needed for cancer patients after chemotherapy.

Viral infections often induce neuroinflammation either via direct infection when the viruses enter the brain, or by indirect effect of pro-inflammatory cytokines secreted by infected cells or activated immune cells. Coronaviruses, for instance, severe acute respiratory syndrome (SARS) caused by SARS-CoV or SARS-CoV-2 (in COVID-19), Middle East respiratory syndrome (MERS) by MERS-CoV have shown to cause neuroinflammation [42, 43]. SARS coronaviruses are associated in causing occasional disease of the CNS and peripheral nervous system (PNS) [42, 43]. They are reported to cause encephalitis, an inflammation of the brain parenchyma, usually caused by an infection or the body's immune defenses. SARS coronaviruses also induce other neurological disorders, e.g., seizures, neuromuscular disease, predominantly motor neuropathy and myopathy. The MERS viruses could cause acute disseminated encephalomyelitis (ADEM), cerebrovascular disease and Bickerstaff's brainstem encephalitis along with neuropathy. Recently, SARS-CoV-2 has been linked to neurological disorders with diverse immune-inflammatory processes such as ADEM-like demyelination, multiple sclerosis, optic neuritis, and encephalitis particularly with hemorrhagic changes. SARS-CoV-2 also causes meningitis, myelitis, or CNS vasculitis infection or inflammation and Guillain-Barré syndrome [42, 43]. SARS-CoV-2 infection can also induce other acute neuropathies which can trigger thrombotic vascular events like ischemic stroke [42]. Cytokine storm (combined or independent effects of sepsis, hypoxia and immune hyperstimulation) are postulated to be the underlying mechanisms for the encephalopathy [44]. Thus, timely detection of neuroinflammation and mini-strokes and therapeutic intervention with nanoparticles able to cross the BBB are needed to effectively prevent further damage to the CNS caused by viral infection.

Human immunodeficiency virus (HIV) induces distal symmetric polyneuropathy (DSP), one of the most common neurological complications [45]. DSP is characterized by a combination of signs and symptoms that include decreased deep tendon reflexes at the ankles and decreased sensation in the distal extremities as well as paresthesias, dysesthesias, and pain in a symmetric stocking—glove distribution. Studies have shown the HIV causes neurotoxicity through inflammation and viral proteins [45]. Additionally, HIV-infected individuals may also develop HIV-associated dementia (HAD). Once HIV invades inside the brain parenchyma, they infect the perivascular macrophages, microglia, and to a lesser extent astrocyte. The neurotoxic viral protein gp120, Tat, Nef, and Vpr induces the glial inflammation. HIV may also increase the trafficking of hyperactivated immune cells into the brain (the so-called neuroimmune axis) [46]. An optimal penetration of therapeutic agents inside the brain could help to reduce the HIV associated brain inflammation.

In all the neurodegenerative disorders, free radicals play a major role. The micro environmental changes in brain due to hypoxia leading to oxidative stress that is vulnerable to neurons [7]. The high levels of ROS are intimately linked to the appearance of neuronal death in various neurological disorders [7, 8]. Because of their extensive polarization, relative size and post-mitotic nature, neurons are particularly sensitive to oxidative damage and the accumulation of aggregated or damaged cytosolic compounds [31]. The nature of the neuronal cell death observed is well established for many neurodegenerative conditions [31]. Under such conditions however, neural cells may experience more than one mode of cell death, often relating to the severity or duration of cellular stress, the strength of the prevailing trophic support of the current cellular network, and levels of endogenous cellular redox and mitochondrial integrity [47]. Though the extent and nature of these stresses differ in various neurodegenerative diseases, the above highlights a number of common features observed which ultimately induce endoplasmic reticulum (ER) and oxidative stress, mitochondrial dysfunction, and the impairment of proteasome function with resulting protein aggregation [48]. These changes are often interrelated, causing disruption of normal neuronal function and leading eventually to neuronal cell death [31].

ROS and oxidative stress have critical role in major neurodegenerative diseases including AD, PD, HD, ALS, FRDA and MS. To date, different compounds such as vitamin A, C and E, selenium, curcumin, colostrinin, glutathione (GSH), tirilazad, N-acetylcysteine, ebselen, selegiline, idebenone, and extract of Gingko biloba have been proposed to be used as antioxidants [49]. However, results from these compounds have been disappointing [49]. In addition, some of the developing therapies have induced acute or long-term toxic effects, including oxidative stress itself [49]. For example, a large clinical trial The Beta-Carotene and Retinol Efficacy Trial (CARET) evaluated the effect of oral intake of beta-carotene and retinol in men and women at high risk for lung cancer had to be discontinued due to increased incidence of lung cancer, cardiovascular disease, and mortality [50]. Following this clinical trial, many studies have shown that vitamin A may act as a strong pro-oxidant to living cells [49]. Similarly, activities of many antioxidants such as vitamin C or GSH are highly dependent on other antioxidants. Over supplying one antioxidant in large doses might also cause undesired side reactions and peroxidations. Other reasons for antioxidant therapy failure are poor in vivo efficiency of the agents, lack of target specificity and overproduction of ROS in living system and application of the intervention at later stage of disease [51]. In addition, the blood-brain barrier (BBB) also restricts the entry of therapeutic agents into the brain and deeper part of the brain e.g. hippocampus, midbrain and brain stem [51]. As a result, the utility of such compounds in clinical setting is limited due to their safety concerns and inconsistent efficacy response. Therefore, there is an urgent need for the new novel strategies to reduce the oxidative stress in neurodegenerative diseases to rescue neurons and slowing the disease progression.

For AD the standard of care treatments only manages symptoms, and currently there is no curative or approved disease-modifying therapeutics for AD [10]. Despite tremendous efforts and expenditures so far, most clinical trials over the past decades have failed to achieve meaningful clinical benefits for AD [52]. Many contributing factors to such failures have been postulated to include variable origins and rates of disease progression, inappropriate therapeutic targets and patient selection, late intervention, and suboptimal dosing [10]. The late intervention of the disease is largely due to the lack of a sensitive and accurate detection method for early stage AD [52]. Neurobiological changes in AD can occur much earlier than the cognitive decline diagnosed by clinical methods. For example, changes in cerebrospinal fluid (CSF) biomarkers, e.g. hyperphosphorylated tau (p-tau) and amyloid β-42 (Aβ42) occur 15 to 20 years prior to the clinical onset of AD [53]. However, clinical diagnosis of AD is conducted in accordance with exclusion criteria by clinical symptoms (e.g. impaired memory and cognitive function) [53]. The diagnostic sensitivity and specificity of these methods are relatively low and are only definitive when identifying AD at its irreversible stages [53]. Therefore, for early detection and complementary imaging-based diagnosis of AD, fluid biomarkers (e.g., CSF Aβ42 and p-tau) are measured. However, CSF sampling is labor intensive, costly, and invasive; it requires lumbar puncture at L3-L5 which carries some risk of CNS injury infection. Therefore analysis of CSFs biomarkers by this method is not broadly practiced clinically [53].

Various imaging techniques have been applied to detect AD non-invasively including positron emission tomography (PET), PET/computed tomography (CT), single-photon emission computed tomography (SPECT) scans and magnetic resonance imaging (MRI) [54]. PET scan measures metabolic changes using radiolabeled fluorodeoxyglucose ($[^{18}F]$ FDG), or Aβ plaques by amyloid tracers such as Pittsburgh Compound-B (PiB). However, PET scan requires use of expensive radioactive probes of limited availability. In addition, high levels of Aβ plaques found in later stages of AD may not correlate well with AD dementia [55]. By contrast MRI is a powerful tool for clinical assessment of patients with suspected AD by measuring the volume and structure changes in the brain [56]. Structural MRI can determine atrophy of medial temporal lobe, hippocampal, entorhinal cortex and subiculum, as potential early indicators of future AD dementia risk [57]. To enhance MRI signal, gadolinium (Gd) based contrast agents are commonly used clinically. However application of Gd-based contrast agents have been linked to significant nephrogenic systemic fibrosis in some patients, particularly those with severe renal dysfunction [58]. Studies have also shown deposition of Gd in the brain and bones can occur over an extended periods [59]. Moreover the majority of current MRI contrast agents possess poor selectivity and limited ability to penetrate the BBB for early and accurate detection of CNS/CSF biomarkers in AD [60]. Therefore, there is a continued and urgent medical need for finding new strategies to early-stage diagnosis of AD with a treatment combo.

SUMMARY OF THE INVENTION

In one embodiment, the present disclosure relates to multifunctional nanoparticles compositions, including pharmaceutical compositions, for the diagnosis and treatment of a central nervous system (CNS) disease such as Alzheimer's Disease (AD), Parkinson's Disease (PD), Huntington's Disease, stroke, neuroinflammation caused by bacteria or virus, chemotherapy and so forth.

In one embodiment, the present invention provides for a brain-targeted (BT) and reactive oxygen species (ROS)-activable nanoconstructs (BTRA-NC), the BTRA-NC comprising a metal oxide nanoparticle embedded in a matrix of lipids/brain targeted polymer (BTP), the BTRA-NC being configured to facilitate blood brain barrier (BBB) penetration and accumulation of the NC in a disease area of the CNS.

In one embodiment, the brain-targeted and ROS-activable nanoconstructs further comprises a functional moiety conjugated onto the BTP that binds to and/or complexes with a biomarker in the CNS.

In another embodiment of the brain-targeted and ROS-activable nanoconstructs of the present invention, the CNS biomarker is a pathological biomarker of a neurodegenerative disease or stroke.

In another embodiment of the brain-targeted and ROS-activable nanoconstructs of the present invention, the neurodegenerative disease is one or more of Alzheimer disease (AD), Parkinson disease (PD), Huntington's disease (HD), Amyotrophic Lateral Sclerosis (ALS), Friedreich's ataxia (FRDA) and Multiple sclerosis (MS), viral or bacterial neuroinflammation and chemobrain.

In another embodiment of the brain-targeted and ROS-activable nanoconstructs of the present invention, the functional moiety is an antibody, a targeting moiety, a neurotrophic factor, a peptide, a nucleic acid, a small molecule modifiers of programmed cell death (PCD), a detectable moiety, a labeling agent, an imaging agent or mixtures thereof.

In another embodiment of the brain-targeted and ROS-activable nanoconstructs of the present invention, the BTRA-NC is formulated with a pharmaceutically acceptable vehicle suitable for intravenous injection.

In another embodiment of the brain-targeted and ROS-activable nanoconstructs of the present invention, the functional moiety is an anti-amyloid $\beta$-42 antibody (aA$\beta$).

In another embodiment of the brain-targeted and ROS-activable nanoconstructs of the present invention, the brain-targeted and ROS activable nanocostructs further includes a therapeutic agent embedded into the matrix of lipids/BTP.

In another embodiment of the brain-targeted and ROS-activable nanoconstructs of the present invention, the therapeutic agent includes one or more of a nucleic acid, a peptide, a therapeutic antibody, a small molecule modifiers of programmed cell death (PCD), a neurotrophic factor, a growth factor, an immunosuppressive agent, an anti-inflammatory agent, an anti-apoptotic agent, a cytokine inhibitor, a metabolism modulator, a vascular modulator, and/or a cell proliferation inhibitor.

In another embodiment of the brain-targeted and ROS-activable nanoconstructs of the present invention, the therapeutic agent is one or more of glial cell line-derived neurotrophic factor (GDNF), brain-derived neurotrophic factor (BDNF), neurotrophin, cerebral dopamine neurotrophic factor, mesencephalic or astrocyte-derived neurotrophic factor.

In another embodiment of the brain-targeted and ROS-activable nanoconstructs of the present invention, the therapeutic agent is GDNF.

In another embodiment of the brain-targeted and ROS-activable nanoconstructs of the present invention, the therapeutic agent is tacrolimus (FK506).

In another embodiment of the brain-targeted and ROS-activable nanoconstructs of the present invention, the therapeutic agent is N-benzyloxycarbonyl-Asp (OMe)-Glu (OMe)-Val-Asp (OMe)-fluoromethylketone (Z-DEVD-FMK).

In another embodiment of the brain-targeted and ROS-activable nanoconstructs of the present invention, the therapeutic agent is curcumin.

In another embodiment of the brain-targeted and ROS-activable nanoconstructs of the present invention, the therapeutic agent is an RNA molecule.

In another embodiment of the brain-targeted and ROS-activable nanoconstructs of the present invention, the BTRA-NC has a particle size between about 40 nm and about 160 nm.

In another embodiment of the brain-targeted and ROS-activable nanoconstructs of the present invention, the BTRA-NC are stabilized by a positively charged polyelectrolyte.

In another embodiment of the brain-targeted and ROS-activable nanoconstructs of the present invention, the metal oxide is $MnO_2$.

In another embodiment, the present invention is a method of preparing brain-targeted and ROS-activable nanoconstructs (BTRA-NC), the method comprising of steps of (a) coating metal oxide nanoparticles with a lipid or a polymer to obtain hydrophobic or hydrophilic nanoparticle surface; (b) mixing the coated metal oxide nanoparticles and a brain targeted polymer in a lipid matrix to form an emulsion, and (c) ultrasonicating or high pressure homogenizing the emulsion to form brain-targeted and ROS-activable nanoconstructs.

In one embodiment of the method of preparing the BTRA-NC of the present invention, the metal oxide nanoparticles are $KMnO_4$ nanoparticles, and the method further comprises mixing the $KMnO_4$ nanoparticles with a positively charged polyelectrolyte to obtain stabilized $MnO_4$ nanoparticles (MD NPs).

In another embodiment of the method of preparing the BTRA-NC of the present invention, the method comprises mixing the MD NPs with lipids to form an emulsion in which the MD NPs are coated with the lipids, coating the emulsion with a terpolymer, and homogenizing the emulsion coated with the terpolymer to obtain a homogeneous nanoparticle emulsion.

In another embodiment of the method of preparing the BTRA-NC of the present invention, the brain targeted polymer is an antibody to target a site in the central nervous system (CNS) behind a BBB.

In another embodiment of the method of preparing the BTRA-NC of the present invention, the brain targeted polymer is anti-amyloid $\beta$ (A$\beta$) antibody, GDNF, FK506, DEVD, curcumin or an RNA molecule.

In another embodiment, the present invention provides for a method of treating and diagnosing ("theranostics") a CNS disease or condition in a subject in need, the method comprising delivering a therapeutic agent across the BBB of the subject to a disease are of the CNS by administering to the subject an effective amount of the BTRA-NC according to an embodiment of the present invention, wherein the CNS biomarker is a pathological biomarker of a neurodegenerative disease or stroke to reduce ROS and oxidative stress in the subject thereby treating the subject, and detecting the multifunctional nanoparticles-produced contrast agent using magnetic resonance imaging (MRI) and using said MRI images to diagnose the subject.

In one embodiment of the theranostics method of the present invention, the theranostics method comprises reducing hypoxia in the disease area by producing oxygen in the disease area.

In another embodiment, the present invention provides for a use of a BTRA-NC of the present invention for treating and diagnosing ("theranostics") using magnetic resonance imaging a CNS disease or condition in a subject in need.

In another embodiment, the present invention provides for a BTRA-NC of the present invention for the preparation of a medicament for the treatment and diagnosis ("theranostics") using magnetic resonance imaging of a CNS disease or condition in a subject in need.

In another embodiment, the present invention is a magnetic resonance (MR) contrast agent for a CNS disease-affected area, wherein the MR contrast agent comprises a BTRA-NC according to any embodiment of the present invention.

In another embodiment, the present invention is a method for acquiring an image of a subject using a magnetic resonance imaging (MRI) comprising: (a) administering to the subject an image enhancing amount of a BTRA-NC according to an embodiment of the present invention wherein the metal oxide is $MnO_2$, (b) obtaining an MRI image of the subject in diseased regions where the MDNP react with ROS ($H_2O_2$) producing paramagnetic $Mn^{2+}$ ions that enhance the MRI contrast.

In another embodiment, the present invention is a method of protecting primary neurons from oxidative stress comprising administering to a subject in need an effective amount of a brain-targeted and ROS-activable nanoconstructs of the present invention.

In another embodiment, the present invention is a method of treating fibrillation and neurotoxicity of amyloid beta (Aβ) comprising administering an anti-amyloid β-42 antibody (aAβ)-conjugated, brain-targeted (BT) and ROS-activable (RA) metal oxide-containing nanoconstructs (NC) of the present invention to a subject in need. In one aspect, the metal oxide is $MnO_2$.

In another embodiment the present invention is a use of the BTRA-NC of the present invention for treating fibrillation and neurotoxicity of amyloid beta (Aβ).

In another embodiment, the present invention provides for a use of the BTRA-NC of the present invention in the manufacture of a medicament for the treatment of fibrillation and neurotoxicity of amyloid beta (Aβ).

In another embodiment, the present invention is a method of treating neuroinflammation, a neurological disorder or a stroke caused by viruses (e.g., SARS, MARS, SARS-CoV-2, and HIV) or by chemotherapy, the method comprising administering a BTRA-NC of the present invention, wherein the functional moiety binds to and/or complexes with a CNS biomarker of the neuroinflammation, the neurological disorder or the stroke.

In another embodiment the present invention is a use of the BTRA-NC of the present invention for treating neuroinflammation, a neurological disorder or a stroke caused by viruses or by chemotherapy.

In another embodiment, the present invention provides for a use of the BTRA-NC of the present invention in the manufacture of a medicament for the treatment of neuroinflammation, a neurological disorder or a stroke caused by viruses or by chemotherapy.

In another embodiment, the present invention provides for a method of treating ischemic stroke brain comprising administering at least one of the brain targeted and ROS-activable nanoconstructs of the present invention to a subject in need.

In another embodiment, the present invention provides for a use of the BTRA-NC of the present invention for treating ischemic stroke brain.

In another embodiment, the present invention provides for a use of the BTRA-NC of the present invention in the manufacture of a medicament for the treatment of ischemic stroke brain.

In another embodiment, the present invention provides for a method of delivering a neurotrophic factor to the brain of a subject, the method comprising administering to the subject a BTRA-NC of the present invention having a neurotrophic factor embedded into the matrix of lipids/BTP.

In one embodiment of the method of delivering a neurotrophic factor to the brain of a subject of the present invention, the neurotrophic factor includes one or more of GDNF, BDNF, neurotrophin, cerebral dopamine neurotrophic factor, mesencephalic and astrocyte-derived neurotrophic factor. In one aspect of this embodiment, the neurotrophic factor is GDNF.

DETAILED DESCRIPTIONS OF THE INVENTION

Definitions

Figure 1:
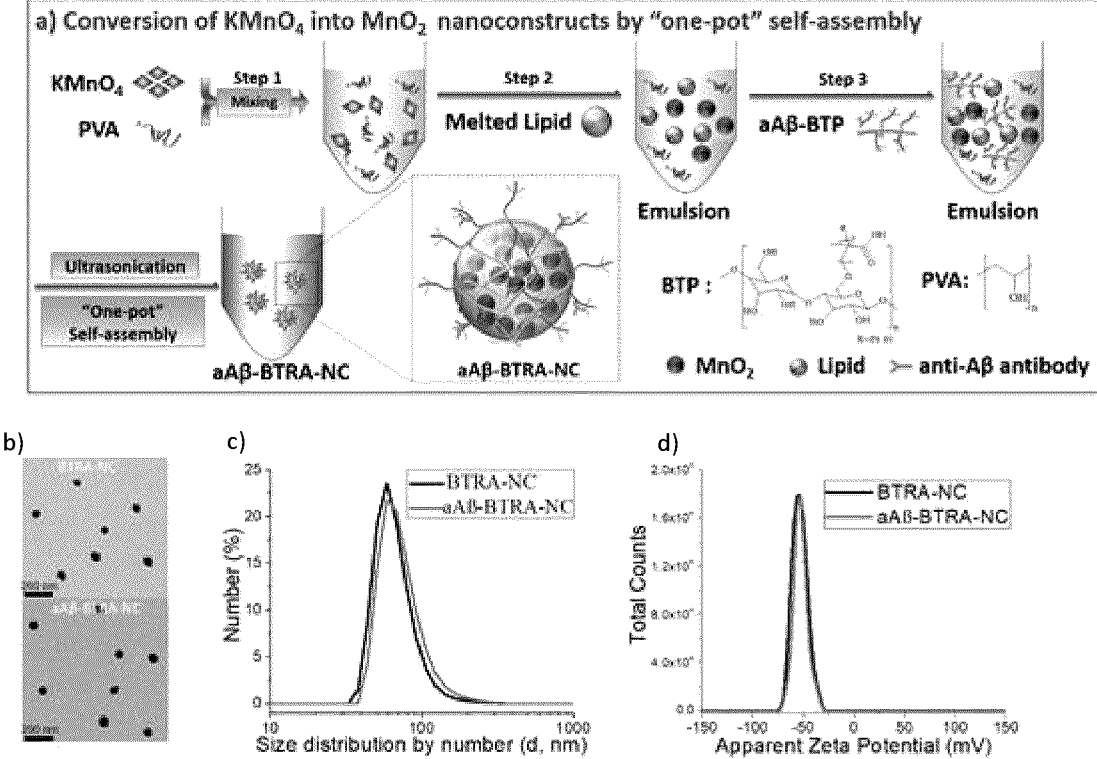
FIG. 1: shows a) Schematic diagram depicting the process of conversion of $KMnO_4$ into $MnO_2$-containing nanoconstruct by self-assembly using BTP and lipids, b) TEM images and relaxivity (r1) of NCs, c) Number based particle size distribution (~66-69 nm) and d) Zeta potential distribution of BTRA-NCs (~−50 mV) and aAβ-BTRA-NCs (~−49 mV).

In this specification and in the claims that follow, reference will be made to a number of terms that shall be defined to have the meanings below. All numerical designations, e.g., dimensions and weight, including ranges, are approximations that typically may be varied (+) or (−) by increments of 0.1, 1.0, or 10.0, as appropriate. All numerical designations may be understood as preceded by the term "about".

Throughout this specification and the claims, the terms "comprise," "comprises," and "comprising" are used in a non-exclusive sense, except where the context requires otherwise. Likewise, the terms "include", "has" and their grammatical variants are intended to be non-limiting, such that recitation of items in a list is not to the exclusion of other like items that can be substituted or added to the listed items. "Consisting essentially of" when used to define systems, compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers. "Consisting of" shall mean excluding more than trace elements of other ingredients and substantial method steps for using the multifunctional nanoparticles of the present disclosure. Embodiments defined by each of these transition terms are within the scope of this invention.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range.

The term "about," particularly in reference to a given quantity, is meant to encompass deviations of plus or minus five percent.

As used herein, "treating" or "treatment" of a disease in a subject (a human or non-human animal) refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Treatments containing the disclosed compositions and methods can be first line, second line, third line, fourth line, fifth line therapy and are intended to be used as a sole therapy or in combination with other appropriate therapies. In one aspect, the term "treatment" or "treating" excludes prevention or prophylaxis.

"Effective amount" refers to an amount of the composition that is capable of producing a medically desirable result in a treated subject. The methods of the present disclosure may be performed alone or in combination with other drugs or therapies.

"Pharmaceutically acceptable" refers to molecular entities and other ingredients of such compositions that are physiologically tolerable and do not typically produce unwanted reactions when administered to a subject.

The present invention relates to multifunctional nanoparticle formulations and methods of using the formulations for the treatment and/or diagnosis of central nerve system (CNS) diseases. The present invention also relates to the use of the multifunctional nanoparticles in the manufacturing of medicaments for the treatment and/or diagnosis of central nerve system (CNS) diseases.

As such, in one embodiment, the present invention provides for a brain-targeted (BT) and ROS-activable nanoconstructs (BTRA-NC), the BTRA-NC comprising a metal oxide nanoparticle embedded in a matrix of lipids/brain targeted polymer (BTP), the BTRA-NC being configured to facilitate blood brain barrier (BBB) penetration and accumulation of the NC in a disease area of the central nervous system (CNS).

In this disclosure, a novel theranostic nanoparticle-based system is developed to reduce ROS and oxidative stress and effectively detect the CNS disease area, including a neurodegenerative disease progression. The proof-of-concept studies are performed in an Alzheimer's disease model. However, the system of the present invention is a theranostic agent for other neurodegenerative disorders such as stroke, brain viral infections and chemobrain.

The present disclosure demonstrates the specificity and reactivity of metal oxide nanoparticles, such as $MnO_2$ nanoparticles (MDNPs) towards endogenous $H_2O_2$ and developed a BBB crossing theranostic system that improves early detection as well as plays an important role to rescue neuron from the oxidative stress by changing the neuroinflammatory microenvironment. The theranostic system of the present disclosure exhibits simultaneous effects on the neurodegenerative disease microenvironment such as: (1) reduction of ROS levels due to consumption of endogenous $H_2O_2$ produced at the disease site, (2) reduction of hypoxia by generating measurable amounts of $O_2$ in situ, and (3) reduction of acidosis by consuming protons during the reaction.

The term "metal oxide nanoparticle" as used herein refers to a particle comprising a solid core of an inorganic metal oxide material comprising at least partially ordered three-dimensional array of metallic cations and oxide anions. The nanoparticle size desired by this disclosure can vary widely, and essentially any particle size in the nanoparticle size range (e.g., below 1,000 nm, i.e. 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 990 nm and any number or range there in between) can be used. The shape of the nanoparticles may be regular (column, cube, cylinder, pillar, pyramid, rod, sphere, tube, wire, flake, disk, etc.) or irregular/random, which for example can be controlled by adjusting the reaction dynamics and aging/ripening time.

There are no limitations on the base metal of the metal oxide nanoparticles for this disclosure that reduce ROS levels due to consumption of endogenous $H_2O_2$ at the production site behind the BBB. For example, the base metal may be one or more selected from Cu, Sn, Ti, V, Cr, Mn, Co, Fe, Ni, Zn, Al, Y, Zr, Mo, In, Mg, La, Ce, Nd, Sm, Eu, Gd, Si, Ge, Pb, Ag, Tl, Cs, Hf, and Bi. In certain applications, the base metal may be one or more selected from V, Cr, Mn, Co, Y, Zr, Mo, In, Mg, La, Ce, Nd, Sm, Eu, Gd, Ge, and Bi. In certain applications, the base metal may be one or more selected from V, Cr, Mn, Mo, and Co. In certain applications, the base metal may be one or more selected from V, Cr, Mn, Fe, and Co. In certain applications, the base metal may be one or more selected from Ti, Ag, and Mn. In a specific embodiment of the present disclosure, the base metal is Mn.

There are no limitations on the chemical composition of the metal oxide nanoparticles for this disclosure as well. For example, some suitable metal oxide nanoparticles have a well-defined chemical composition (e.g., stoichiometric metal oxides having a well-defined composition, such as $MnO_2$), while some "non-stoichiometric" metallic oxides have variable proportions of mixtures of the metal cations, such as for example $BaTi_{0.8}Zr_{0.2}O_3$ or those with metal and/or oxygen ion vacancies. In certain applications, the metal oxide nanoparticle may be one or more selected from $Al_2O_3$, $TiO_2$, $ZrO_2$, $MgO$, $NiO_2$, $Co_3O_4$, $AgO$, $CuO$, $BiO$, $Rb_2O$, $In_2O_3$, $Tl_2O_3$, $Cs_2O$, and $HfO_2$. In certain applications, the metal oxide nanoparticle may be one or more selected from $MnO_2$, $Mn_2O_3$, $Mn_2O_7$, $MnOOH$, $Mn_3O_4$, and $Mn(C_2O_4)$. In a specific embodiment of the present disclosure, the metal oxide nanoparticle is $MnO_2$ (MD NP).

In this disclosure a BBB-crossing nanoparticle carrier system is developed by combining the metal oxide nanoparticles, lipids and brain targeting polymer matrix. The carrier system is functionalized with a moiety to specifically target a site in the brain behind the BBB, for example, in one embodiment, the moiety is an Aβ peptide to specifically target the AD site in the brain. This novel nanoparticle system once shuttled to the brain, in particular to the inflammatory regions of neurodegenerative disease, the loaded metal oxide nanoparticles, such as MD NPs will react with ROS ($H_2O_2$) converting to soluble $Mn^{2+}$ ions. The production of paramagnetic $Mn^{2+}$ ions can help to improve the MRI contrast in brain area that helps an early detection of the disease. Meanwhile, the reaction helps to remove $H_2O_2$ (ROS that will help to lower the oxidative stress) and protons (that will result in pH increase) and generate $O_2$ locally (reduce hypoxia at the disease site). These multiple effects of nanoparticle treatment produce biological effects at the disease site. As a result, the treatment improves the local conditions and promotes neural survival. Notably, the ability of MDNPs of the present disclosure to reduce the acidosis is used for the treatment of AD. The Aβ peptide forms the large and complex fibrils much more efficiently at acidic environment rather than natural pH [61]. Research has shown a significant apoptotic death of PC12 cells at pH 5.8, due to the aggregation of Aβ peptide [61]. The nanoparticle treatment together with changes in local condition will also help to inhibit the Aβ aggregation, which will benefit the AD patient.

In embodiments, the BBB crossing nanoparticle carrier system of the present invention is a hybrid matrix system. The matrix can contain one or multiple components. As used herein, "matrix" refers to an essentially two and/or three-dimensional environment capable of immobilizing, by embedding, entrapping or encapsulating one or multiple nanoparticles for the purpose of supporting the functionality of the nanoparticle. The interactions between the constituents of the matrix include, but are not limited to, covalent, ionic, electrostatic, hydrogen bonding, affinity binding, hydrophobic, and van der Waals interactions and combinations thereof.

Various materials can be used for forming a matrix, for example, without limitations, organic groups, organic compounds, inorganic compounds, polymers, organometallic compounds, surfactants, biological organic material (such as amino acids, proteins, lipids, DNA, enzymes, etc.), and the mixtures thereof. The matrix may also comprise hydrogel polymers, such as polysaccharides including agarose, dextran, carrageenan, alginic acid, starch, cellulose, or derivatives thereof.

The matrix can provide a structure to retain the one or multiple nanoparticulate in a desired distribution without interfering with proper functioning of the nanoparticles in the application. Alternatively, the matrix may itself also provide some function for the application. The matrix may, for example, have a function that is different than that of the nanoparticles, have a function that compliments that of the nanoparticles, or have a function that is the same as that of the nanoparticles. As yet another example, the matrix may be selected for its surface modifying properties to beneficially modify the nanoparticles in a way that is useful in some subsequent processing or use of the nanoparticles.

The system of multifunctional nanoparticles of the present disclosure provides a paradigm-shifting novel treatment combo that can reduce hypoxia and its down streams genes HIF-1α and BACE1 that will help to prevent Aβ generation and aggregation. Moreover, the novel system will reduce oxidative stress and acidosis and their detrimental effects on neuronal death [29-39] and promote neuronal survival and regeneration. The system also provides a ROS-responsive and Aβ-targeted MRI contrast enhancement that will be helpful for non-invasive detection of early onset and progression of AD.

The novel system of the present invention can also be applied to other types of neurodegenerative diseases such as PD, ALS, HD, stroke, multiple sclerosis and FRDA, where oxidative stress and inflammation plays an important role in disease progression. The novel bio-compatible carrier system of this disclosure is useful in preparing pharmaceutically acceptable compositions or formulations of MDNPs for the treatment of CNS related diseases, stroke, chemobrain, neuroinflammation and so forth. In addition, the current nanoparticle-based carrier system has chemically active groups those can be easily functionalized with different neurodegenerative disease specific protein, peptides, and molecules to specifically target the disease site in brain as describe in the examples below.

The pharmaceutical compositions may be prepared by mixing a therapeutically effective amount of the multifunctional nanoparticles of the present disclosure, and, optionally other active substance, with a pharmaceutically acceptable carrier. The carrier may have different forms, depending on the route of administration. In one embodiment, the carrier or acceptable vehicle is aqueous media with biocompatible and hemocompatible ionic strength, osmolarity and pH, such as aqueous solution of 0.9% NCl, or 4% dextrose at pH 6-7.4.

The multifunctional nanoparticles of the present disclosure may be administered to subjects through infusion or injection (for example, intravenous, intrathecal, intramuscular, intraluminal, intratracheal, intraperitoneal, or subcutaneous), orally, transdermally, or other methods known in the art.

In another embodiment, the present invention is a method for the synthesis of pharmaceutically acceptable multifunctional and colloidally stable bioinorganic multifunctional theranostic nanoconstruct (NCs) composed of bioreactive $MnO_2$ nanoparticles (MDNPs) loaded into a biocompatible polymeric and/or lipidic matrix such as polyelectrolyte-lipid or polyvinyl alcohol/lipid complex, graft terpolymer or poly(methacrylic acid)-polysorbate 80-starch (Terpolymer) and fatty acids. The lipid can be selected from range of fatty acid, or different phospholipids. The MD NPs showed reactivity towards the endogenous reactive oxygen species (ROS) such as $H_2O_2$. The MD NPs loaded NCs are activated by endogenous reactive oxygen species (ROS) and enhancing magnetic resonance (MR) contrast signals in CNS disease-affected areas. The NCs exhibits superior performance in detecting cerebrospinal fluid (CSF) pathology in CNS diseased mouse model by MR imaging. Intravenously injected NCs significantly amplify T1-weighted MR signals in the CSF by 1.51-2.24 fold, nearly proportional to cerebral concentrations of ROS. The NC-enhanced CSF MR signals demonstrate high detection sensitivity (about 88.9%) and specificity (100%) even at early-CNS diseased animal. This reaction of NCs with ROS produces $O_2$, which helps to attenuate microenvironmental hypoxia and thus prevents hypoxia-induced gene transcriptions and metabolic events harmful to neurons. The NCs showed reactivity towards ROS and significantly reduced the ROS on the disease brain and has protected primary cortical neurons from oxidative stress as observed in the in vitro study. The ROS quenching ability was confirmed through in vivo studies where NCs treatment showed significant disease in cerebral ROS and IL-1β levels in CNS diseased mice by 36%-83%.

The high reactivity and specificity of metal oxide nanoparticles, particularly, manganese dioxide nanoparticles (MDNPs), towards the ROS that is in higher level in the inflammatory regions of the diseased brain. The reaction of MDNPs results in the decrease level of the ROS at the brain.

The NCs of the present invention have several advantages owing to their multiple functionality and selective reactivity. First, they can effectively cross the BBB carrying a cargo, MDNPs, to inflammatory regions of the brain via acquired low density lipoprotein receptor (LDLR) targeting in situ. The delivery of the NCs to the diseased region can be further improved through their functionalization with targeting moieties specific to different CNS diseases. Second, the encapsulated MD NPs catalyzes the decomposition of $H_2O_2$ or directly reacts with excess $H_2O_2$ in the diseased tissue, reducing the ROS ($H_2O_2$) and its associated toxicity and pro-inflammatory cytokines. The advantage of this is that the reactive component is as needed and thus is not subject to degradation or metabolism en route. Third, these decomposition reactions produce $O_2$, attenuating microenvironmental hypoxia and thus preventing hypoxia-induced gene transcriptions and metabolic events harmful to neurons; in contrast to the mechanism of the majority of anti-oxidants/anti-inflammatory drugs. Thus, this agent delivers a unique combination of supportive mechanisms distinct from the agents mentioned.

Figure 18:
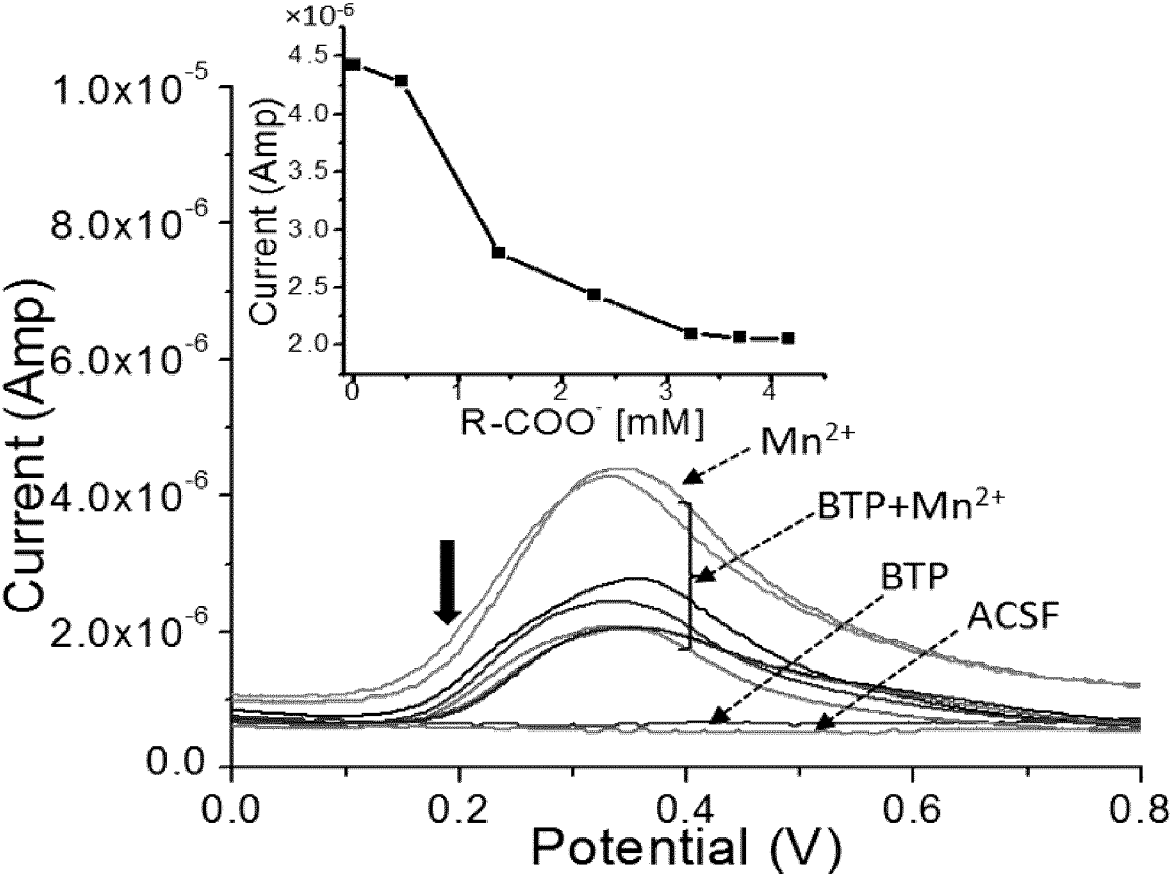
FIG. 18: shows differential pulse voltammetry (DPV) showing the signal decrease observed after titration of BTP into $Mn^{2+}$ in artificial cerebrospinal fluid (ACSF). The inset curve shows the dependence of current on $Mn^{2+}$ versus [R—COO—]. The current of the $MnCl_2$ solution (0.8 mM $Mn^{2+}$) in artificial cerebrospinal fluid (ACSF) decreased by 2-fold when titrated with a BTP solution (0-0.9 mg $mL^{-1}$, equivalent to 0-4.2 mM [R—COO—]). The binding between BTP and $Mn^{2+}$ can reduce free $Mn^{2+}$ levels in the brain and CSF, diminishing the toxic effect of this agent, and consistent with previously published data.

The MDNPs of this invention have dual functions as both catalyst and reactant. In the latter case, MDNPs are decomposed to harmless, water-soluble $Mn^{2+}$ ions, avoiding the in vivo accumulation of the metal oxide commonly observed for other metal-based contrast agents. In the present NCS the small MDNPs particles are loaded in terpolymer/lipid complex that make system quite different from other metal-based MRI contrast agents, where metals ions are trapped in a chelating agent. The main drawback of metal chelating agents is leaking of metal ions after their systemic administration leaving high concentration of free metals ions in the body [62]. In the NCs of this disclosure MDNPs are successfully loaded in the core of biocompatible and pharmaceutically acceptable terpolymer and lipid nano-carrier system. The nano-carrier system strongly holds the loaded MDNPs particle in the core, due to electrostatic and hydrophobic/hydrophilic interactions between terpolymer, lipid, and MDNPs. The results confirmed that NCs effectively cross the BBB, react with or break down by endogenous $H_2O_2$ to produce $O_2$, and paramagnetic $Mn^{2+}$ in situ. The binding ability of terpolymer with $Mn^{2+}$ ion was also confirmed through the pulse voltammetry (FIG. 18). The binding interaction reduces the free $Mn^{2+}$ ions inside the body, diminishing the toxic effect of NCs.

In another embodiment, the NCs of this invention serve as Mn based MRI contrast agent. Mn is a naturally occurring essential element found in the human body and an essential nutrient for intracellular activities, and small intake of Mn is required for vital bodily functions. Excess amount of Mn is cleared from the body through its natural mechanism that makes these NCs a clinically acceptable agent.

In one aspect, the present invention provides multifunctional NCs compositions for the early detection and treatment of CNS disease. Specifically, the multifunctional NCs composition comprises a metal oxide nanoparticle; a functional coating on the surface of the metal oxide nanoparticle; and a pharmaceutically acceptable vehicle that is composed of lipid, phospholipids, terpolymer, surfactants and targeting moieties those can be proteins, peptides or any molecules that can be used to target the disease site.

NCs are synthesized using the oil-in-water emulsion method, whereas the sonication is used to obtain homogeneous NCs suspension. The synthesis method can be scaled up by using the high-pressure homogenizer to produce homogeneous NCs suspension or large volumes.

The following points or criteria were considered during the formulation development to make NCs clinically acceptable: (1) low toxicity; (2) good colloidal stability under physiological conditions; (3) proper blood circulation and half-life of the nanoparticles; (4) enhanced BBB penetration and disease site retention; (5) tailorable kinetics of the nanoparticles reaction towards $H_2O_2$. The inventors have found that these criteria can be achieved by optimizing the ratio of terpolymer/lipids, lipids/metal oxide precursor nanoparticles, selecting different kinds of surfactants, and using different biomarker-targeting moieties-functionalized terpolymer.

The NCs can be further functionalized by coating the surface by biocompatible materials. For example, biocompatible coating materials include, but are not limited to, synthetic and biological polymers, copolymers and polymer blends, and inorganic materials. Polymer materials may include various combinations of polymers of acrylates, siloxanes, styrenes, acetates, alkylene glycols, alkylenes, alkylene oxides, parylenes, lactic acid, and glycolic acid. Further suitable coating materials include a hydrogel polymer, a histidine containing polymer, and a combination of a hydrogel polymer and a histidine-containing polymer. Coating materials may also include combinations of biological materials such as a polysaccharide, a polyaminoacid, a protein, a lipid, a nucleic acid, a glycerol, and a fatty acid.

Other biological materials for use as a coating material could be heparin, heparin sulfate, chondroitin sulfate, chitin, chitosan, cellulose, dextran, alginate, starch, carbohydrate, and glycosaminoglycan. Proteins may include an extracellular matrix protein, proteoglycan, glycoprotein, albumin, peptide, and gelatin. These materials may also be used in combination with any suitable synthetic polymer material.

The coating material can also be a targeting moiety, including a brain targeted polymer (BTP). The term "targeting moiety" can refer to a molecule or molecules that are able to bind to and complex with a target biomarker or biomarker of interest. The term can also refer to a functional group that serves to target or direct NCs to a particular location, cell type, diseased tissue, or association. In general, a "targeting moiety" can be directed against a biomarker of interest ("target biomarker").

It was found that NCs are in nanometer to submicron size with negative surface charge and nearly spherical shape. The negative surface charge can prolong the blood circulation time of the nanoparticles. For BBB penetration the particle size is in the range of about 20 about 200 nm, preferably from about 40 to about 160 nm, and most preferably from about 40 to about 100 nm.

The NCs of the present invention are stable under physiological condition up to 48 hours. No change is particle size and polydispersity index (PDI) was seen up to 48 hours.

The NCs of the present invention are able to generate $O_2$ following reaction with $H_2O_2$. The in vitro study provided in this disclosure confirmed that NCs are able to generate $O_2$ up to 60 min following reaction with $H_2O_2$.

The NCs are an MRI contrast agent. The in vitro MRI results provided in this disclosure showed 5.6-5.7-fold increase in T1 relaxivity (r1) in the presence of $H_2O_2$ due to the conversion of loaded MD NPs to paramagnetic $Mn^{2+}$.

No impact of synthesis conditions was observed on the targeting moieties. This is very important observation for NCs formulation, especially when protein, peptides and biological molecules are used as a targeting moiety to target the disease site. Through the use of circular dichroism (CD) inventor found that the secondary structure of antibody (such as 4G8 that is used in the present example) was preserved after chemical conjugation with terpolymer and exposure to conditions used for the NCs synthesis. That makes the NCs of this disclosure a suitable carrier system for targeted drug delivery.

The targeting ability of NCs of the present invention was confirmed in vitro. As shown in the examples, the 4G8 antibody functionalized NCs can successfully bind to the 4G8 peptide. In vitro test showed that more than 10-fold of 4G8 peptide removed from the medium by 4G8 antibody functionalized NCs than the non-targeted NCs.

The brain targeting ability of NCs of this disclosure is also confirmed in vivo. In one example 4G8 functionalized NCs are able to successfully reach the Aβ-plaque area of Alzheimer disease animal brain. The amount of antibody functionalized NCs was much higher than non-targeted NCs as confirmed through fluorescence and transmission electron microscope analysis. The results were also confirmed through immunohistochemistry staining of Aβ-plaques in Tg brain sections.

The novel theragnostic NCs disclosed herein are able to cross the BBB as confirmed through the in vitro 3D BBB model. Results confirmed the permeation of NCs with more than 10% of the administered dose crossed the BBB after 30 min.

The NCs of the present invention deliver non permeable BBB dye into the brain of healthy animals thereby confirming that the carrier system of this disclosure can cross the intact BBB. This result is very important since the BBB is intact at the early stage of disease and most of the therapeutic and diagnostic agents are not able to penetrate the intact BBB. This result confirms the novelty of these NCs those can be used as a vehicle to deliver different molecules to the brain.

In another embodiment the NCs of the present invention include a therapeutic agent embedded into the matrix and BTP. The therapeutic agent includes one or more of a nucleic acid, a peptide, a therapeutic antibody, a small molecule modifiers of programmed cell death (PCD), a neurotrophic factor, a growth factor, an immunosuppressive agent, an anti-inflammatory agent, an anti-apoptotic agent, a cytokine inhibitor, a metabolism modulator, a vascular modulator, and/or a cell proliferation inhibitor.

The NCs of this invention can be further functionalized with different receptor targeting. The endothelial cells of BBB have different receptors to transport biological molecules including growth factors, enzymes and plasma proteins inside brain parenchyma. Thus, receptor mediated transcytosis (RMT) strategies can be applied to the NCs. The BTP of NC can be functionalized with different targeting moieties such as insulin to target insulin receptor, transferrin to target transferrin receptor, leptin to target leptin receptor, arginine vasopressin to target vasopressinergic receptor, Aβ, APOE2, APOE3, APOE-Aβ complexes to target lipoprotein receptors such as LRP-2, Aβ to target receptor for advanced glycation end (RAGE), amino acids to enter brain through amino acid receptor (LAT), and glucose to target Glut-1 and Glut-3 transporters.

The BTP of NCs can be functionalized with different antibodies, including therapeutic antibodies, to target neurodegenerative diseases.

The BTP of the NCs of this disclosure can be functionalized with different antibodies (including therapeutic antibodies) and aptamers to target AD. Non-limiting examples of such antibodies include antibodies binding to amyloid precursor protein (APP): 6E10, 4G8, 22C11, 82E1, mouse monoclonal antibody (MOAB-2, IgG2b), APP polyclonal antibody (recombinant human amyloid beta A4 protein (18-270AA)), rabbit polyclonal antibody for APP (MBS150418), purified (azide-free) anti-APP (800904), and anti-APP A4 antibody, a.a. 66-81 of APP [NT], clone 22C1. For anti-amyloid therapy: BACE inhibitor: Verubecestat, Atabecestat, Lanabecestat, E2609 (elenbecestat), and anti-BACE Antibody, CT, clone 61-3E7. Anti-Aβ monoclonal antibody: Bapineuzumab, Solanezumab, Aducanumab, GSK933776, Crenezumab, Ponezumab, and Gantenerumab. Non anti-amyloid therapy: GV-971 (sodium oligo-mannuronate) can bind to multiple sites of amyloid, further destabilize and inhibit Aβ aggregation, and then increases Aβ clearance.

The BTP of current NCs can be functionalized with different antibodies (including therapeutic antibodies) and aptamers to target PD. Non-limiting examples of such antibodies include antibodies targeting the alpha-Synuclein: murine monoclonal antibody 9E4, AB274, mAb47, mAB47, 1H7, 5C1, AB1, AB2, BIIB054, Syn303, Syn-O1 Syn-O4, and Syn-F1, aSyn-323.1, aSyn-336.1 and aSyn-338.1, MEDI1341, and antibodies against lymphocyte-activation gene 3 (LAG3). Antibodies against the progressive supranuclear palsy (PSP): monoclonal anti-Tau antibody UCB0107, BMS-198168/BIIB092 and C2N-8E12/ABBV-8E12.

In another embodiment, the BTP of current NCs can be functionalized with different antibodies (including therapeutic antibodies) and aptamers to target ALS. Non-limiting examples of such antibodies include recombinant human monoclonal antibody (a-miSOD1), single-chain variable fragment (scFv) derived from the 3B12A monoclonal antibody, scFv antibody VH7Vk9.

The BTP of current NCs can be functionalized with different antibodies (including therapeutic antibodies) and aptamers to target HD. Non-limiting examples of such antibodies include anti-mutant huntingtin protein (mHtt) antibodies: single-chain Fv fragment (scFv)-MW1 and MW2, scFv-MW7, scFv-C4, scFv-C4-PEST, VL12.3, scFV-6E, W20, Haap1, Haap3, and INT41. Anti-tau antibodies-INT41, anti-inflammatory antibody (anti-semaphorin 4D, VX15/2503-N-131 and brain-derived neurotrophic factor (BDNF) mimetics-laquinimod.

The BTP of current NCs can be functionalized with different targeting moieties to target the receptors in ischemic stroke. Non-limiting examples of such targeting moieties include chlorotoxin (CTX) peptide, anti-Integrin alpha 4 antibody (Natalizumab), anti-toll-like receptor 4 (TLR 4) antibody, anti-myelin-associated glycoprotein (MAG) antibody (GSK249320), anti-Nogo-A antibody (7B12), anti-oligo-myelin glycoprotein antibody, anti-GluN1 antibody.

The BTP of current NCs can be functionalized with different targeting moieties to target the receptors in FRDA. Non-limiting examples of such targeting moieties include anti-Frataxin antibody such as clone 4F9 antibody; N191/7; 18A5DB1; 17A11.

In a further embodiment, BTP of current NC can be conjugated with different antibodies (including therapeutic antibodies) and aptamers to target MS. Non-limiting examples of such antibodies include monoclonal antibody-Alemtuzumab, Elezanumab, GNbAC1, Natalizumab, Ocrelizumab, Ofatumumab, Opicinumab, Ublituximab, Rituximab, VAY736, Atacicept, Daclizumab, Muromonab, Secukinumab, Tabalumab, Ustekinumab, Vatelizumab, Interferon b-1b, Interferon b-1a, Interferon b-1a, and Peg interferon b-1a.

The BTP of NC can be functionalized with different antibodies (including therapeutic antibodies) and aptamers to target McLeod neuroacanthocytosis syndrome (MLS). Non-limiting examples of such antibodies include Alemtuzumab target CD52, Daclizumab IL-2 receptor, Natalizumab targets α4β1 Integrin, and Rituximab.

Figure 16:
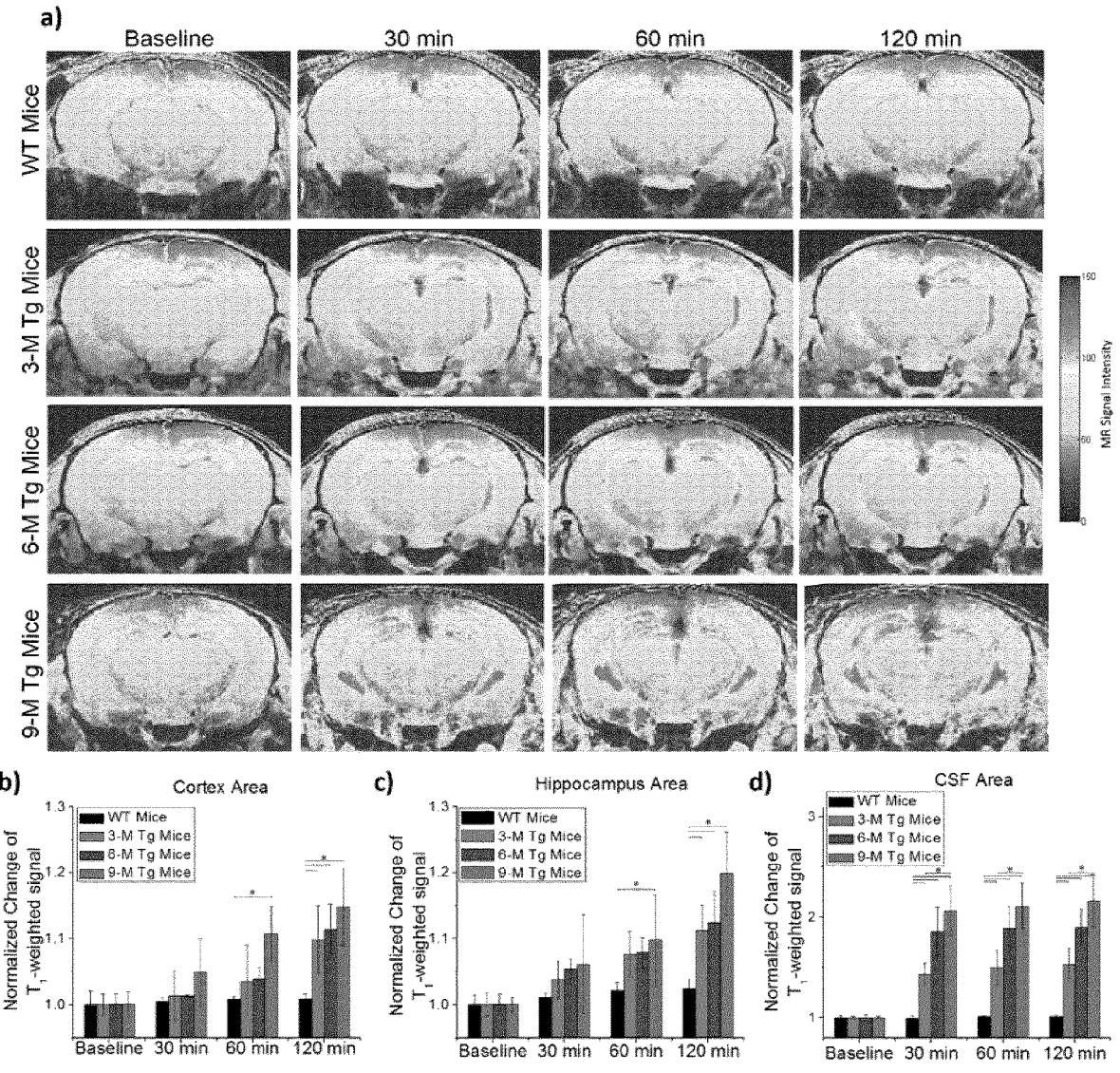
FIG. 16: shows a) In vivo T1-wt MRI brain images of WT mice (top panels) and different ages (3-, 6-, and 9-months) of Tg mice (subsequent panels) collected before and after aAβ-BTRA-NC (100 μmol Mn $kg^{-1}$ of bodyweight) i.v. injection, imaged at 30, 60 and 120 min using a 7 T MRI system. Normalized $T_1$-weighted signal enhancement in b) cortex, c) hippocampus, and d) CSF regions vs. time post i.v. injection of aAβ-BTRA-NC (100 μmmol Mn $kg^{-1}$ of bodyweight). *P<0.05 compared to WT mice. The data are presented as mean±standard deviation (n=8). WT: wild type; M: month.
Figure 17:
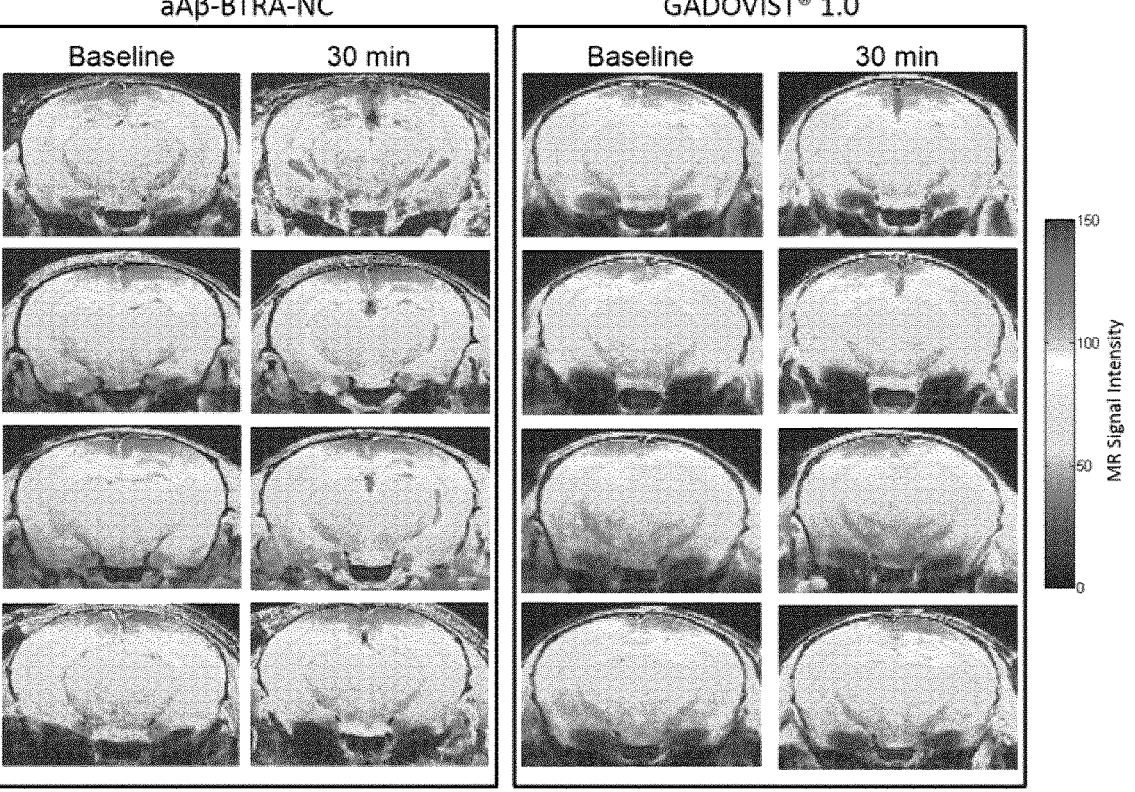
FIG. 17: shows comparison of in vivo $T_1$-weighted MRI brain images of different ages (3, 6, 9-month) of WT and TgCRND8 mice treated with i.v. injection of aAβ-BTRA-NCs (100 μmol Mn $kg^{-1}$ of body weight) or GADOVIST® 1.0 (clinical dose: 100 μmol Gd $kg^{-1}$ of body weight). Apparently, the Gd-based MR contrast agent GADOVIST® 1.0 hardly enhanced the MR signals, whereas aAβ-BTRA-NCs did at 30 min post i.v. injection. WT: wild type; M: month.

In one embodiment, this disclosure describes the application of novel NCs for early-stage detection of AD. aAβ-BTRA-NCs for non-invasive MRI detection of early stage and progression of AD was assessed using 3-, 6- or 9-month old Tg mice or age-matched wild-type (WT) littermates. MRI signals acquired as early as 30 min post aAβ-BTRA-NC injection confirms the significant enhancement of MR signals in CSF, cortex and hippocampus of Tg mice. Studies were performed prior to treatment (baseline) and at 30, 60 and 120 min after intravenous (i.v.) administration of aAβ-BTRA-NCs (FIG. 16). In contrast, the commercially available Gd-based contrast agent GADOVIST® 1.0 produced minimal signal enhancement at the same dose (FIG. 17).

In a further embodiment, the $T_1$-wt MR signals in the regions of cortex, hippocampus, and CSF were normalized against their own baselines and plotted as a function of mouse age and time post NC injection. The WT mice shows minor changes in the signals with time and age as compared to Tg mice at 3-months of age and increases with mouse age, indicating greater disease severity. In hematoxylin and eosin (H & E) stained brain sections with labeled Aβ plaques, the plaques could hardly be visualized in the 3-month-old Tg mouse brain, while their density profoundly increased at 6- and 9-months of age. This result is consistent with a previous report on age-dependent amyloid deposition in Tg mice that Aβ42 content increased ~70-fold from 115-728 ng/g of brain at 2.5 months to 12,476-29,260 ng/g of brain at 6.5 months of age [63]. Thus, the NCs of this disclosure demonstrate an ability to detect AD as early as 3 months of age in Tg mice.

In further investigation, the $T_1$-wt signal enhancement in the cortex and hippocampus area exhibits a strong dependence on the post NC-injection time, while the signal in the CSF is nearly independent of the time from 30 min to 120 min. The gradual increase in the signal in cortex and hippocampus areas may be due to slow penetration of NCs through the brain tissue and conversion of $MnO_2$ into $Mn^{2+}$ ions. In contrast, the rapid appearance of a strong signal in the CSF may suggest easier transport of NCs and greater availability of ROS and Aβ oligomers in the CSF compared to other areas.

(sensitivity 85.7%-88.9%; selectivity 77.8%-100%) and cortex (sensitivity 83.3%-87.5%; selectivity 70.0%-87.5%) increasing with mouse age. Once NCs reach inflammatory regions of brain, the reaction of ROS with NCs together with their metabolic degradation resulted in small polymer/lipid NCs fragments carrying $Mn^{2+}$ ions which could bound to soluble Aβ in CSF generating higher sensitivity and selectivity. These results indicate that non-invasive MRI of CSF pathology enabled by the novel aAβ-BTRA-NCs can detect definitive signs of an incipient early AD pro-inflammatory process(es) in living subjects.

TABLE 1

Diagnostic sensitivity and specificity by aAβ-BTRA-NC-enhanced MR signals for Tg mice (95% CI: 95% confidence interval).

| Area | Sensitivity % (95% CI) | | | Specificity % (95% CI) | | |
|---|---|---|---|---|---|---|
| | 3-M | 6-M | 9-M | 3-M | 6-M | 9-M |
| CSF | 88.9 | 88.9 | 88.9 | 100 | 100 | 100 |
| | (51.8-99.7) | (51.8-99.7) | (51.8-99.7) | (59.0-100) | (59.0-100) | (59.0-100) |
| Hippocampus | 85.7 | 85.7 | 88.9 | 77.8 | 77.8 | 100 |
| | (42.1-99.6) | (42.1-99.6) | (51.8-99.7) | (40.0-97.2) | (40.0-97.2) | (59.0-100) |
| Cortex | 83.3 | 87.5 | 87.5 | 70.0 | 87.5 | 87.5 |
| | (35.9-99.6) | (47.4-99.7) | (47.4-99.7) | (34.6-93.3) | (47.4-99.7) | (47.4-99.7) |

The binding ability of NCs component of the present invention was further assessed in vitro. Dissolved aAβ-BTP that can bind both Aβ oligomers through the antibody and $Mn^{2+}$ via poly(methacrylic acid) chains in the BTP, as confirmed by differential pulse voltammetry, magnifies the MRI signal in CSF where soluble Aβ oligomers exist. The dual binding affinity of aAβ-BTP can also reduce free $Mn^{2+}$ ions and soluble Aβ levels in the brain and CSF, diminishing their toxic effects [64].

Figure 15:
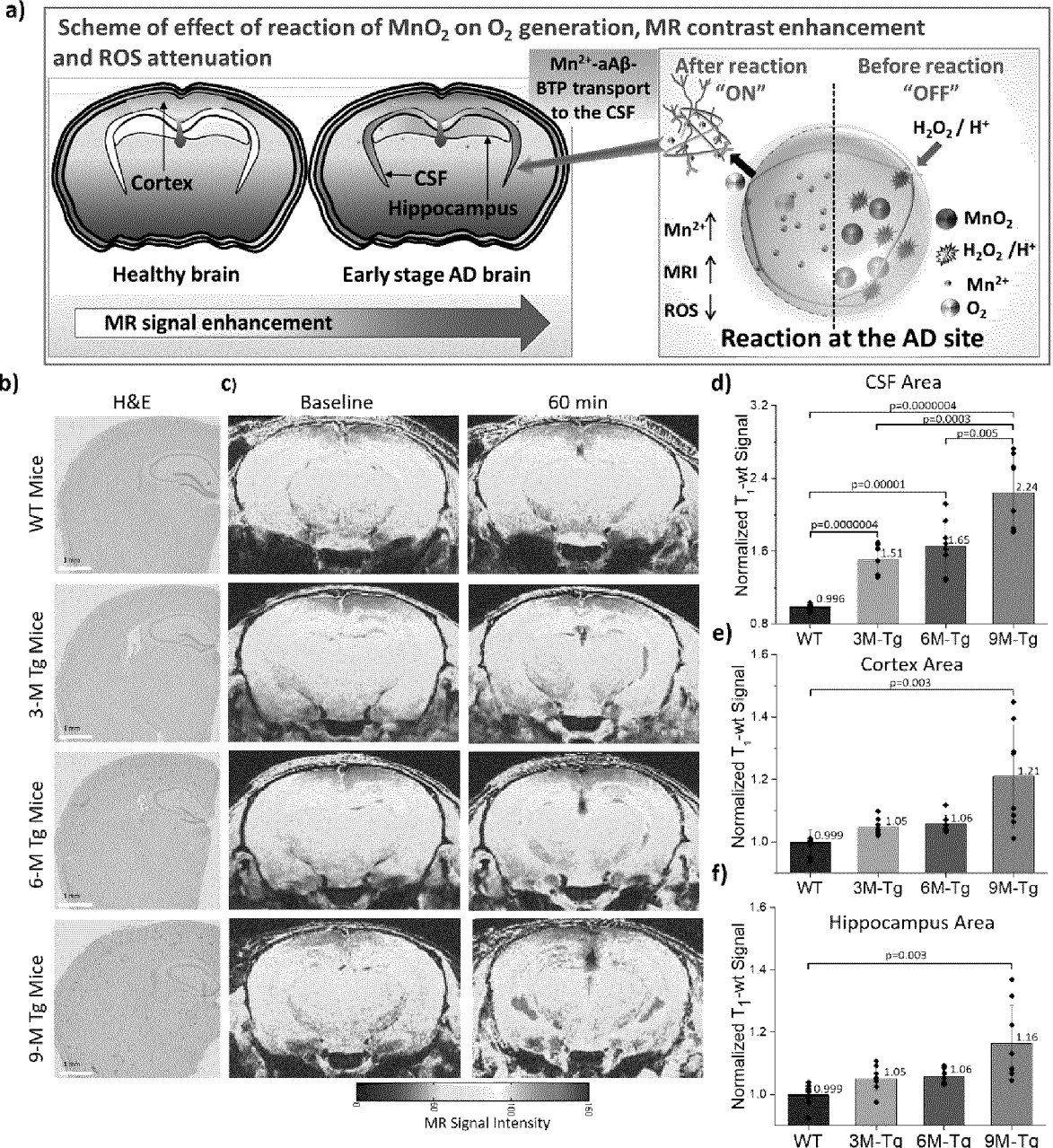
FIG. 15: shows a) Schematic showing the effect of $MnO_2$ carried by aAβ-BTRA-NCs on $O_2$ generation, MRI contrast enhancement and ROS attenuation. The aAβ-BTRA-NCs accumulate at Aβ plaque area and react with the ROS ($H_2O_2$), generating $Mn^{2+}$ ions locally. The multifunctional aAβ-BTP can bind with soluble $Mn^{2+}$ and Aβ oligomers in the CSF or transport them to CSF from other areas. b) H & E staining of typical brain sections of WT mice and Tg mice of different ages (3-, 6-, and 9-months). c) Representative in vivo T1-wt MR images of brains of WT mice and Tg mice of different ages acquired before (baseline) or 60 min after aAβ-BTRA-NC treatment. d-f) $T_1$-wt MR signal enhancement relative to baseline in different brain regions at 60 min post-injection (d: CSF, e: cortex, f: hippocampus regions) for Tg mice at different ages. WT littermates at different ages were combined into one group due to the minimal and similar MR contrast enhancement after aAβ-BTRA-NC treatment. Data are presented as mean±SD (n=8). P values indicate statistically significant difference between aAβ-BTRA-NCs treated groups (c-e). WT: wild type; M: month.

The clinical application of the NCs of the present invention is further evaluated using MRI studies in vivo (FIG. 15). To balance the cost of imaging preparation time and sufficient MRI signal enhancement, images acquired 60 min after injection of aAβ-BTRA-NCs is selected for further analysis (FIG. 15c). The normalized $T_1$-wt signal enhancement in CSF shows strongest enhancements among three investigated areas, increasing >1.5-fold (1.51, 1.65, and 2.24 for 3-, 6- and 9-months of age, respectively) from the baseline (FIG. 15d), while only 1.05-1.16/1.21-fold increases is observed in hippocampus (FIG. 15f) and cortex areas (FIG. 15e). The enhanced signals in the CSF for all age groups is significantly different from those in the WT mice ($p=1\times10^{-5}$–$4\times10^{-7}$); the differences are statistically significant between 6-months and 9-months of age ($p=0.005$) and between 3-months and 9-months of age ($p=0.0003$) (FIG. 15d). In contrast, statistically different signal enhancement in the cortex (FIG. 15e) and hippocampus (FIG. 15f) is only found between 9-month old Tg mice and WT mice ($p=0.003$). These results demonstrate that non-invasive MRI of CSF pathology enabled by aAβ-BTRA-NCs has the potential to determine different stages of AD pathology.

Figure 19:
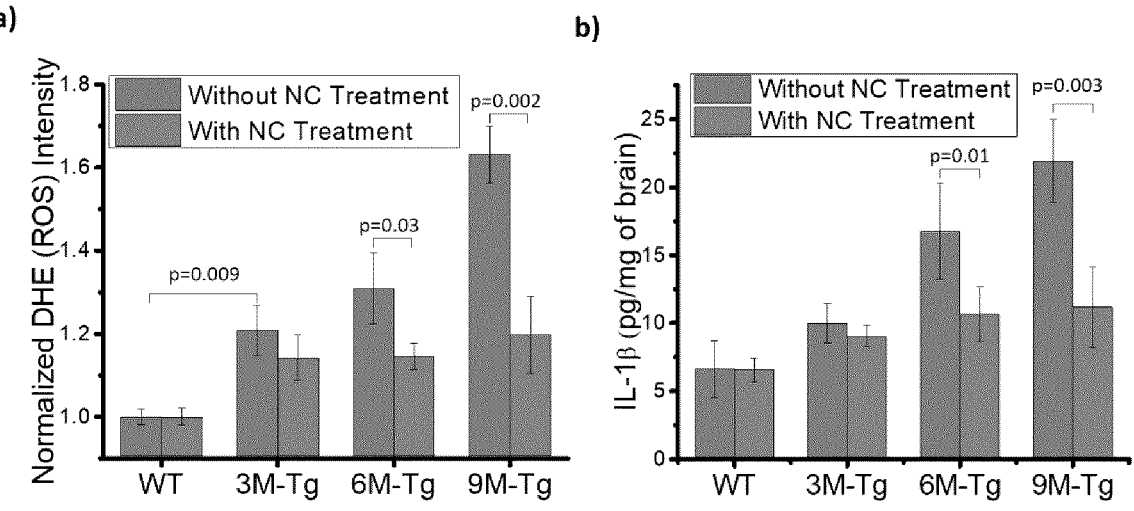
FIG. 19: shows a) ROS levels indicated by DHE (dihydroethidium) fluorescence intensity in the brains of WT mice and Tg mice of various ages without treatment or at 2 h post i.v. injection of aAβ-BTRA-NCs. b) Levels of pro-inflammatory cytokines IL-1β in the brains of WT and Tg mice of different ages without treatment or at 24 h post treatment. The data are presented as mean±SD (n=5). P values indicate statistically significant difference between aAβ-BTRA-NCs treated group and untreated group. WT: wild type; M: month.
Figure 21:
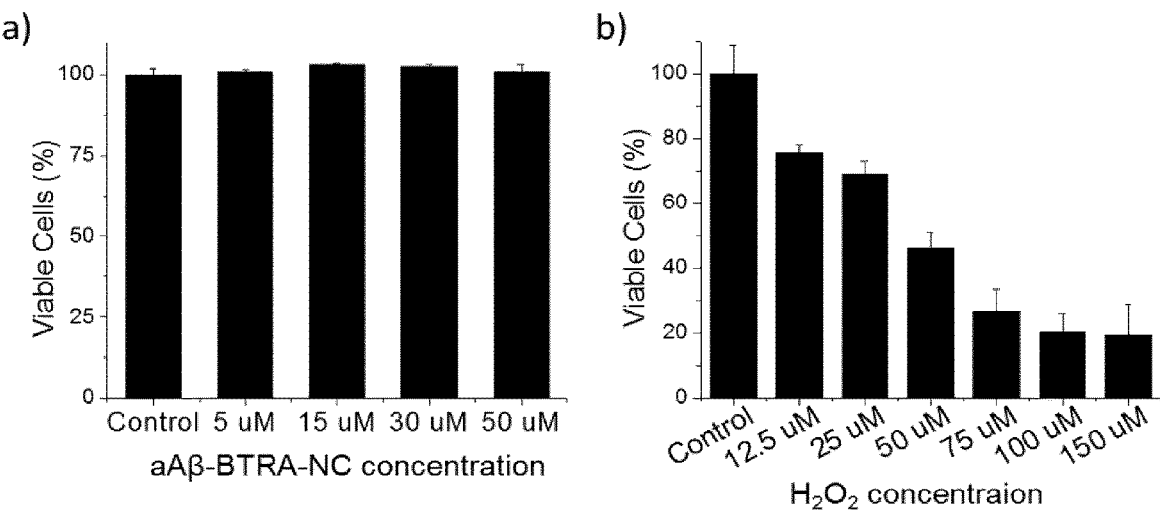
FIG. 21: shows effect of (a) aAβ-BTRA-NCs (5-50 μM) and (b) $H_2O_2$ (12.5-150 μM) on the cell viability of primary mouse neurons after incubation for 24 h. Primary mouse neurons were prepared from the ventral mesencephalon of mouse embryos at embryonic day 15. Cell viability was analyzed by MTT assay as expressed as a percentage of control MTT activity. The data are presented as mean±standard deviation (n=3).
Figure 22:
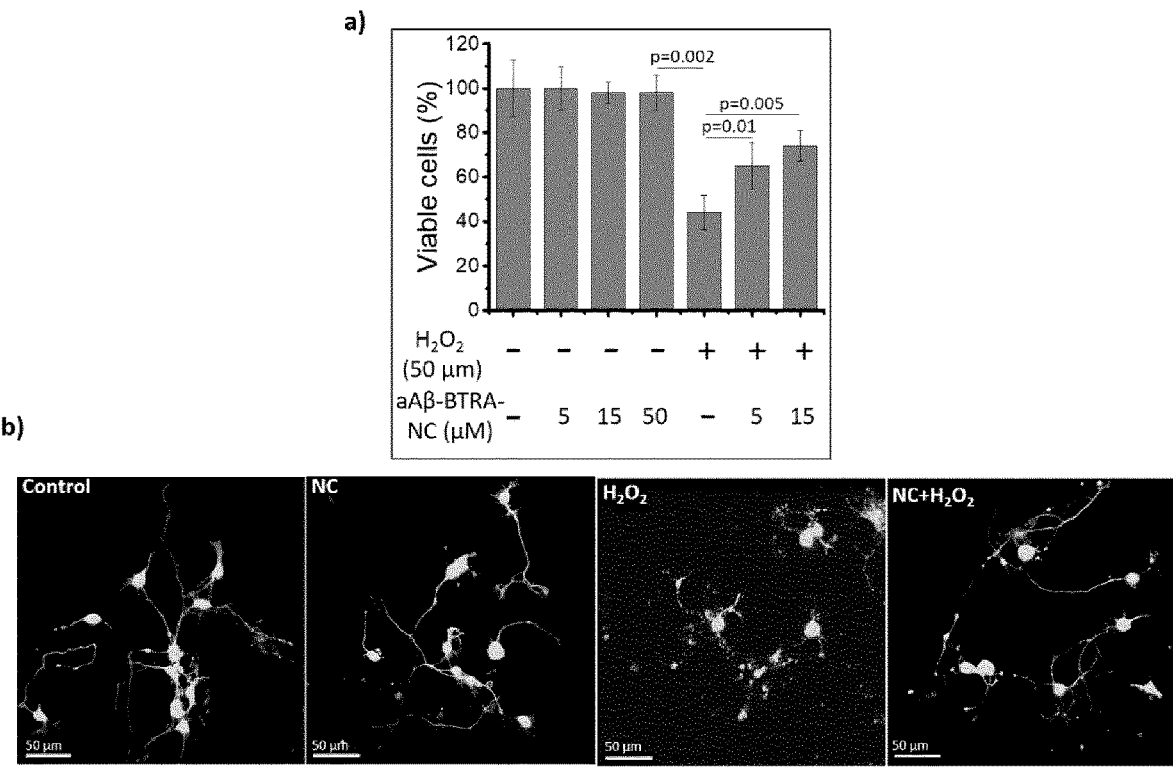
FIG. 22: shows a) Influence of aAβ-BTRA-NCs on viability of mouse cortical neurons with or without exposed to 50 mm $H_2O_2$. The data are presented as mean±SD (n=3). b) Representative CLSM images showing neuronal morphology in vitro treated by different groups. P values indicate statistically significant difference between aAβ-BTRA-NCs treated group and untreated group.

In a further embodiment, the diagnostic sensitivity and specificity is calculated and presented in Table 1. The data acquired at 60 min post injection is used to calculate diagnostic sensitivity (true positive rate) and specificity (true negative rate) [65]. The MR signal enhancement in CSF exhibits the highest diagnostic sensitivity (88.9%, 95% CI) in Tg mice and specificity (100%, 95% CI) in WT mice regardless of mouse age, followed by those in hippocampus The current invention further evaluates the potential of NCs in protection of cortical neurons from oxidative stress and suppression of oxidative stress. A dose-dependent cytotoxicity study using a mouse model indicates that aAβ-BTRA-NCs are non-toxic to primary cortical neurons up to 50 μM of Mn (FIG. 21a), while $H_2O_2$ significantly reduces cell viability (FIG. 21b). Introducing aAβ-BTRA-NCs (5 or 15 μM) to neurons treated with 50 μM $H_2O_2$ raised cell viability by 20% and 30%, respectively (FIG. 22a). CLSM shows that 15 μM aAβ-BTRA-NCs do not alter neuronal morphology, instead, protected the neurons from $H_2O_2$-induced neuronal damage (FIG. 22b). Total cerebral ROS levels before and after NC treatment in Tg and WT mice is also measured (FIG. 19a). The ROS level in untreated Tg mouse brains are 18.7%, 30% (1.3-fold) and 60% (1.6-fold) higher than those in the WT mice at 3-, 6- and 9-month of age, respectively. This result shows that higher cerebral ROS ($H_2O_2$) levels enhance MRI contrast with age by greater production of $Mn^{2+}$ ions in addition to leakier vessels at older ages. After aAβ-BTRA-NC treatment the cerebral ROS concentrations do not change in WT mice; however, they slightly decrease in 3-month old Tg mice and significantly decreased by 14.9% and 36.3% in 6- and 9-month old Tg mice, respectively. These results demonstrate that i.v. injected aAβ-BTRA-NCs selectively attenuate excess ROS; the higher the ROS level, the more profound the effect.

Figure 20:
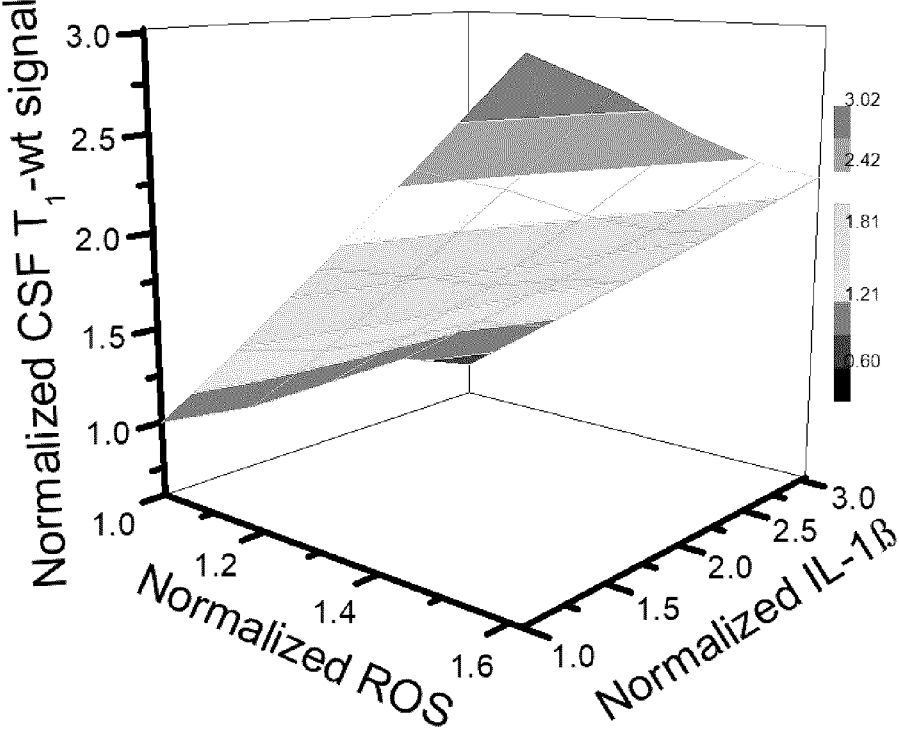
FIG. 20: shows a 3D surface plot of relationships among in vivo CSF MRI signal enhancement, ex vivo ROS and IL-1β concentrations in brain tissue. All measured values were normalized to WT mice group.

The use of the NCs of this disclosure in pro-inflammatory cytokine IL-1β levels are investigated using the whole Tg mice brain. The pro-inflammatory cytokine IL-1β levels shows a similar trend of ROS level in relation to mouse age and treatment response (FIG. 19b). While showing no effect in WT mice and slight effects in 3-month-old Tg mice, the aAβ-BTRA-NC treatment reduces cerebral IL-1β concentration by 55% and 83% in 6- and 9-month-old Tg mice, respectively. Interestingly, a 3D-surface plot of normalized CSF MR signals vs. ROS and IL-1β levels reveals nearly linear relationships (FIG. 20), suggesting a novel application of CSF MRI. Based on the MRI signal in the CSF, aAβ-BTRA-NCs are an effective and quick means for probing ROS and pro-inflammatory cytokine IL-1β level over the different stages of AD. The CSF MRI has the potential to link with clinical biomarkers for an enhanced diagnosis of AD.

Figure 23:
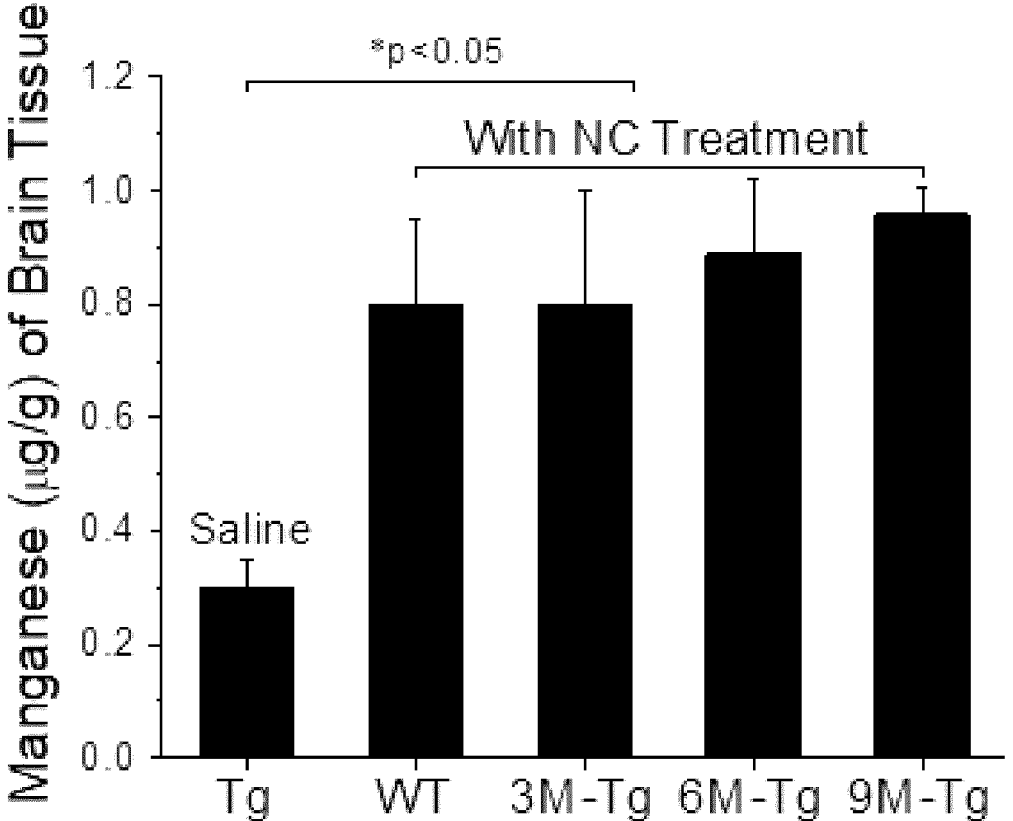
FIG. 23: shows the concentration of Mn in brain of different ages of WT mice and TgCRND8 mice at 2 h post aAβ-BTRA-NC injection (100 μmol Mn $kg^{-1}$ of body-weight) obtained using ICP-AES.*P<0.05 versus saline-treated TgCRND8 mice. The data is presented as mean±SD (n=5). M: month; WT: wild type

In another embodiment, the present NCs can be used to determine the manganese content in brain. Mouse brains (WT and Tg) of various ages were analyzed by inductive coupled plasma atomic emission spectroscopy (ICP-AES) 2 h after i.v. injection of aAβ-BTRA-NC. Results show that the WT and 3-month old Tg mice contained similar amounts of cerebral Mn, while the Tg mice at 6- and 9-months of ages shows slightly higher Mn contents (FIG. 23). The relative delivery efficiency of aAβ-BTRA-NCs into the brain of Tg mice, compared to the whole body, 2 h post injection is calculated to be 9.1%, 10.8% and 12.0% in 3-months, 6-months and 9-months old Tg mice, respectively. These results indicate that it is the redox-reaction produced $Mn^{2+}$ instead of total amount of Mn that amplified MR contrast.

The unique functionality of aAβ-BTRA-NCs to respond to ROS and bind with both AP and $Mn^{2+}$ gives MRI a useful application in detecting Aβ-induced oxidative stress and inflammation, an early event in AD.

The preliminary assessment of acute toxicity of novel NCs were also evaluated in ex vivo organs. The studies are conducted in 6-month old Tg mice treated with aAβ-BTRA-NCs (100 μmol Mn $kg^{-1}$ of bodyweight). No histological abnormalities in any of the major organs are observed at 7 days after the treatment as compared to saline controls. These results further demonstrates that there are reduced concerns about the potential toxicity of $MnO_2$-containing NCs and the production of $Mn^{2+}$ in possible translation to the clinic [66].

Formulation #1: MDNPs

The formulation #1 comprises MDNPs stabilized with polyvinyl alcohol (PVA) poly(allylamine hydrochloride) (PAH) or any charged polymers, molecules or proteins.

The formulation #1 can be prepared by direct mixing of $KMnO_4$ with PVA, PAH or other charged polymers. The reaction can be performed at room temperature or temperature up to 50° C. Thus, the MDNPs are coated with polyelectrolyte, polymer or charged molecules. In one example the formulation #1 (MDNPs) is obtained using PVA. The MDNPs have a diameter of about 20 nm to about 200 nm. Preferably, the nanoparticles of the formulation #1 have a diameter of about 20 nm, with a negative charge of about –30 mV.

Formulation #2: BTRA-NCs

The formulation #2 is a polymer-lipid based nanoparticle. The core of nanoparticles contains MD NPs. The formulation is obtained by making an oil-in-water emulsion of MDNPs, lipids and terpolymer. The lipid can be selected from wide range of fatty acid (such as oleic acid, myristic acid, ethyl arachidate, hexadecylamine, dodecylamine, caprylic acid, capric acid, lauric acid, stearic acid, arachidic acid, behenic acid, lignoceric acid, cerotic acid, erucic acid, palmitoleic acid, sapienic acid etc.). The lipid can also be selected from a range of phospholipids (such as 1,2-Didecanoyl-sn-glycero-3-phosphocholine, 1,2-Dierucoyl-sn-glycero-3-phosphate (Sodium Salt), 1,2-Dierucoyl-sn-glycero-3-phosphate (Sodium Salt), 1,2-Dipalmitoyl-sn-glycero-3-phosphocholine, 1,2-Dipalmitoyl-sn-glycero-3-phosphate (Sodium Salt), 1,2-Distearoyl-sn-glycero-3-phosphoethanolamine, 1,2-Distearoyl-sn-glycero-3-phosphoethanolamine etc.). The MDNPs are mixed with lipids and an emulsion is formed where MDNPs are coated with lipid due to electrostatic and hydrophobic and hydrophilic interactions. The emulsion is finally coated with terpolymer. The terpolymer coated the MDNPs and lipid emulsion by electrostatic and hydrophobic and hydrophilic force of interactions. The final emulsion is processed through ultra-high sonication or high-pressure homogenizer to obtain a homogeneous nanoparticle emulsion.

To obtain a functionalized nanoparticle for targeting application a targeting moiety conjugated terpolymer is used. In one example anti-amyloid β (Aβ) antibody functionalized BTRA-NCs are used to target Aβ aggregates and plaques in the brain of Alzheimer's disease model. The functionalized NPs showed a much higher accumulation in the brain especially in the plaque area when compared to black nanoparticles without targeting peptide.

Formulation #3-GDNF-TPN (Terpolymer Nanoparticle)

The formulation #3 comprises a lipid and protein core and is further embedded into the layer of poly(methacrylic acid)-polysorbate 80-starch (terpolymer).

The formulation #3 can be prepared by any method known that protein was entrapped in a lipid/polymer complex due to strong electrostatic interaction between the protein and the terpolymer. For example, GDNF are loaded into lipid/terpolymer matrix and the formulation #3 (GDNF-TPN) have a diameter of about 20 nm to about 200 nm. Preferable, the nanoparticles of the formulation #3 have a diameter of about 110 nm, a negative charge of about –50 mV.

There are several advantages of the formulation #3. For example, the formulation #3 has the ideal size and charge for in vivo applications (100-150 nm and –50 mV); uniform spherical shape allows for BBB penetration; can be further functionalized with different molecules via the —OH or —COOH groups on the terpolymer, e.g. CNS disease targeting peptide/antibody, fluorescent and near infrared dyes etc.; has high colloidal stability under physiological conditions; has a sustained in vitro drug release profile for over 50 hours; the bioactivity of GDNF is preserved after loading into nanoparticles; reach to the healthy brain with 15 mins and deliver higher levels of GDNF into healthy brain; extend GDNF circulation time and increase total drug exposure over time in the blood compared to free GDNF.

Formulation #4-FK506-TPN

The formulation #4 comprises a solid lipid domain of lipid stabilized with an amphiphilic copolymer comprised of poly(methacrylic acid)-polysorbate 80-starch (terpolymer) and a lipid which is conjugated onto terpolymer.

The formulation #4 can be prepared by any method known that a hydrophobic drug was entrapped in a lipid/polymer complex due to hydrophobic interaction with the lipid groups in the amphiphilic polymer and partitioning into the solid lipid domain. For example, FK506 are loaded into lipid/terpolymer matrix and the nanoparticles in formulation #4 (FK506-TPN) have a diameter of about 20 nm to about 200 nm. Preferable, the nanoparticles of the formulation #4 have a diameter of about 80 nm, a negative charge of about –54 mV.

There are several advantages of the formulation #4. For example, the formulation #4 has the ideal size and charge for in vivo applications (100-150 nm and –50 mV); can be further functionalized with different molecules via the —OH or —COOH groups on the terpolymer-lipid, e.g. CNS disease targeting peptide/antibody, fluorescent and near infrared dyes etc; has a sustained in vitro drug release profile for over 50 hours; show the attenuation against cisplatin induced cytotoxicity toward different MEF cells; deliver the FK506 into brain with 15 mins and accumulate into brain inflammatory areas for at least 4 hours.

Formulation #5-DEVD-TPN

The formulation #5 comprises a peptide domain self-assembled by an amphiphilic copolymer comprised of poly (methacrylic acid)-polysorbate 80-starch (terpolymer) and a lipid which is conjugated onto terpolymer.

The formulation #5 can be prepared by any method known that a hydrophilic drug was self-assembled by an amphiphilic polymer. For example, Z-DEVD-FMK (DEVD) is loaded into terpolymer-lipid matrix by self-assembly and the nanoparticles in formulation #5 (DEVD-TPN) have an average diameter about 20 nm to about 200 nm. Preferable, the nanoparticles of the formulation #4 have a diameter of about 54 nm, a negative charge of about −26 mV.

There are several advantages of the formulation #5. For example, the formulation #5 has the ideal size and charge for in vivo applications (30-100 nm and −26 mV); can be further functionalized with different molecules via the —OH or —COOH groups on the terpolymer-lipid, e.g., disease targeting peptide/antibody, fluorescent and near infrared dyes etc.; has a sustained in vitro drug release profile for over 50 hours; show the attenuation against cisplatin induced cytotoxicity toward different MEF cells.

Formulation #6-Curcumin-TPN

The formulation #6 comprise a solid lipid matrix stabilized with an amphiphilic copolymer comprised of poly (methacrylic acid)-polysorbate 80-starch (terpolymer) and a lipid which is conjugated onto terpolymer.

The formulation #6 can be prepared by any method known that a hydrophobic drug was entrapped in a lipid/polymer complex due to hydrophobic interaction with the lipid groups in the amphiphilic polymer and partitioning into the solid lipid domain. For example, curcumin is loaded into lipid/terpolymer matrix and the formulation #6 (curcumin-TPN) have a diameter of about 20 nm to about 200 nm. Preferable, the nanoparticles of the formulation #6 have an average diameter about 110 nm, a negative charge about −45 mV.

There are several advantages of the formulation #6. For example, the formulation #6 has the ideal size and charge for in vivo applications (100-150 nm and −45 mV); can be further functionalized with different molecules via the —OH or —COOH groups on the terpolymer-lipid, e.g., CNS disease targeting peptide/antibody, fluorescent and near infrared dyes etc.; has a sustained in vitro drug release profile for over 50 hours; shows the quick cell uptake with 2 hours.

EXAMPLES

Abbreviations

Alzheimer's disease (AD)
Amyloid-β (Aβ)
Anti-Aβ antibody (aAβ)
Anti-Aβ antibody 4G8 conjugated-BTP (aAβ-BTP)
Apolipoprotein E (ApoE)

28

Blood brain barrier (BBB)
Brain targeted polymer (BTP)
Brain-targeted (BT)
Cerebrospinal fluid (CSF)
Circular dichroism (CD)
Confocal laser scanning microscopy (CLSM)
Fetal bovine serum (FBS)
Gadolinium (Gd)
Hydrogen peroxide $H_2O_2$
Hyperphosphorylated tau (p-tau)
Immuno-histochemical (ICH)
Inductive coupled plasma atomic emission spectroscopy (ICP-AES)
Interleukin-1β (IL-1β)
Intravenous (i.v.)
Low density lipoprotein (LDL)
Magnetic resonance (MR)
Magnetic resonance imaging (MRI)
$MnO_2$ nanoparticle ($MnO_2$-NPs)
Nanoconstruct (NC)
Nanoparticles NPs
Pearson's correlation coefficient (PCC)
Polydispersity indices (PDI)
Polysorbate 80 (PS 80)
Polyvinyl alcohol-PVA
Potassium permanganate-$KMnO_4$
Reactive oxygen species (ROS)
ROS-activatable (RA)
anti-Aβ antibody (aAβ)-conjugated, brain-targeted (BT), and ROS-activatable (RA) $MnO_2$ nanoparticle ($MnO_2$-NPs)-containing nanoconstruct (NC) (aAβ-BTRA-NC)
Sodium dodecyl-sulfate polyacrylamide gel electrophoresis (SDS-PAGE)
Transmission electron micrographs (TEM)
Ultraviolet-visible (UV-vis) spectroscopy
X-ray photoelectron spectra (XPS)
Poly(methacrylic acid)-polysorbate 80-starch (Terpolymer)
Targeted Polymeric Nanoparticles (TPN)

Example 1

Preparation and Characterization of BTRA-NCs and Anti-Body Functionalized BTRA-NCs A biocompatible and pharmaceutically acceptable mono-lithic-matrix type polymer-lipid-metal oxide nano-construct (i.e., BTRA-NC) was prepared using sonication or high-pressure homogenizer technique. A brain targeted polymer (BTP) was synthesized by grafting polymerization of poly (methacrylic acid) and polysorbate 80 (PS 80) onto starch. The polymer was washed through dialysis (MWCO: 12-14 kDa) and dried in oven or through freeze drier. The dried polymer was conjugated with anti-Aβ antibody 4G8 conjugated-BTP (aAβ-BTP) using the ED chemistry. For bench scale batch the brain targeted, reactive oxygen species (ROS) activable nano-constructs (BTRA-NCs) and anti-Aβ (aAβ)-BTRA-NCs were prepared using a synthesis method shown schematically in FIG. 1a. Briefly, ethyl arachidate (15 mg) (lipid, or phospholipid) was added to a 15 mL conical tube, and heated to 52° C. PVA (220 μL, 0.5 wt % in distilled deionized water (DDIW) Milli-Q water, MilliPore Canada Ltd, CA) solution, and 15 mg of BTP (or 16 mg of 4G8-BTP) and 200 μL of DDIW were added to the solution and stirred for 10 min. In a new Eppendorf tube, $KMnO_4$ (12 mg) was dissolved in 250 μL of DDIW and 100 μL of $KMnO_4$ solution was added to the previous lipid polymer mixture and sonicated for 5 min using a Hielscher UP 100H probe ultrasonicator (Ringwood, NJ, USA) at 80% peak amplitude or emulsion was processed using high-pressure homogenizer at appropriate pressure setting. Following process, the entire nanoparticle solution was quickly transferred into dextrose (1-5 wt. %) being stirred on ice. The nanoparticles were purified by extensive re-suspending and filtec red by Nanosep® 100K Omega centrifuge filters (Mississauga, ON, CA) or for large scale volume using the tangential flow filtration method.

Characterization of BTRA-NCs and aAβ-BTRA-NCs

The particle size and zeta potential of the BTRA-NCs and aAβ-BTRA-NCs were measured using the Malvern Zetasizer Nano ZS (Worcestershire, UK). The morphology of the NCs were evaluated using the transmission electron microscopy (TEM). For TEM, the NCs were dispersed in DDIW and a drop was placed onto a carbon coated copper TEM grid. The TEM grid was then dried overnight at room temperature. TEM images were acquired by a Hitachi H7000 electron microscope (Hitachi Canada, Ltd., Mississauga, Ontario, Canada) with an accelerating voltage of 75 kV. The X-ray photoelectron spectra (XPS) analysis was performed on a K-Alpha XPS system from Thermo Fisher Scientific (East Grinstead, UK). To determine the stability of the NCs, 200 μL of NCs were incubated in 2 mL aqueous solution of 50% fetal bovine serum (FBS) (Sigma-Aldrich, Canada) for up to 48 h at 37° C. Aliquots were taken at various time intervals and diluted with DDIW for analysis of particle size and zeta potential.

Figure 2:
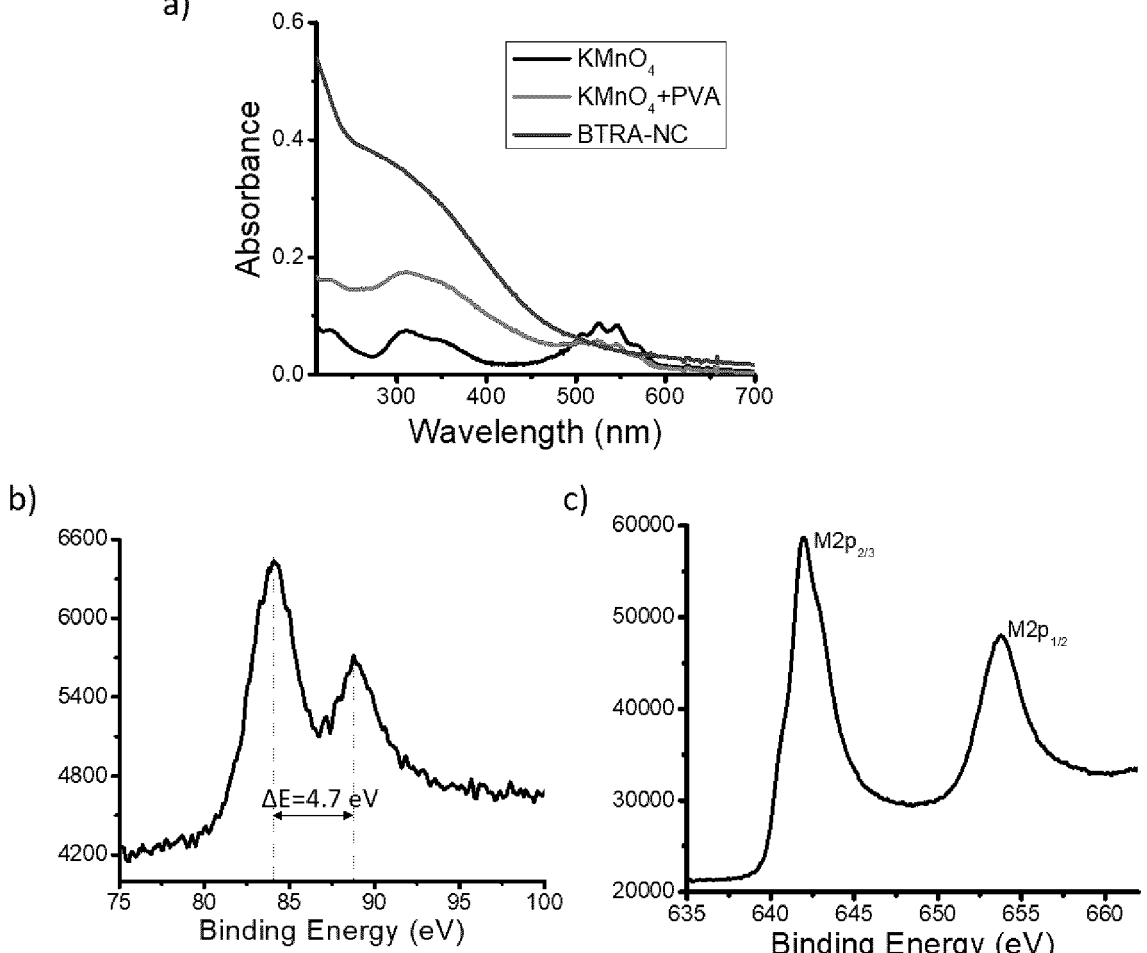
FIG. 2: Confirmation of conversion of $KMnO_4$ to $MnO_2$. a) UV—vis spectra of $KMnO_4$ (black), $KMnO_4$+PVA (red) in aqueous solutions and BTRA-NC suspension (blue). During the process of "one-pot" reaction and self-assembly of BTRA-NC, three peaks respectively at 315 nm, 525 nm and 545 nm originated from $KMnO_4$ gradually disappeared in the presence of PVA with the concurrence of a new peak at 370 nm indicating the formation of $MnO_2$ nanoparticles (red line, $KMnO_4$-PVA). The completion of $KMnO_4$ conversion to $MnO_2$ nanoparticles and self-assembled into the PVA-lipid matrix-BTP was confirmed that peaks at 525 nm and 545 nm disappeared (blue line, BTRA-NC). b) XPS Mn3s spectra of BTRA-NCs, c) Typical XPS Mn2p spectra from the BTRA-NC further confirmed the complete conversion of $KMnO_4$ to $MnO_2$.
Figure 3:
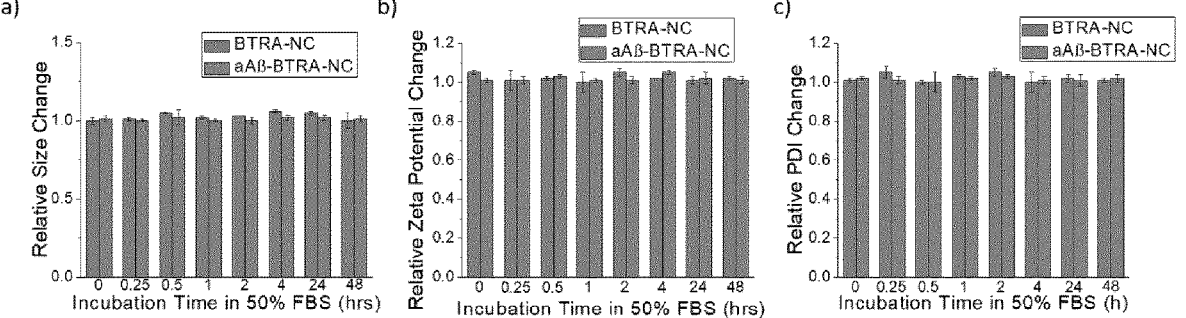
FIG. 3: shows a-c) Colloidal stability test by relative particle size, Zeta potential and PDI of BTRA-NCs and aAβ-BTRA-NCs in 50% FBS at 37° C. at various times points up to 48 h. The data are presented as mean±standard deviation (SD, n=3).

The resultant BTRA-NCs and aAβ-BTRA-NCs were 66-69 nm in average diameter, with a polydispersity index (PDI) of 0.26-0.27, and a zeta potential of approximately −50 mV (Table 2 and FIG. 1b,c). Transmission electron micrographs (TEM) confirmed the spherical shape and nearly uniform size of the NCs (FIG. 1b). It was estimated 100% of $KMnO_4$ conversion to manganese dioxide nanoconstruct ($MnO_2$—NC) occurred in the PVA-BTP-lipid matrix by ultraviolet-visible (UV-vis) spectrophotometry analysis FIG. 2a. The nanoparticles were negatively charged with a zeta potential of −20-50 mV (FIG. 1b). X-ray photoelectron spectra (XPS) confirmed the formation of Mn(IV) in $MnO_2$-containing BTRA-NCs (FIG. 2b&2c). The stability of nanoparticle is confirmed up to 48 hrs by measuring the size distribution, polydispersity index (PDI). The nanoparticles were stable for over 48 h at 37° C. in 50% fetal bovine serum (FBS) (FIG. 3a-c).

Figure 4:
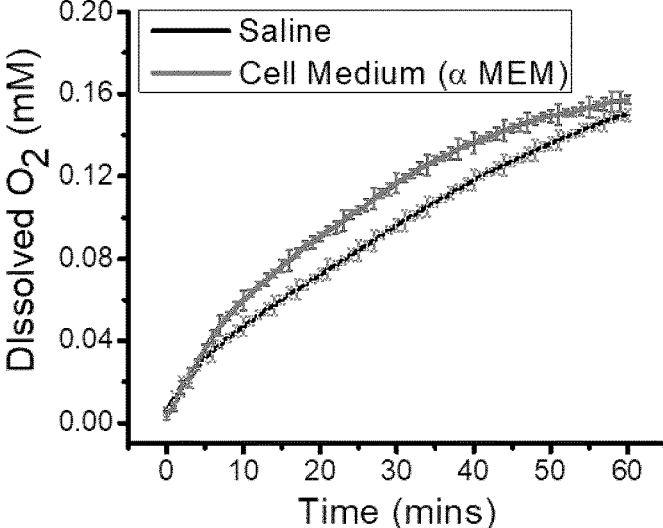
FIG. 4: shows $O_2$ generation by addition of $H_2O_2$ to aAβ-BTRA-NCs suspensions in saline or growth medium. The oxygen generation ability of NCs is confirmed by a semi-sealed chamber coupled with a MI-730 micro-oxygen electrode (Microelectrodes Inc, Bedford, NH, USA), at 37° C.

Scientific, CA) and dissolved $O_2$ was removed by bubbling with $N_2$ for about 30 min. At this point, $H_2O_2$ (500 μM) was injected into the chamber and generated $O_2$ was monitored every 60 sec using an Oakton pH 1100 (Thermo Fisher Scientific Inc, USA) coupled with $O_2$-ADPT Oxygen Adapter (Microelectrodes Inc, USA). The electrode was calibrated according to manufacturer's instructions. Pure saline and αMEM were used as control. The results confirmed that nanoparticles are able to generate the $O_2$ up to 60 min following the reaction with $H_2O_2$ in both saline and cell media (FIG. 4).

In Vitro Relaxivity Measurement of BTRA-NCs and aAβ-BTRA-NCs

To confirm the magnetic resonance imaging (MRI) contrast agent ability of BTRA-NCs and aAβ-BTRA-NCs, in vitro MRI study was performed. For in vitro MRI analysis, 200 μL, of a free aqueous dispersion of aAβ-BTRA-NCs (or BTRA-NCs) with or without $H_2O_2$ (500 μM) were added at different concentrations in wells of 96 well plates in triplicate. For the reaction of nanoparticles with $H_2O_2$, required amount of $H_2O_2$ was added 30 min prior to the MRI imaging. Each plate was then imaged using a 7 T micro-MRI (BioSpec USR, Bruker, Germany) equipped with a 15.5 cm inner diameter quadrature RF coil and B-GA20S gradient coil insert. The longitudinal relaxation time $T_1$ was quantified using a variable-repetition-time spin-echo pulse sequence (2D-RARE, RARE factor 2; TE 8.7 ms; TR of 25, 50, 100, 150, 250, 500, 750, 1000, 1500, 2500, 5000, 7500 ms; 220×160 matrix over 110×80 mm field-of-view for 0.5 mm in-plane resolution; 2 mm slice thickness; 119 kHz readout bandwidth; 19 min 19 sec acquisition). $T_1$ maps were generated using a custom MATLAB script (The Mathworks, Natrick, MA, USA), and $T_1$ values corresponding to each well were extracted using Medical Image Processing, Analysis and Visualization (MIPAV National Institutes of Health, Bethesda, MD, USA). For each concentration series, the $T_1$ relaxivity ($r_1$) was calculated by linear regression of $R_1$ ($1/T_1$) and Mn concentration data pairs according to the standard equation:

$$R_1 = R_1^0 + r_1 \cdot c(Mn)$$

TABLE 2

| Summary of particle size, PDI, Zeta potential, representative | | | | | |
|---|---|---|---|---|---|
| | | | | $R_1$ Relaxivity (mM sec)$^{-1}$ | |
| Formulations | Size (d, nm) | Polydispersity Index (PDI) | ζ-Potential (mv) | Without $H_2O_2$ | With $H_2O_2$ |
| BTRA-NC | 65.9 ± 5.2 | 0.26 ± 0.02 | −50 ± 3.8 | 2.9 ± 0.8 | 16.6 ± 1.2 |
| aAβ-BTRA-NC | 68.6 ± 1.8 | 0.27 ± 0.02 | −49 ± 4.1 | 3.0 ± 0.5 | 16.7 ± 0.9 |

Measurement of Dissolved $O_2$ (DO)

Figure 5:
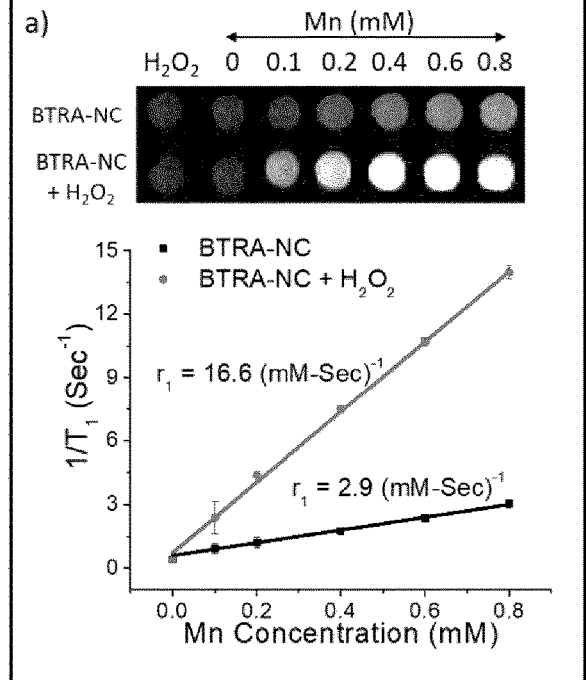
FIG. 5: shows in vitro relaxivity measurements of NCs. a) BTRA NCs, b) aAβ-BTRA-NCs. Top: Representative $T_1$-wt MR images of NCs alone, or NCs+$H_2O_2$ (500 μM) at 7 T. Bottom: Relaxation rate $1/T_1$ vs. Mn concentration plots.
Figure 5:
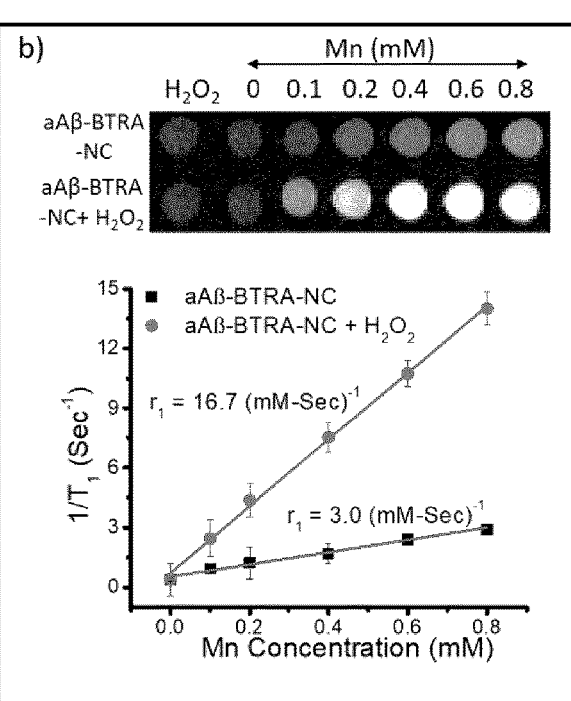

To confirm the ability of BTRA-NCs and aAβ-BTRA-NCs to produce $O_2$ following reaction with $H_2O_2$, in vitro experiments were performed using a commercially available probe to detect the molecular $O_2$ (FIG. 4). The reaction between BTRA-NCs and $H_2O_2$ was performed in a semi-sealed chamber coupled with a MI-730 micro-oxygen electrode (Microelectrodes Inc, Bedford, NH, USA), at 37° C. BTRA-NCs (100 μM $MnO_2$) were dispersed in normal saline or cell growth medium (αMEM) (Thermo Fisher where, $$R_1^0$$

is the relaxation rate of DDIW in the absence of Mn, and c(Mn) is the Mn concentration obtained ICP-AES analysis (FIG. 5a &b).

In vitro MRI results showed 5.6-5.7-fold increase in $T_1$ relaxivity (r1) in the presence of $H_2O_2$ due to the conversion of $MnO_2$ in the nanoparticles to $Mn^{2+}$ (FIG. 5a &b). Both BTRA-NCs and aAβ-BTRA-NCs generated 3.5-fold higher r1 values (16.6-16.7 mM$^{-1}$ sec$^{-1}$, FIG. 1b, FIGS. 5a and 5b) compared to commercially available GADOVIST® 1.0 (4.7 mM$^{-1}$-sec$^{-1}$).

Figure 6:
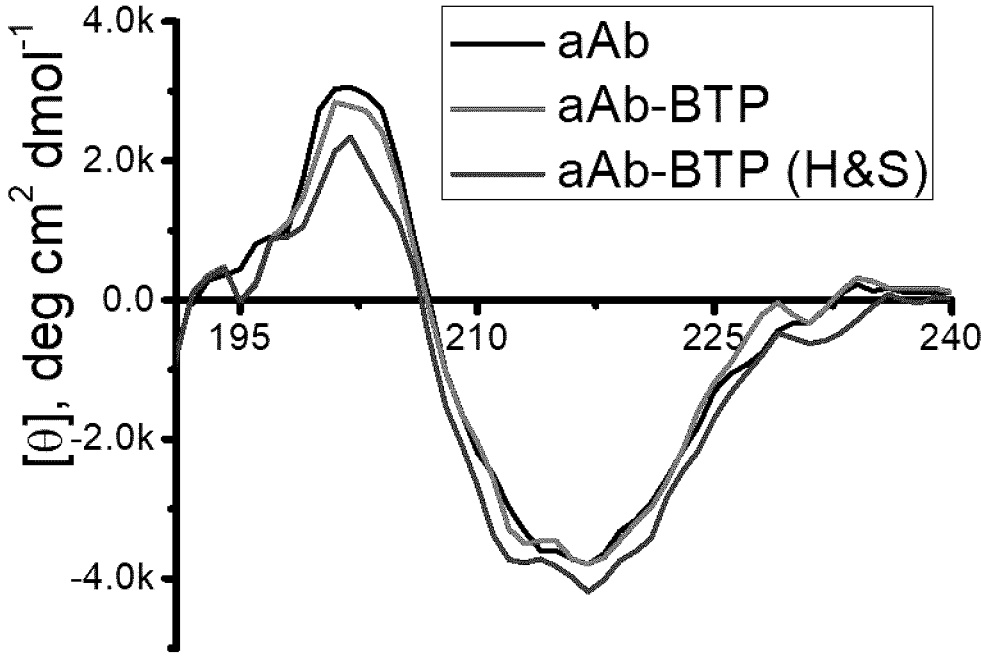
FIG. 6: shows CD spectra of aAβ, aAβ-BTP and aAβ-BTP after heating and sonication (aAβ-BTP H & S). Same heating and sonication condition were used those were used during the NCs synthesis.

Confirmation of Structure of Anti-Aβ Antibody (4G8) after Conjugation and NCs Formulation The secondary structure of native antibody (4G8), 4G8-BTP with or without exposure to heating and sonication during NC synthesis procedure was examined using a circular dichroism (CD) spectropolarimeter (Jasco J-810, Easton, MD, USA) equipped with a Peltier temperature controller operated at 25° C. (FIG. 6). Samples were scanned at 1 nm intervals between 190 nm and 240 nm using an 8 sec response time. Measurements were repeated 3 times and averaged.

The CD spectroscopy showed that the secondary structure of 4G8 antibody was preserved after chemical conjugation with BTP and exposure to heat (55° C.) and sonication during NC synthesis (FIG. 6).

In Vitro Binding with Aβ Peptide by aAβ-BTRA-NCs Versus BTRA-NCs

Figure 7:
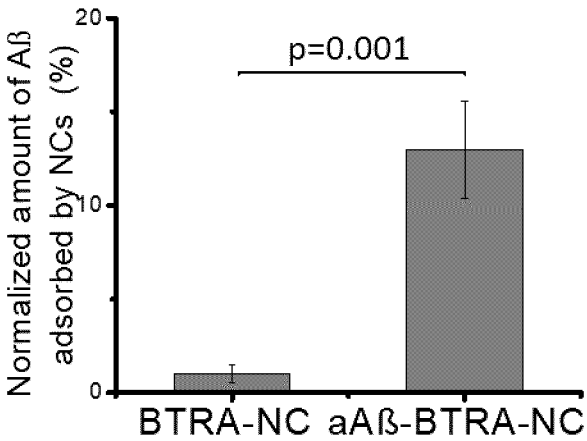
FIG. 7: shows percent of soluble Aβ1-42 peptide adsorbed by BTRA-NCs and aAβ-BTRA-NCs.

The binding ability of NCs and Aβ peptide was also confirmed in vitro. For this purpose, NCs and Aβ1-42 peptide (ab120301, Abcam, CA) were incubated at a final concentration of 1.0 and 0.02 μM, respectively, in 1.0 mL of PBS (pH=7.4) overnight at 4° C. Then the tubes were centrifuged at 10,000 g for 30 mins to remove NCs and the adsorbed entities. The supernatants were analyzed by ELISA assay (Amyloid beta 42 Human ELISA Kit, Ultrasensitive, Thermo Fisher Scientific, CA). Experiments were performed in triplicate, and the results present as mean±standard deviation. A strong binding of aAβ-BTRA-NCs with soluble Aβ was demonstrated by an absorption test which showed >10-fold of Aβ1-42 peptide removed from the medium by aAβ-BTRA-NCs than the non-targeted BTRA-NCs (FIG. 7).

Determination of BBB-Permeability of NCs Using an In Vitro 3D Human BBB Model

Figure 8:
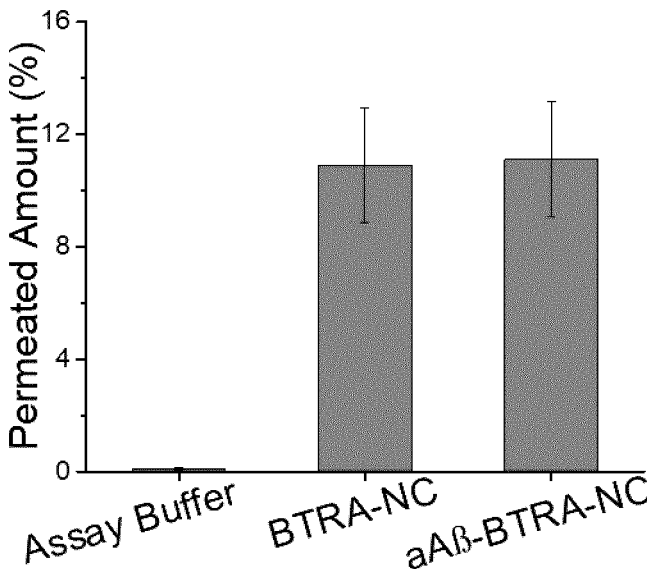
FIG. 8: shows amounts of Cy5.5-labeled BTRA-NCs or Cy5.5-labeled aAβ-BTRA-NCs permeated across the in vitro human 3D BBB model determined using a fluorescence spectroscope. Error bars indicate the SD of three independent experiments.

An in vitro three dimensional (3D) human blood brain barrier (BBB) transwell co-culture assay (Alphabioregen, Boston, MA, USA) was used to assess the BBB permeability of BTRA-NCs and aAβ-BTRA-NCs. The assay consists of a primary human brain endothelial cell monolayer, cultured on a transwell insert, co-cultured with human brain pericytes and human astrocytes. Permeability experiments were performed following the manufacturer's protocol. The endothelial cell monolayer was kept in culture until a trans-endothelial electrical resistance (TEER) value between 150 to 300Ω cm2 was achieved. Culture medium in the insert (apical side) was replaced with 200 μL of assay buffer containing 1 mg mL-1 of cyanine 5.5(Cy5.5)-labeled BTRA-NCs or aAβ-BTRA-NCs, with culture medium in the assay plate and incubated at 37° C. at 5% $CO_2$ for 30 min. The fluorescence intensity of Cy5.5-labeled NCs was measured using a fluorescence spectroscope (λex/em=650/700 nm) after incubation and the concentration of BTRA-NC or aAβ-BTRA-NC was determined with respect to the appropriate calibration curve. The collected NCs from basolateral side were further used for the incubation with TgCRND8 mouse brain cryosections. Both BTRA-NCs and aAβ-BTRA-NCs permeated >10% of the administered dose after 30 min (FIG. 8), indicating that aAβ conjugation did not adversely affect BBB-crossing capability of the NCs.

Confirmation of Aβ-Binding Bioactivity after Conjugation and NCs Formulation

Figure 9:
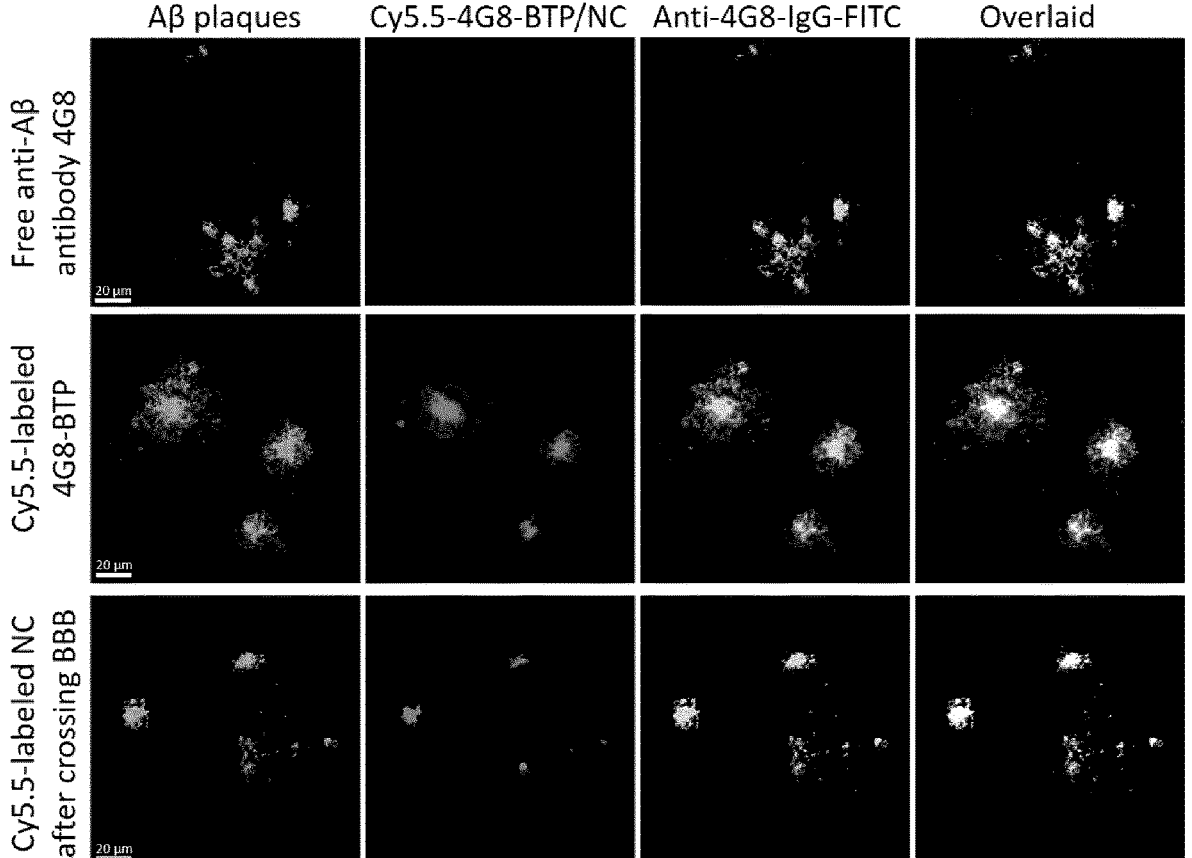
FIG. 9: shows CLSM images of TgCRND8 mouse brain (age: 9-months) cryosections (15 μm thick) following incubation with primary antibody 4G8, Cy5.5-labeled 4G8-BTP conjugate, or Cy 5.5-labeled aAβ-BTRA-NCs collected from basolateral side of the human 3D BBB model after the in vitro permeation test. The Aβ plaques stained with resorufin appear as orange, while the plaques stained with IgG-FITC secondary antibody for 4G8 appear as green. Cy5.5 linked with BTP or NCs appears as red. Scale bar corresponds to 20 μm for all images.

To assess the preservation of Aβ plaque-binding ability of 4G8 after chemical conjugation with BTP and NC synthesis, frozen brain sections from TgCRND8 mice of 9-month age were used. The sections (obtained from OCT frozen 20 μm coronal cryo-sections) were blocked in phosphate buffered saline (PBS) containing 0.1% Triton X-100, and 1% BSA at room temperature for 45 min. Sections were further immersed in 0.25% Triton X-100 (in PBS) for 30 min and then incubated with primary antibody 4G8 (1:200), or 4G8 equal amounts of Cy5.5-labeled 4G8-BTP conjugate, Cy5.5-labeled aAβ-BTRA-NCs collected from the basolateral side of an in vitro 3D human BBB transwell co-culture assay, diluted in 0.25% Triton X-100 (in PBS) at 4° C. overnight. After that, the sections were incubated in secondary IgG-FITC (1:100, Goat Anti-Rabbit IgG H & L (FITC), Abcam Inc, ON, CA) for 1 h at room temperature in 0.25% Triton X-100 in PBS and were washed three times in PBS, once in 50% ethanol in PBS, followed by three more PBS washes. Lastly, sections were cover slipped and imaged using a Zeiss LSM700 Confocal laser scanning microscopy (CLSM) (Carl Zeiss, Jena, Germany) using fluorescent excitation and emission filters appropriate for detection of the indicated chromophores. The CLSM of brain tissue slices demonstrated co-localization of 4G8 antibody staining (FITC-green), Cy5.5 labeled 4G8-BTP or aAβ-BTRA-NCs (red) with Aβ plaques (resorufin staining, orange) for all formulations (FIG. 2i). The results confirmed that the Aβ-binding affinity of 4G8 in aAβ-BTRA-NCs was preserved after crossing the BBB (FIG. 9). The capability of aAβ-BTRA-NCs delivering 4G8 efficiently across the BBB may represent a potential treatment opportunity, for anti-Aβ antibodies have been increasingly explored to target Aβ for specific AD interventions.

SDS-PAGE Analysis of the Free and BTRA-NC-Bound ApoE

Figure 10:
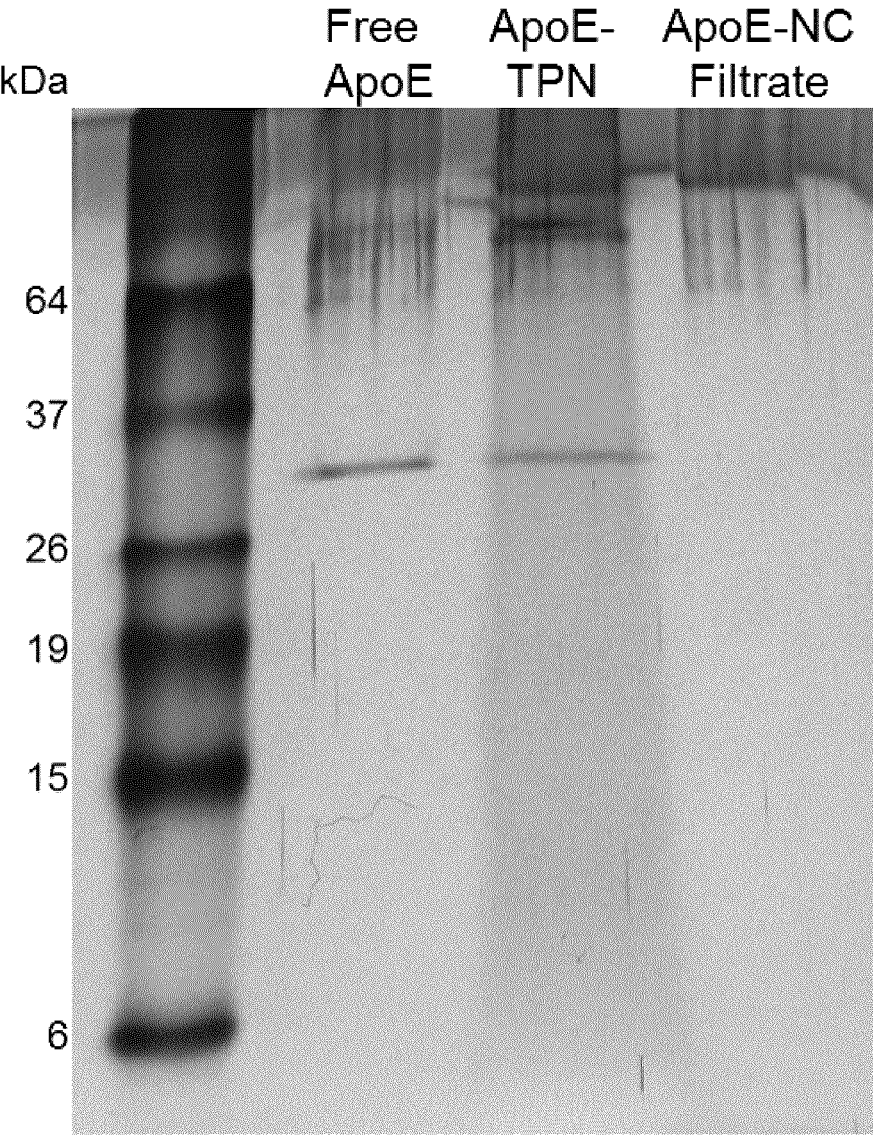
FIG. 10: shows SDS-PAGE analysis of the free ApoE, NC bound ApoE and filtrate ApoE in 12% Mini-PROTEAN®TGX™ precast gel (Bio-RAD, U.S.A.) using silver staining method. The first column represents the protein ladder. ApoE band is present at approximately 35 kDa.

To test the hypothesis that ApoE decoration is critical for NCs to cross the BBB, the adsorption of ApoE onto BTRA-NCs was confirmed using sodium dodecyl-sulfate polyacrylamide gel electrophoresis (SDS-PAGE) (FIG. 10). For this experiment after incubation of ApoE with BTRA-NCs, the suspension was transferred into a centrifugal filter (MWCO=50 kDa), (Sigma-Aldrich, CA) and centrifuged for 15 min at an RCF of 21,100×g. The filtrate was then collected for SDS-PAGE analysis. Briefly, 50 μL of protein samples (free ApoE, BTRA-NC-bound ApoE and filtrate ApoE) were immediately solubilized in a same volume of sample buffer (Bio-Rad, USA) and boiled for 10 min. Then the solution was centrifuged at 10000×g, and 5 μL of samples was loaded onto a 12% Mini-PROTEAN®TGX™ precast gel (Bio-RAD, U.S.A.) and ran at 70 V for stacking gel and 120 V for separating gel (Mini-protein unit, Bio-Rad, USA). Afterwards the gel was stained using Thermo Scientific™ Pierce™ Silver Stain Kit under the manufacturer's protocol and gel image was visualized using Alpha Innotech, U.S.A.

Figure 11:
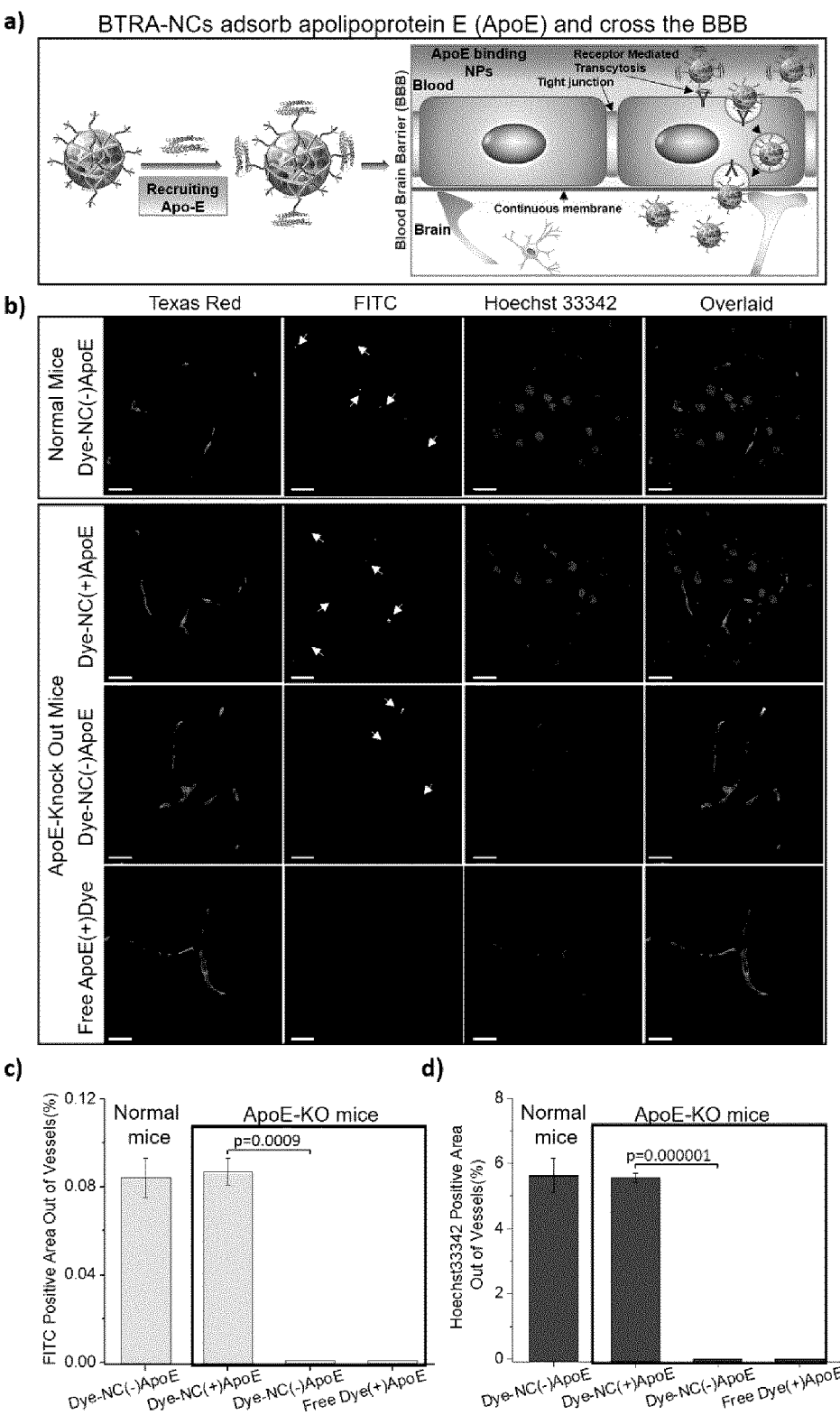
FIG. 11: shows a) Schematic diagram depicting BTRA-NCs recruited apolipoprotein E facilitating LDLR-mediated BTRA-NC across BBB. b) CLSM images of healthy C57BL6j and ApoE-Knock-Out mouse brain sections following the treatment with different formulations (Y-axis legend). Two hours post i.v. injection of the formulations, blood vessels were labeled by i.v. administration of Texas Red-dextran 15 min before euthanasia. Hoechst 33342 dye-labeled cell nuclei appear blue. Texas Red-dextran and FITC appears as red and green, respectively. Arrows indicate representative FITC-labeled NCs. Scale bar corresponds to 20 μm for all images. c) Quantification of FITC-labeled NCs and d) Quantification of Hoechst 33342 positive areas outside of blood vessels. Fifteen stacks from 3 mice were examined. p values indicate statistically significant difference as compared to Dye-NC(−)ApoE treated groups. Error bars indicate the standard deviation of three independent experiments (n=3).

Determination of the Role of ApoE on the Delivering BBB-Impermeable Dye into Brain Parenchyma Using ApoE-Knock Out Mice and Wild-Type Mice The ability of NCs to cross the BBB was investigated be observing the extravasation of the BBB-impermeable dye Hoechst 33342 and FITC-labeled BTRA-NCs. The BTRA-NCs with or without incubation with ApoE (BTRA-NC (+/−) ApoE) were injected i.v. into ApoE knockout (KO) mice, while BTRA-NCs without ApoE treatment were injected into normal C57Bl6J mice (FIG. 11). For this purpose the BBB-impermeable nucleus-staining dye
Hoechst 33342 was loaded into FITC (FA)-labeled BTP
based BTRA-NCs by heating 250 μL of 10 mg mL$^{-1}$
Hoechst 33342 solution, 200 μL of 75 mg mL-1 FA-BTP
solution and 15 mg of ethyl arachidate at 45° C. The mixture
was stirred for 20 min. BTRA-NCs were formed under
ultrasonication using a Hielscher UP100H probe ultrasoni-
cator for 10 min and suspended in sterile 5% dextrose to a
final Hoechst 33342 concentration of 2.5 mg mL$^{-1}$. An
analogous BTRA-NC coated with ApoE protein formulation
was prepared from FA-BTP using the same protocol. To
examine BTRA-NC penetration into healthy brain, C57BL/
6J mice (The Jackson Laboratory, Bar Harbor, Maine, USA)
were treated with 200 μL of Hoechst 33342-loaded BTRA-
NCs without ApoE via tail vein injection. Similarly, ApoE-
Knock Out mice were treated with BTRA-NC coated with
ApoE (0.1 mg mL$^{-1}$), BTRA-NCs without ApoE or Free
ApoE+Hoechst 33342 (ApoE: 0.1 mg mL$^{-1}$; Hoechst
33342: 2.5 mg mL$^{-1}$). Mice were euthanized 2 h following
treatment. Texas red-labeled dextran (70,000 MW) was
administered through i.v. (100 μL, 1% wt. solution) 15 min
prior to euthanasia. The brain was dissected, fixed in 10%
formalin for 3 h, transferred to 30% dextrose solution
overnight, embedded in Tissue-Tek OCT resin and finally
flash frozen. Thaw mounted 20 μm thick frozen sections
were obtained on a Leica, model CM3050S cryostat and
analyzed using Zeiss LSM700 confocal microscope and
fluorescent excitation and emission filters appropriate for
detection of the indicated chromophores (Dextran, Texas
Red: $\lambda_{ex/em}$=595/615 nm; FITC: $\lambda_{ex/em}$=490/520 nm;
Hoechst 33342: $\lambda_{ex/em}$=352/461 nm). Quantification of
FITC and Hoechst 33342 positive area outside of brain
blood vessels was performed on >2 visual fields per brain
and obtained using ImageJ software.

The CLSM images of brain tissue sections showed that
the BTRA-NCs without ApoE incubation (Dye-NC(−)
ApoE) stained parenchymal cell nuclei (blue) in normal
mice, while only ApoE treated BTRA-NCs (Dye-NC(+)
ApoE) could stain the cells in the ApoE-KO mouse brain
(top two panels, FIG. 3b). In these panels labeled nuclei
were identified as distal to local blood vasculature (identified
via Texas Red-dextran infusion) and FITC-NCs in the brain
tissue were outside of blood vessels (green, FIG. 3b). In
contrast untreated BTRA-NCs (Dye-NC(−)ApoE) or free
ApoE plus free dye remained confined within blood vessels
as evidenced by co-localization of blue (nuclei) and red
(blood vessels) staining and an absence of blue nuclei in the
brain parenchyma of ApoE-KO mice (FIG. 3b). Quantifica-
tion of FITC and dye positive labeling outside of brain blood
vessels further confirmed significantly higher BBB-penetra-
tion and extravasation of BTRA-NCs with ApoE than with-
out nanoparticle constructs lacking ApoE in ApoE-KO mice
(FIG. 3c, d). These results demonstrate that the BTRA-NCs
are able to extravasate from brain microvasculature to
deliver BBB-impermeable agent into the CNS. The results
further verify that BTRA-NCs cross the BBB through a
mechanism that involves adsorption of ApoE from plasma
and receptor-mediated transcytosis through brain vascular
endothelial cells across the intact BBB.

In Vivo Biodistribution and Accumulation of NCs in Aβ
Plaque Regions of Mouse Brain The in vivo bio-distribution and brain accumulation of the
NCs were determined using TgCRND8 mice of 6 months
old. HF750-labeled NCs (100 μmol kg$^{-1}$ animal body
weight) was injected i.v. in the tail vein of the Tg mice. At
different time points, the mice, anesthetized with 2% iso-
flurane breathing, were imaged at $\lambda_{ex/em}$=754/820 nm using Xenogen IVIS Spectrum Imaging System (PerkinElmer,
Massachusetts, US). For the ex-vivo imaging of the organs,
NCs treated mice were euthanized at 2 h post NCs i.v.
injection, and organs were dissected and imaged by the same
Imaging System.

Figure 12:
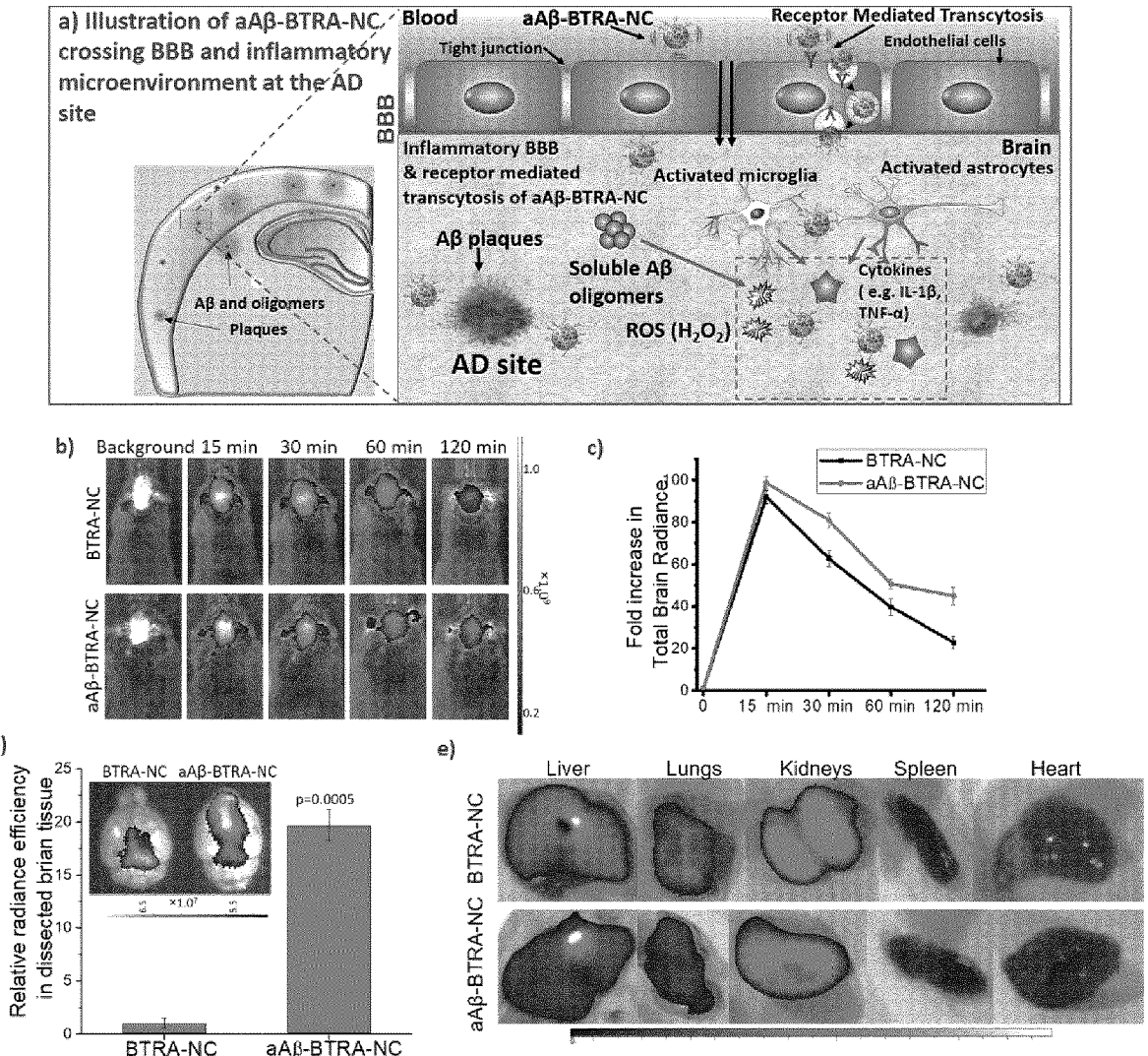
FIG. 12: shows a) Schematic illustration of the BBB-crossing mechanisms of aAβ-BTRA-NCs in healthy and AD brain and inflammatory microenvironment of AD site where there exist elevated levels of ROS (e.g. $H_2O_2$) and inflammatory cytokines (e.g. IL-1β and TNF-α). In healthy brain, the NCs cross the BBB via transcytosis mediated by low density lipoprotein receptor (LDLR). In the inflammatory AD brain, the NCs can also enter brain parenchyma via leaky vessels. b) Representative in vivo optical images of TgCRND8 mouse following i.v. injection of NCs at various times. c) Time-dependent fluorescence intensity in the brain region of Tg mice treated by iv injection of the NCs. The fluorescence intensity for the regions of interest was recorded as total radiant efficiency and normalized to respective background regions. Error bars indicate the standard deviation (SD) of three independent experiments (n=3). d) Bottom: Ex vivo brain images and quantitative results for fluorescent intensity recorded at 120 min post treatment. e) Representative ex vivo organ images showing the accumulation of the NCs in various organs at 2 h post-i.v. injections of the NCs.

Much higher accumulation and retention of aAβ-BTRA-
NCs in the AD brains were found (FIG. 12b), with 10-fold
higher fluorescence intensity in the brain tissue 120 min
following treatment than BTRA-NCs (FIGS. 12d and 12e).

For immunofluorescence (IF) microscopy, mouse brains
were collected at 2 h post i.v. injection of the NCs, sectioned,
and used for further experiments. Briefly, the animals were
sacrificed after the perfusion. The brain was removed and
fixed in 4% paraformaldehyde overnight in the fridge and
then cryoprotected in 30% sucrose. The sections were
obtained from OCT frozen 20 μm coronal cryo-sections. The
plaques in the brain sections were stained using resorufin.
The sections were blocked in PBS containing 0.1% Triton
X-100, 0.2% skim milk, and 1% BSA at room temperature
for 45 min. Sections were then immersed in 0.25% Triton
X-100 (in PBS) for 30 min at room temperature and then
incubated in 1 μM resorufin for 30 min at room temperature
in 0.25% Triton X-100 in PBS. Following these steps,
sections were washed three times in PBS, and then once in
50% ethanol in PBS, followed by three more PBS washes.
Sections were cover-slipped and imaged using a Zeiss
LSM700 confocal microscope (Carl Zeiss, Jena, Germany)
using excitation and emission filters appropriate for detec-
tion of the indicated chromophores (Cy3: $\lambda_{ex/em}$=595/615
nm; FITC: $\lambda_{ex/em}$=490/520 nm). The degree of co-localiza-
tion between FITC-labeled NCs (green) and Aβ plaques
(orange) was quantitatively evaluated by Pearson's correla-
tion coefficient (PCC).

Figure 13:
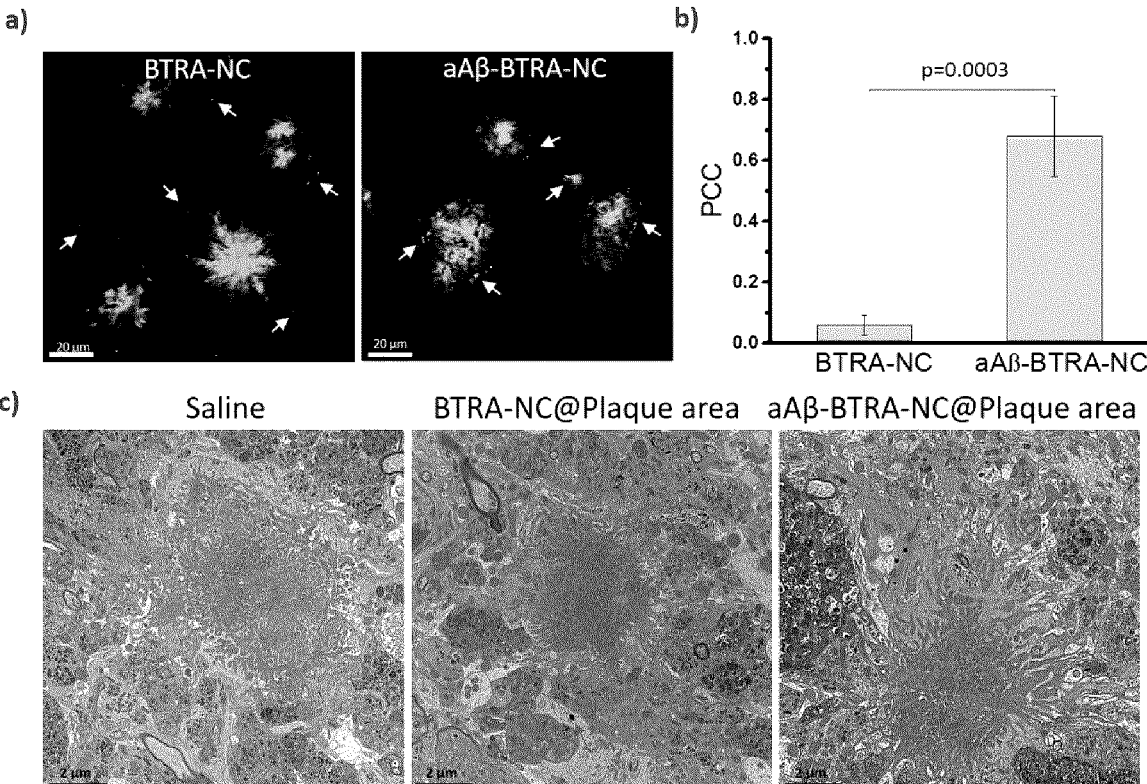
FIG. 13: shows a) CLSM images of brain sections from Tg mouse at 120 min post treatment. Aβ plaques were showed as orange; and NCs (green). b) Degree of co-localization of NCs and Aβ plaques determined by PCC. c) TEM images of Tg mouse brain sections at 120 min post NCs treatment. Red arrows show the accumulation of NCs around plaque areas. Scale bars=2 μm.

The CLSM of ex vivo brain sections revealed that more
FITC-aAβ-BTRA-NCs (green) accumulated within Aβ
plaque regions (orange), or with closer proximity than
FITC-BTRA-NCs (FIG. 13a). Pearson's correlation coeffi-
cient (PCC) of green (NCs) and orange (Aβ plaques) pixels
was found to be 0.65 for aAβ-BTRA-NCs and 0.1 for
BTRA-NCs, respectively (FIG. 13b), demonstrating the
ability of aAβ-BTRA-NCs to target Aβ plaques. TEM
images further confirmed more aAβ-BTRA-NCs (black
dots) than BTRA-NCs accumulated within Aβ plaque
regions in the AD brain tissue (FIG. 13c).

To visualize the location of 4G8-containing NC aggre-
gates within the brain, horse radish peroxidase affinity
purified goat polyclonal anti-mouse antisera (1:200, Jackson
ImmunoResearch, PA, USA) and secondary goat x-mouse
antibody in PBS (1:500, Vector Laboratories: BA-9200, CA,
USA) were applied and further developed with 3,3'-di-
aminobenzidine tetrahydrochloride (DAB) reagents follow-
ing manufacturer's protocol onto mouse brain cryosections.

The microscopic localization of NCs in Aβ plague regions
was also examined using TEM. The TEM images of brain
sections were acquired using a Hitachi H7000 electron
microscope with an accelerating voltage of 100 kV (FIG.
13c).

Immunohistochemistry Staining of Aβ-Plaques in Tg Brain
Sections

Mouse brain cryosections (20 μm) (obtained from OCT
frozen 20 μm coronal cryo-sections) were treated with an
endogenous peroxidase killing solution containing 3% H$_2$O$_2$
for 15 min at room temperature. Sections were stained
overnight at 4° C. with primary antibody 4G8 (1:200,
Biolegend, USA) in a histoblock solution (3% BSA, 20 mM
MgCl$_2$, and 0.3% Tween 20 in PBS) containing 5% goat
serum and 0.2 Triton X-100. After washing five times with PBS and PBS containing 0.3% TX-100, sections were incubated for 30 min at room temperature with secondary antibody goat x-mouse in PBS (1:500, Vector Laboratories: BA-9200, CA, USA), then washed 3 times with same buffers and developed with 3,3'-diaminobenzidine tetrahydrochloride (DAB) reagents following manufacturer's protocol. Aβ-plaques in all brain sections are visualized under light microscopy at 20× magnification.

Figure 14:
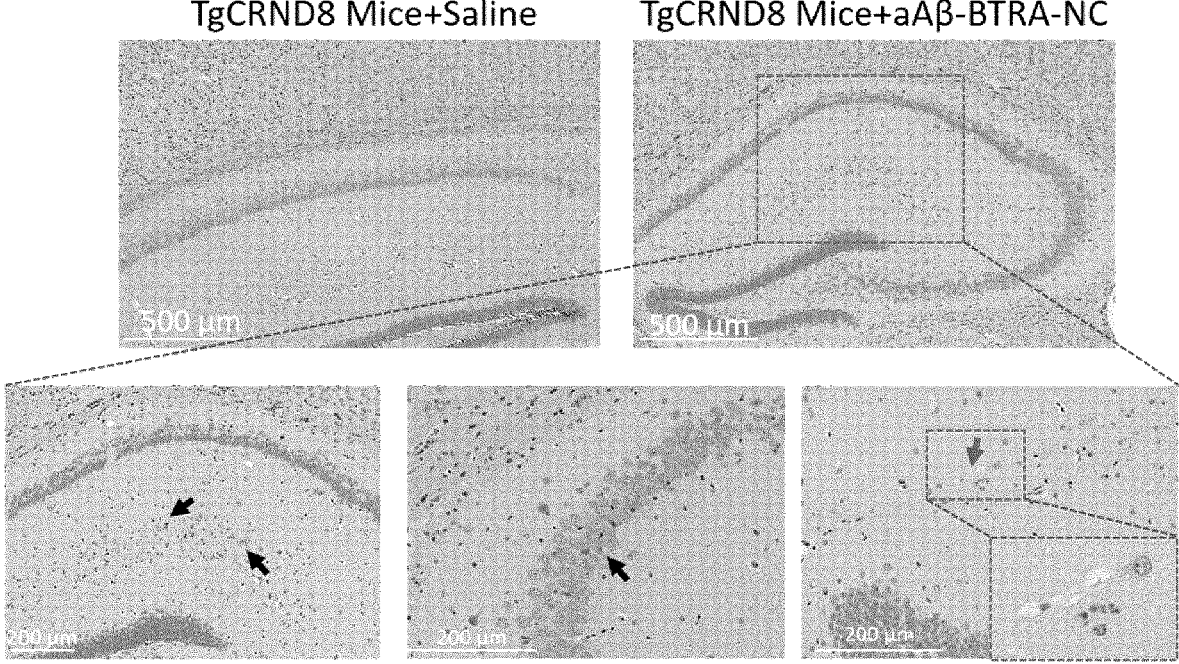
FIG. 14: shows 4G8 monoclonal antibody staining in hippocampus region of a 6-month old TgCRND8 mice treated with aAβ-BTRA-NCs. Horse radish peroxidase affinity purified goat polyclonal anti-mouse antisera and secondary goat x-mouse antibody were applied and further developed with 3,3'-diaminobenzidine tetrahydrochloride (DAB) reagents following manufacturer's protocol onto mouse brain cryosections. Black arrows represent 4G8 monoclonal antibody and red arrow represents blood vessel.

Immuno-histochemical (ICH) analysis of the hippocampus region of Tg mouse brain revealed a deposition of aAβ from the aAβ-BTRA-NCs in brain parenchyma outside of blood vessels (FIG. 14). These results verified that the anti-Aβ antibody retained bioactivity in vivo and enabled selective accumulation of aAβ-BTRA-NCs in Aβ-rich brain tissue.

MR Imaging of Brains of AD Mice of Various Ages and Age-Matched Wild-Type Mice

In vivo MRI of mouse brains were performed using a 7 T micro-MRI (BioSpec USR, Bruker, Ettlingen, DE) equipped with the B-GA12 gradient coil, 7.2 cm inner diameter linearly polarized cylindrical volume coil for radiofrequency (RF) transmission, and a dedicated murine brain receive-only RF coil for magnetic resonance (MR) signal reception. Mice were anesthetized by breathing 1.8% isoflurane and imaged in prone position on a custom slider bed. A pneumatic pillow fixed above the thorax/abdomen provided a signal for respiratory monitoring (SA Instruments, Stony Brook, NY, USA). Mice were also prepared via tail vein cannulation with a 27 G needle and a precision line to enable automated contrast agent injection following mouse positioning at system isocenter (Harvard Apparatus, Holliston, MA, USA). At baseline and at time-points of approximately 0, 30, 60, 90, and 120 min post-injection, high resolution 3D T1-weighted image sets were acquired without moving the mouse (3D-FLASH, TE/TR=4.5/75 ms, 320×320×40 matrix over a 19.2×19.2×10 mm field-of-view for 60×60×250 μm spatial resolution; 75 kHz readout bandwidth; 32 min acquisition time). Quantitative measurements were performed in registered manually-segmented brain cortex, hippocampus and CSF regions-of-interest (ROIs), using MIPAV software (National Institutes of Health, Bethesda, MD).

Electrochemical Analysis of Binding of Brain-Targeted Polymer (BTP) with Dissolved Mn (II) Ions Presence of free metal ions in MR contrast agents always raises the concern of metal toxicity. Thus, metal chelating agents are normally used in formulations. In aAβ-BTRA-NCs, the brain-targeted polymer (BTP) comprises poly (methacrylic acid) chains. We speculated that BTP could form an ionic complex with $Mn^{2+}$ resulting from the reaction of aAβ-BTRA-NCs with the ROS ($H_2O_2$). Differential pulse voltammetry (DPV) was used to detect this interaction using a Bioanalytical Systems Epsilon potentiostat with a three-electrode system featuring an Ag/AgCl reference electrode, a platinum counter electrode and a glassy carbon working electrode. Electrochemical signals were measured in an artificial cerebrospinal fluid (ACSF) containing (in mM) NaCl 124, KCl3.3, $NaHCO_3$ 26, $KH_2PO_4$ 1.3, $CaCl_2$ 2.5, $MgSO_4$ 1 and d-glucose 10 (pH 7.4) [67]. The $MnCl_2$ was dissolved into ACSF ($Mn^{2+}$: 0.8 mM) and titrated with different concentration of BTP (0-0.9 mg $mL^{-1}$, equals to [R—COO—]=0-4.2 mM) and the current signals were obtained with a potential step of 5 mV, pulse amplitude of 50 mV, pulse with 50 ms, and a pulse period of 100 ms. Results are shown in FIG. 18.

Measurement of ROS Levels in Brain Tissue

Intracellular ROS levels in the brains of mice without treatment or 2 h post NC treatment were measured as follows. Briefly, dissected brains were homogenized in 0.01 M PBS (pH 7.2-7.4). To the homogenized tissue suspension (0.4 mg $mL^{-1}$), the cell permeable probe dihydroethidium (DHE, 5 μM) was added. After incubation for 30 min at 37° C. in the dark, fluorescence intensity of the suspension was measured using a plate reader at 530 nm as the excitation and 630 nm as the emission wavelength. The normalized data were expressed as a value relative to 100%. Results are shown in FIG. 19a.

Measurement of Pro-Inflammatory Cytokine IL-1β

The AD mouse brains were removed from mice at 24 h post NC treatment. The whole brain was homogenized in 1 mL of 1×RIPA buffer (1×, pH 8.0) per 40 mg of brain tissue. The homogenate was supplemented with 100 μL of 1× protease inhibitor mixture, and 200 μL each of 1× phosphatase inhibitor mixtures 1 and 2 (Sigma-Aldrich, CA) per 10 mL of ice-cold buffer and centrifuged at 14,000×g for 10 min. The supernatant was collected to measure IL-1β content by ELISA as per the manufacturer's protocol (Abcam, Toronto, ON, CA). Results are shown in 19b.

Preparation of Primary Cortical Neurons

The primary cultures of mouse cerebral cortical neurons were isolated from the cerebral cortex of day 15 (E15.5) old neonatal CD-1 mice, by a previously described method. [68] The 8 well plates were coated with laminin (Sigma-Aldrich, USA) and Poly-D-lysine (Cultrex® Poly-D-Lysine, Amsbio, USA) (1:20) for 1 h at 37° C. Then, the fresh brain tissues were dissociated in αMEM medium (Gibco, ThermoFisher Scientific, USA) for 15 min and the cells were plated in the neurobasal medium with 2% B-27 serum free supplement (Gibco™ B27™, ThermoFisher Scientific, USA), 1% penicillin-streptomycin-glutamine (Gibco, ThermoFisher Scientific, USA), 10% fetal bovine serum. Cells were cultured at 37° C. in a 95% air 5% $CO_2$ atmosphere.

Determination of In Vitro Cytotoxicity

The in vitro cytotoxicity to primary mouse cortical neurons of NCs was determined using the MTT assay [69]. For cytotoxicity experiments, 125,000 mouse primary cortical neuron cells in 200 μL of neurobasal medium with other supplements as mentioned in the previous section, were added into each well of an 8 well plate (Thermo Scientific Nunc 154534 Chamber Slide System, Glass, 8-Well, Thermo Fisher Scientific, CA). The cells were maintained for seven days in culture medium at 37° C. with 5% $CO_2$ atmosphere in which cell media was replaced every three days before treatment. Cells were subjected to different concentration of $H_2O_2$ for 6 h to determine the maximum non-toxic dose. From this experiment the $H_2O_2$ concentration of 50 μM was selected as the test dose for oxidative stress to primary cortical neurons. Similarly, an aAβ-BTRA-NC safe dose was determined by treating the cells with different concentrations (5, 15, 30 and 50 μM) of aAβ-BTRA-NC and 50 μM of $H_2O_2$ for up to 24 h. For the cell treatment with aAβ-BTRA-NC the stock solution (30 mM) was further diluted with neurobasal medium. After 24 h of treatment, cells were carefully washed twice with neurobasal medium, and cell viability was tested using a standard MTT assay. Briefly, after washing 100 μL of neurobasal medium containing MTT (1 mg $mL^{-1}$) was added and cells were incubated for another 4 h at 37° C. After 4 hr, 100 μL of 10% sodium dodecyl sulfate-HCl (10% SDS, 1 M HCl) was added in to each well, and plates were incubated at 37° C. overnight. The next day the absorbance of each well was recorded at 572 nm wavelength using a microplate reader SpectraMax plus 384 (Molecular Devices, Sunnyvale, CA). Finally, the cell viability was calculated using the following equation, $$\% \text{ cell ciability} = \frac{\text{Optical density of treatment}}{\text{Optical density of control}} \times 100$$

Investigation of the Effect of aAβ-BTRA-NCs on Reducing Oxidative Stress-Induced Damage to Neuronal Morphology in Vitro The primary cortical neurons were seeded at a density of 125,000 cells/well in 200 μL neurobasal medium as above in a glass bottom well of an 8-well plate and cultured for seven days at 37° C., 5% $CO_2$ as mentioned in the previous section. Cells were treated with 15 μM aAβ-BTRA-NC, 50 μM $H_2O_2$, and a combination of 15 μM aAβ-BTRA-NCs/50 μM $H_2O_2$ and incubated for 6 h at 37° C., 5% $CO_2$. At 5.75 h, 10 μL of 0.5 μg $mL^{-1}$ Hoechst 33342 and 2 μL of 50 μM calcein AM (Cedarlane, Canada) solution was added to the cells and incubated for 15 min. Cells were then washed three times with fresh media and replaced with 200 μL of fresh medium. Finally, cell uptake study was conducted with a confocal laser scanning microscope (Zeiss LSM 700 confocal microscope, Germany) with the filters for Hoechst 33342 for nucleus: $\lambda_{ex/em}$=360/447 nm, FITC for Calcein AM: $\lambda_{ex/em}$=490/525 nm.

Determination of Mn Content in the Brains and Relative Brain Delivery Efficiency The manganese (Mn) content in WT and Tg mouse brains at 2 h post injection of aAβ-BTRA-NCs (100 μmol Mn $kg^{-1}$ of bodyweight), or saline was quantified by ICP-AES using Optima 7300 DV ICP-AES, PerkinElmer Inc. The anesthetized animals were perfused with ice cold saline via the left ventricle and the whole mouse brains were collected, homogenized, and digested completely by $H_2O_2/HNO_3$ (1/2, v/v %) solution, then the solution was diluted using DDIW and filtered through a 0.22 μM filter (Millipore Ltd, CA) and the filtrate was collected for Mn quantification. The relative delivery efficiency of aAβ-BTRA-NCs into brain was calculated based on the followed formula.

$$\% \text{ Relative delivery efficiency} = \frac{(\text{Treatment} - \text{Control}) \text{ Mn/g of brain}}{\text{Total dosed Mn/g of tissues}} \times 100$$

Preliminary Assessment of Acute Organ Toxicity of aAβ-BTRA-NC

Figure 24:
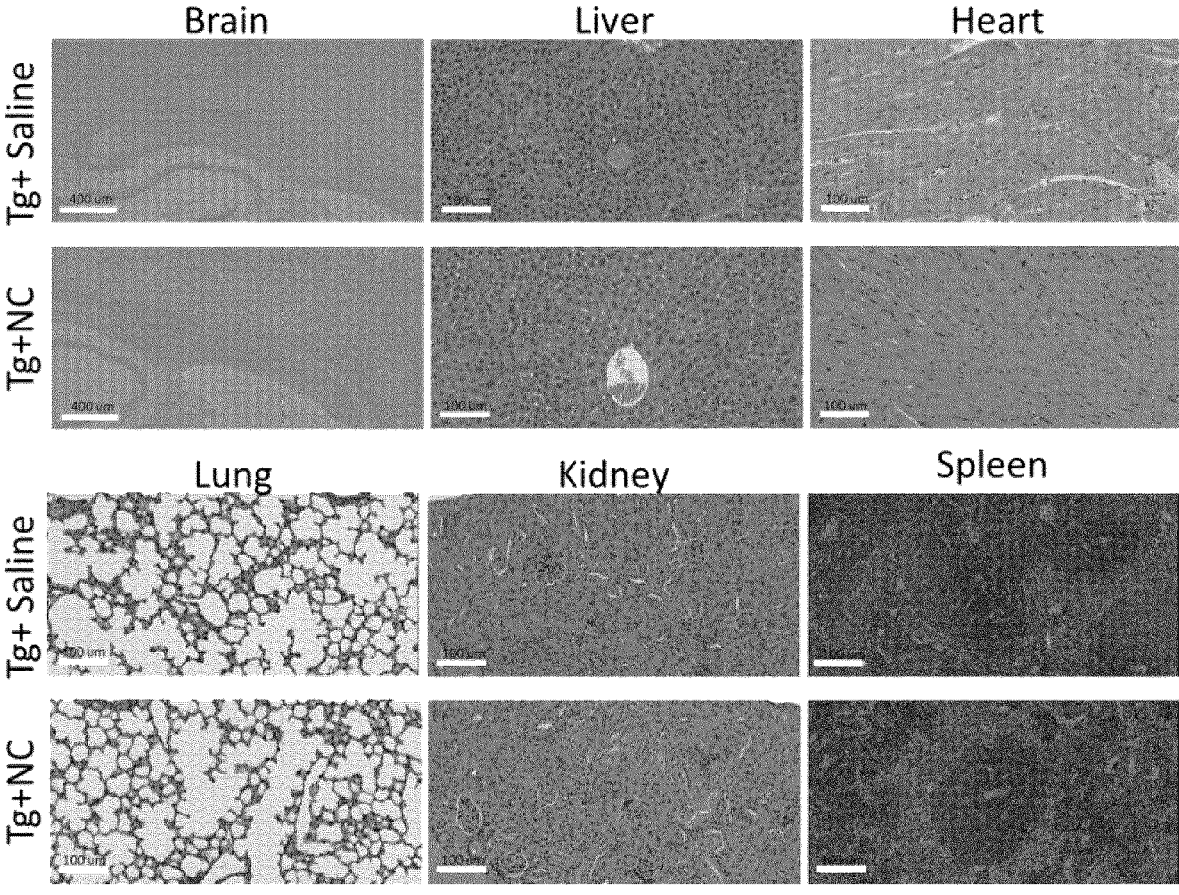
FIG. 24: shows representative Hematoxylin and eosin (H & E)-stained TgCRND8 mice (6-month age) tissue sections of various organs (brain, heart, kidneys, liver, lungs and spleen) resected at day 7 post i.v. injection of NCs (100 μmol Mn $kg^{-1}$ of bodyweight). Saline injected TgCRND8 mice were used as a control. All images were scanned at 20× magnification and the scale bars in the images are 100 μm.

To evaluate the possible acute toxicity of aAβ-BTRA-NC treatment on major organs, the investigated dose of NCs (100 μmol Mn $kg^{-1}$ of bodyweight) was intravenously administrated into 6-month old Tg mice. Seven days later the animals were sacrificed, and histological sections were prepared from brain, lungs, liver, kidneys, spleen, and heart tissues and stained with hematoxylineosin for morphological evaluation, which was conducted by a board-certified veterinary anatomic pathologist (FIG. 24).

Example 2

Synthesis and Characterization of GDNF-TPN 10 mg of ethyl arachidate and 15 mg of terpolymer were added to a 15 mL conical tube and heated to 45° C.

Pluronic® F-68 (PF68, 100 g/L, solvent: DDIW, 50 μL) solution, and 200 μL of PBS (pH=5.0) were added to the solution and stirred for 20 minutes. The mixture was sonicated for 10 minutes using a Hielscher UP 100H probe ultrasonicator (Ringwood, NJ, USA) at 80% peak. Following sonication, 100 μL of Human GDNF (15 mg/mL, solvent: PBS pH=5.0) was added into the emulsion and stirred for 20 mins at 45° C. Then the entire emulsion was quickly transferred onto ice to cool down and toped up to 1 mL using cold saline (0.9% w/v NaCl). The particle size and zeta potential of the NP were measured with Malvern Zetasizer Nano ZS (Worcestershire, UK). TEM images were acquired by a Hitachi H7000 electron microscope (Hitachi Canada, Ltd., Mississauga, ON, Canada) with an accelerating voltage of 75 kV. Immediately after formulation preparation, GDNF-NP suspension was diluted 4 times by PBS (pH=7.45), transferred to a centrifugal filter (MWCO=150 kDa), and centrifuged for 15 minutes at a RCF of 21,100×g. The free protein concentration in the filtrate was assayed using human GDNF Elisa kit under manufacture's protocol. The drug loading (% wt drug/wt lipid) was then calculated.

Figure 25:
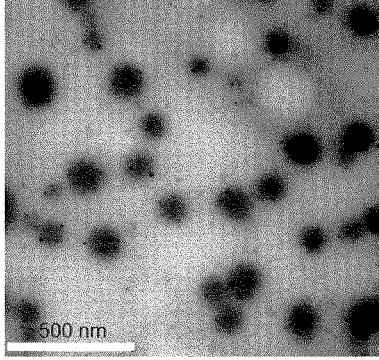
FIG. 25: shows the TEM images of GDNF-TPN.

As shown in Table 3 and FIG. 25, the resultant GDNF-TPN were ~110 nm in diameter, with polydispersity indices (PDI) of 0.23, zeta potentials of approximately −50 mV and GDNF loading content of 3.2 μg/mg TPN (Table 3). Transmission electron micrographs (TEM) portrayed GDNF-TPN in uniform spherical shape (FIG. 25).

TABLE 3

| characterization of GDNF-TPN includes size, PDI, Zeta potential and GDNF loading content. | | | |
|---|---|---|---|
| GDNF-TPN | 110.9 ± 3.5 | 0.23 ± 0.5 | −49.6 ± 1.3 | 3.2 μg/mg NP |

Determination of the Protein Release Kinetics from GDNF-TPN

Figure 26:
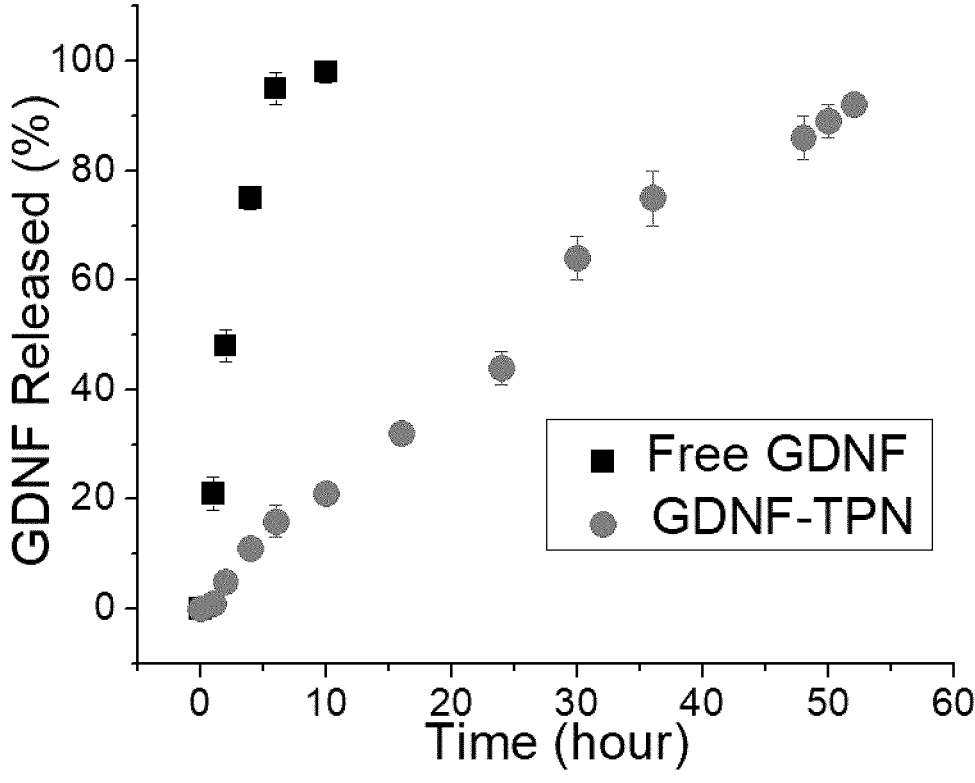
FIG. 26: shows the in vitro release profile of free GDNF and GDNF from the GDNF-TPN in the PBS (pH=7.4) at 37° C. determined by a dialysis method.

For measuring in vitro protein release kinetics, GDNF-NP suspension (1 mL) or free GDNF solution with the same drug concentration (1 mL) was enclosed in a 100 kDa MWCO dialysis tube and immersed in 200 mL, pH 7.45 PBS at 37° C. with continuous magnetic stirring. At selected time intervals, 200 μL of aqueous solution was withdrawn from the release medium and the protein concentration was measured with spectrophotometry. The same amount of fresh release medium was added into the release system after measurement. Each release experiment was repeated 3 times and the mean and standard deviations of triplicates are reported in FIG. 26.

Determination of the Stability of GDNF-TPN

Figure 27:
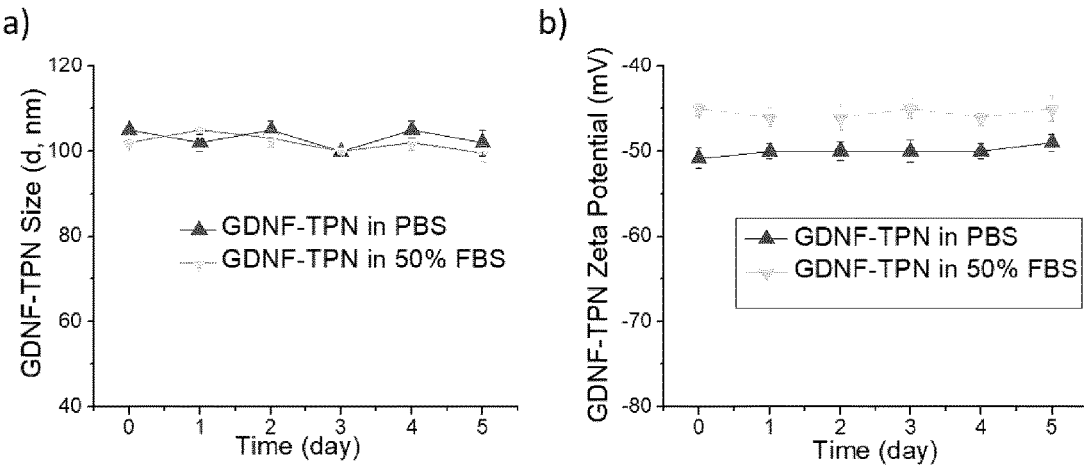
FIG. 27: shows the stability of GDNF-TPN at 37° C. in pH 7.4 PBS and 50% FBS. a) Nanoparticle size and b) nanoparticle zeta potential over a 5-day period.

To determine the stability of the GDNF-NP, 200 μL of NP were incubated in 2 mL of buffer (PBS, pH=7.4) or FBS at room temperature for 5 days. Samples were withdrawn at different time intervals and diluted with DDIW before the average particle size (FIG. 27a) and average zeta potential (FIG. 27b) measurements (Malvern Zetasizer Nano ZS, Worcestershire, UK). The GDNF-TPN were stable for over 5 days at 37° C. in 50% fetal bovine serum (FBS) and PBS buffer (FIG. 27a,b).

Determination of in Vitro Bioactivity of GDNF-TPN

Figure 28:
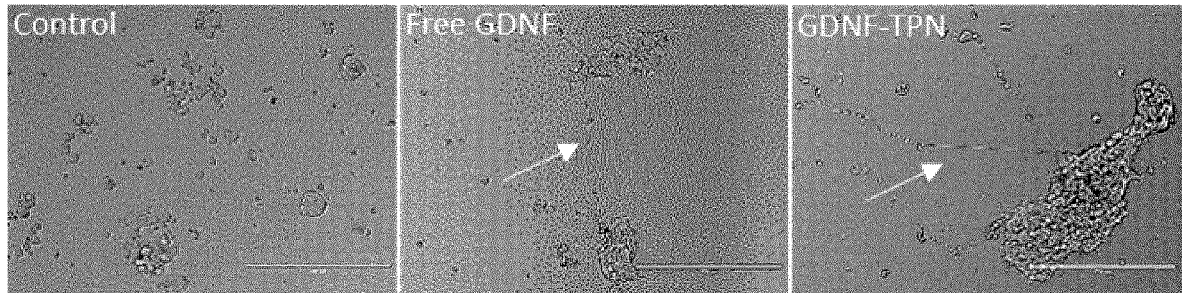
FIG. 28: shows the assessment of the biological activity of GDNF-TPN. Phase-contrast microscopy of PC-12 cells that were cultured for 7 days in medium (Control), and medium supplemented with free GDNF (Free GDNF, 200 ng/mL) or with GDNF-TPN at the same amount of GDNF (GDNF-TPN). Note the appearance of neurites both in free GDNF also in GDNF-TPN demonstrating the bioactivity of GDNF-TPN. Scar bar: 200 μm.

The differentiation of PC-12 cells was used to evaluate the bioactivity of GDNF-TPN. PC-12 cells were plated onto 12-well culture plate at a low density, 2×10³ cells/cm² in 1 ml of culture media. The culture medium was supplemented 24 h later with 200 ng/mL of free GDNF or the same concentration of GDNF-TPN. Neurite outgrowth was visualized after 7 days in culture under microscope. PC-12 cell neurite outgrowth indicated that GDNF was bioactive after the load into GDNF-TPN (FIG. 28). A similar effect was observed in cells treated with purified free GDNF (FIG. 28).

In Vivo Whole Body Biodistribution and Brain Accumulation of GDNF-TPN

Figure 29:
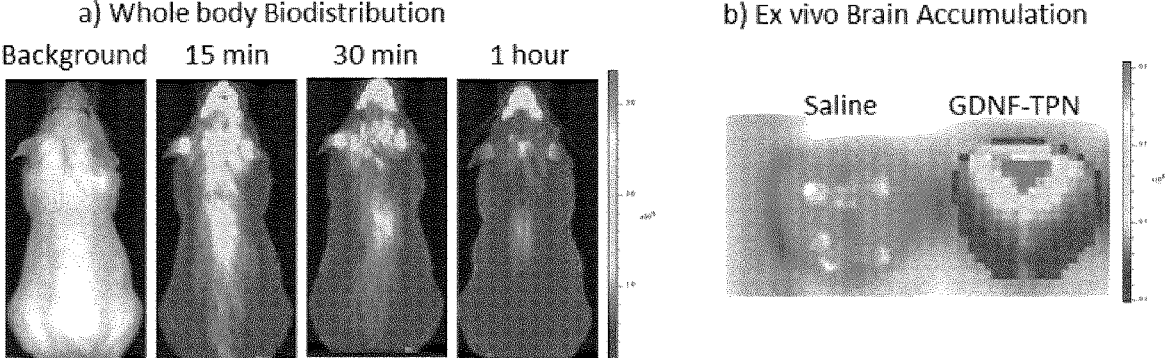
FIG. 29: shows the whole body biodistribution of NIR-labeled GDNF-TPN in Healthy CD-1 Mouse. a) Whole body images of live mice at various times up to 1 hours after the intravenously injection of NIR-labeled GDNF-TPN with the dose at GDNF 5 mg/kg, and b) Ex vivo image of fluorescence signals of NIR-labeled GDNF-TPN in the healthy brain region.

Near-infrared (NIR) dye HiLyte Fluor™ 750 (HF 750)-labeled GDNF-TPN were injected into the lateral tail vein of healthy CD-1 mice at the dose of 5 mg/kg. At pre-determined time points fluorescence images of the whole body and dissected brains were obtained using the Xenogen IVIS spectrum imager (745 nm excitation, and 820 nm emission wavelengths). As shown in the FIG. 29$a$, the accumulation of GDNF-TPN were detectable in the brain as early as 15 minutes post injection and remained for at least 1 hour. Immediate ex vivo fluorescent imaging of the dissected brain 1 hours after GDNF-TPN injection confirmed these results (FIG. 29$b$).

Pharmacokinetic Study of GDNF-TPN in Healthy CD-1 Mice

Figure 30:
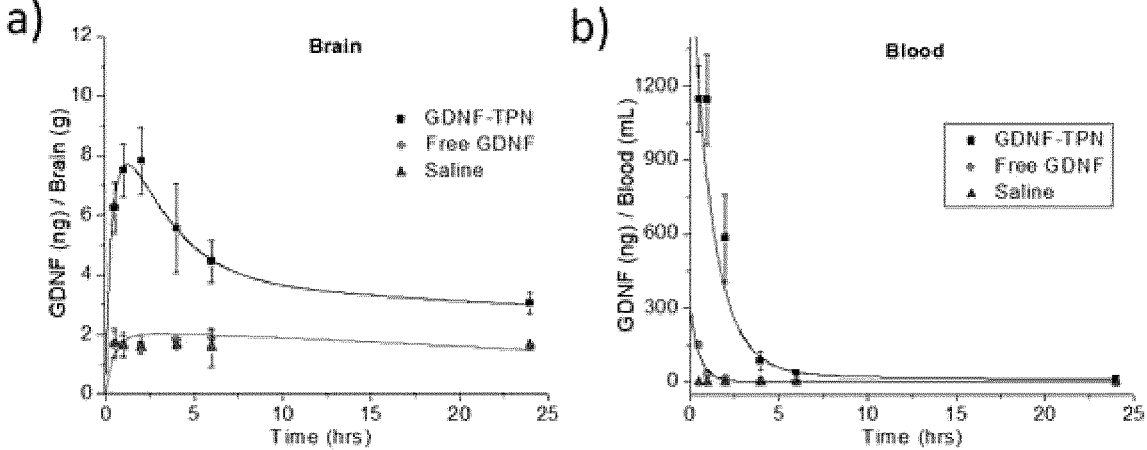
FIG. 30: shows the pharmacokinetics of GDNF-TPN and free GDNF in healthy brain and whole blood. Concentration profiles of GDNF in brain (a) and in blood (b) after i.v. injection of GDNF-TPN or free GDNF at the dose of 15 mg/kg (symbols are measured values, lines are fitted data).

Healthy CD-1 mice were randomly allocated into three treatment groups and received a single i. v. injection of GDNF-TPN, Free GDNF or saline at a matched dose of 15 mg GDNF/kg. At 0.5, 1, 2, 4, 6 and 24 hours after injection, whole blood was collected in heparinized tubes from ketamine anesthetized mice by cardiac puncture. Following perfusion with ice-cold saline via the left ventricle, the brains and organs were harvested, rinsed in PBS, weighted, snap-frozen and stored at −80° C. for further analysis. The mouse tissues were homogenized with RIPA buffer containing protease inhibitors and the GDNF was assayed using Human GDNF Elisa kit (Abcam, CA) under manufacture's protocol. Intravenous injection of GDNF-TPN to healthy mice with resulted in a 4-fold higher GDNF concentration in the healthy brain 15 minutes following treatment compared to treatment with an equivalent dose of free GDNF (FIG. 30$a$). A time course study in healthy mice further demonstrated that GDFN-TPN treatment resulted in markedly higher levels of GDNF in the brain and blood at all-time points tested as compared to treatment with free GDNF with a 2.6-fold increase in brain $AUC_{0-24h}$ (FIG. 30$a,b$ and Table 4) compared to free GDNF, indicating that GDNF-TPN enhanced drug delivery to healthy brain. Free GDNF was quickly eliminated from the blood within 2 hours after injection. In contrast, GDNF-TPN extended GDNF circulation time and significantly increased total drug exposure over time in the blood with a 2.7-fold increase in blood half-life, a 7.1-fold increase in blood $AUC_{0-24h}$, and 86% decrease in body clearance compared to free GDNF (Table 4).

TABLE 4

Fitted pharmacokinetic parameters to human GDNF ELISA kit quantification data for GDNF-TPN and free GDNF in whole blood and healthy brains after a single intravenous administration of 15 mg/kg GDNF (n = 3)

| | |
|---|---|
| 17.2 | 6.4 |
| 3377.1 | 472.8 |
| 88.8 | 634.4 |
| 105.1 | 41.2 |

Example 3

Synthesis and Characterization of Terpolymer-Lipid and FK506-TPN

Dodecylamine was conjugated to the terpolymer used the bellow method. Terpolymer (500 mg), EDC (80 mg) and NHS (80 mg) were dissolved into 5 mL of DDIW and allowed to react for 1 hour under stirring conditions. Dodecylamine (1 mL, 50 mg/mL solvent: DMSO) was added to the solution and was stirred at 50° C. for 24 hours. The final product solution was neutralized to pH 7.4 using NaOH and purified by dialysis (MWCO=12000 Da) against DMSO for 24 hours and DDIW for 48 hours. The dried terpolymer-lipid was obtained by lyophilizing the product for further use. To prepare the FK506-TPN, ethyl arachidate (6 mg) was added to a 15 mL of conical tube. The tube was heated in a circulating water bath at 80° C. until the lipid was melted. Pluronic® F-68 (PF68, 100 μL of 100 g/L in DDIW), FK506 (100 μL of 20 mg/mL in $CH_3CH_2OH$), and 200 μL of 50 mg/mL terpolymer-lipid in DDIW were added to the melted ethyl arachidate and the solution was stirred for 20 minutes. The solution was then ultrasonicated using a Hielscher UP 100H probe ultrasonicator at 80% peak amplitude with the probe tip submerged 5 mm in solution for 10 minutes. Following ultrasonication, the entire emulsion was quickly transferred into 1 mL of saline being stirred on ice. The particle size and zeta potential of NPs were measured using Malvern Zetasizer Nano ZS (Worcestershire, UK). The nanoparticles had an 84 nm of average diameter, 0.2 of PDI and −54.4 mV of zeta potential (Table 5). The drug loading content was obtained at 3.1%, based on the standard curve for FK506 at different concentration intervals by calculating UV-Vis spectrometer at 230 nm.

TABLE 5

Characterization of FK506-TPN and Z-DEVD-FMK peptide loaded nanoparticles (DEVD-TPN) includes size, PDI, Zeta potential and drugs loading content.

| Nanoparticles | Size (nm) | PDI | Zeta (mV) | Loading Content (%) |
|---|---|---|---|---|
| FK506-TPN | 84.0 ± 2.3 | 0.2 ± 0.4 | −54.4 ± 2.6 | 3.1 |
| DEVD-TPN | 53.7 ± 0.8 | 0.25 ± 0.6 | −25.6 ± 1.1 | 1.79 |

Determination of the FK506 Release Kinetics from FK506-TPN

Figure 31:
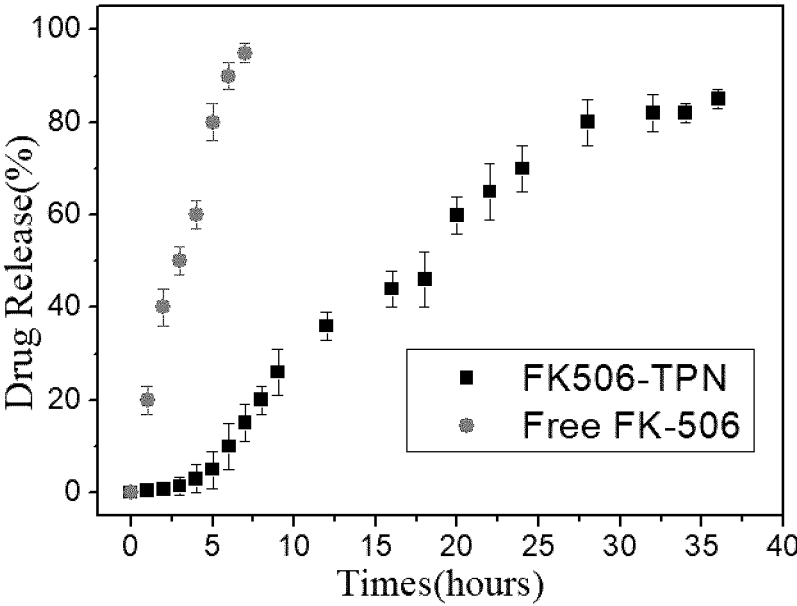
FIG. 31: shows the in vitro release profile of free FK506 and FK506 from the FK506-TPN in the PBS (pH=7.4) at 37° C. determined by a dialysis method.

FK506-TPN suspensions (1 mL) and free FK506 solutions of equivalent concentration was dialyzed against 100 mL of artificial CSF (0.5% wt %; SDS) using a 14 kDa MWCO membrane. The entire system was kept at 37° C. with continuous magnetic stirring. At selected time intervals, of aqueous solution (1 mL) was withdrawn from the release media and the absorbance spectrum was measured. The aliquot was returned to the release system after measurement. Each experiment was repeated 3 times and the mean±standard deviation is reported in FIG. 31.

Determination of FK506-TPN Attenuation against Cisplatin Induced Cytotoxicity Toward Different MEF Cells Heterozygous mouse embryonic fibroblasts (MEF) were maintained at 37° C. and 6% $CO_2$, in Dulbecco's Modified Eagle Medium (DMEM) containing 10% heat inactivated fetal bovine serum (FBS), 100 units penicillin, 100 μg streptomycin and 2.9 mg/ml glutamine (Invitrogen, 10378016). Primary MEF lineages were derived from E14.5 littermates, and only cells of passages <6 were utilized. MEF cells were exposed to either vehicle: 0.9% saline, blank nanoparticles, 75 μM cisplatin, 75 μM cisplatin+1 μM free FK506, or 75 μM cisplatin+1 μM FK506-TPN. They were chronically exposed for 24 hours before examining their viability by trypan blue exclusion. As shown in FIG. 355, the blank TPN did not induce cytotoxicity against MEF cells.

Figure 32:
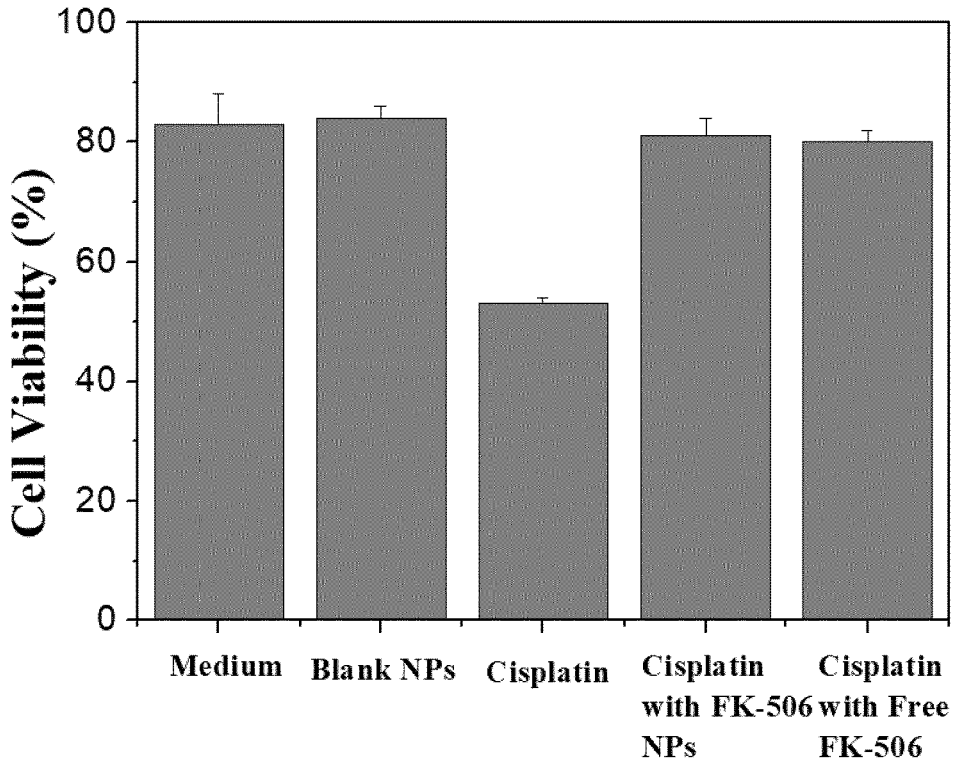
FIG. 32: shows the FK506-TPN attenuation of cisplatin induced cytotoxicity toward different heterozygous mouse embryonic fibroblasts (MEF) cells. (Medium: Saline; Cisplatin: 75 μM; FK506-TPN dose: 1 μM; Free FK506: 1 μM).

The FK506-TPN showed more than 37.5% of attenuation against the cisplatin induced cytotoxicity, similar to the free FK506 (FIG. 32).

In Vivo Whole Body Biodistribution and Brain Accumulation of FK506-TPN

Figure 33:
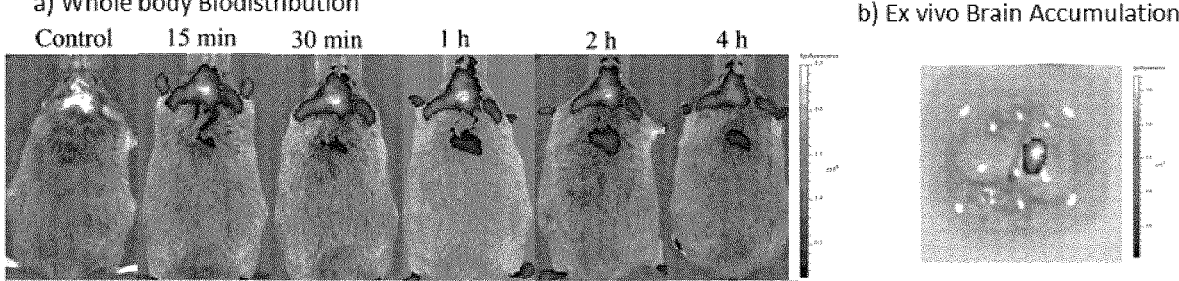
FIG. 33: shows the NIR-labeled FK506-TPN in vivo whole body biodistribution and ex vivo brain imaging of endothelin-1-induced stroke model in 129Sv/cp imj mice (1-year old). a) Whole body images of live mice at various times up to 4 hours after the intravenously injection of NIR-labeled FK506-TPN with the dose at FK506 17 mg/kg, and b) Ex vivo image of fluorescence signals of NIR-labeled FK506-TPN in the brain region.

Near-infrared (NIR) dye HiLyte Fluor™ 750 (HF 750)-labeled FK506-TPN were injected into the lateral tail vein of endothelin-1-induced stroke model in 129Sv/cp imj mice (1-year old) at the dose of 17 mg/kg. At pre-determined time points fluorescence images of the whole body and dissected brains were obtained using the Xenogen IVIS spectrum imager (745 nm excitation, and 820 nm emission wavelengths). As shown in the FIG. 33, the accumulation of FK506-TPN were detectable in the brain as early as 15 minutes post injection and remained in brain for at least 4 hours. Immediate ex vivo fluorescent imaging of the dissected brain 4 hours after FK506-TPN injection confirmed these results (FIG. 33).

Example 4

Synthesis and Characterization of Z-DEVD-FMK Peptide Loaded Nanoparticles (DEVD-TPN)

To prepare the self-assembled DEVD-TPN, terpolymer-lipid (10 mg) was dissolved in 2.0 ml of DDI water. The terpolymer-lipid solution was then placed in an ice bath, and while under ultrasonication, using a Hielscher UP100H probe ultrasonicator (Hielscher USA, Inc., Ringwood NJ, USA), of Peptide solution (1 mg/ml in $CH_3CN/H_2O$ (⅔, v/v) mixture) was added in 5 small increments (200 μL: 5×40 μL) to the terpolymer-lipid solution every 10 seconds. The ultrasonication continued for another 10 minutes and then size and zeta potential of NPs were tested using Malvern Zetasizer Nano ZS (Worcestershire, UK). As shown in Table 5, the prepared DEVD-TPN had a 53.7 nm of average diameter, 0.25 of PDI and −25.6 mV of zeta potential. The drug loading content was obtained at 1.9%, based on the standard curve for DEVD at different concentration intervals by calculating UV-Vis spectrometer at 200 nm.

Determination of the DEVD Release Kinetics from DEVD-TPN

Figure 34:
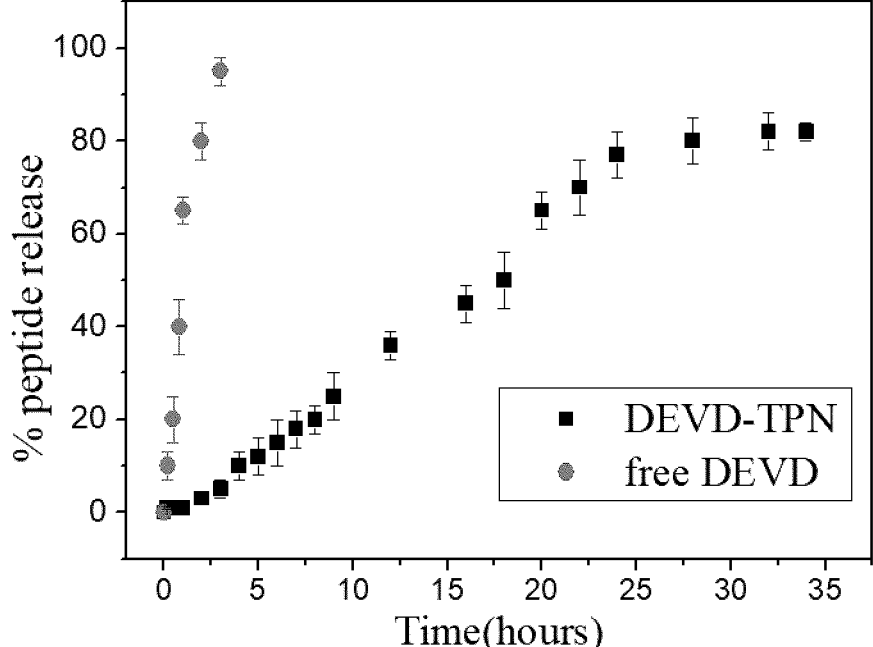
FIG. 34: shows the in vitro release profile of free Z-DEVD-FMK peptide (DEVD) and DEVD from the DEVD-TPN in the PBS (pH=7.4) at 37° C. determined by a dialysis method.

DEVD-TPN suspensions (1 mL) and free DEVD solutions of equivalent concentration was dialyzed against 100 mL of pH 7.45 PBS at 37° C. with continuous magnetic using a 14 kDa MWCO membrane. The entire system was kept at 37° C. with continuous magnetic stirring. At selected time intervals, of aqueous solution (0.5 mL) was withdrawn from the release media and the absorbance spectrum was measured. The aliquot was returned to the release system after measurement. Each experiment was repeated 3 times and the mean±standard deviation is reported in FIG. 34.

Figure 35:
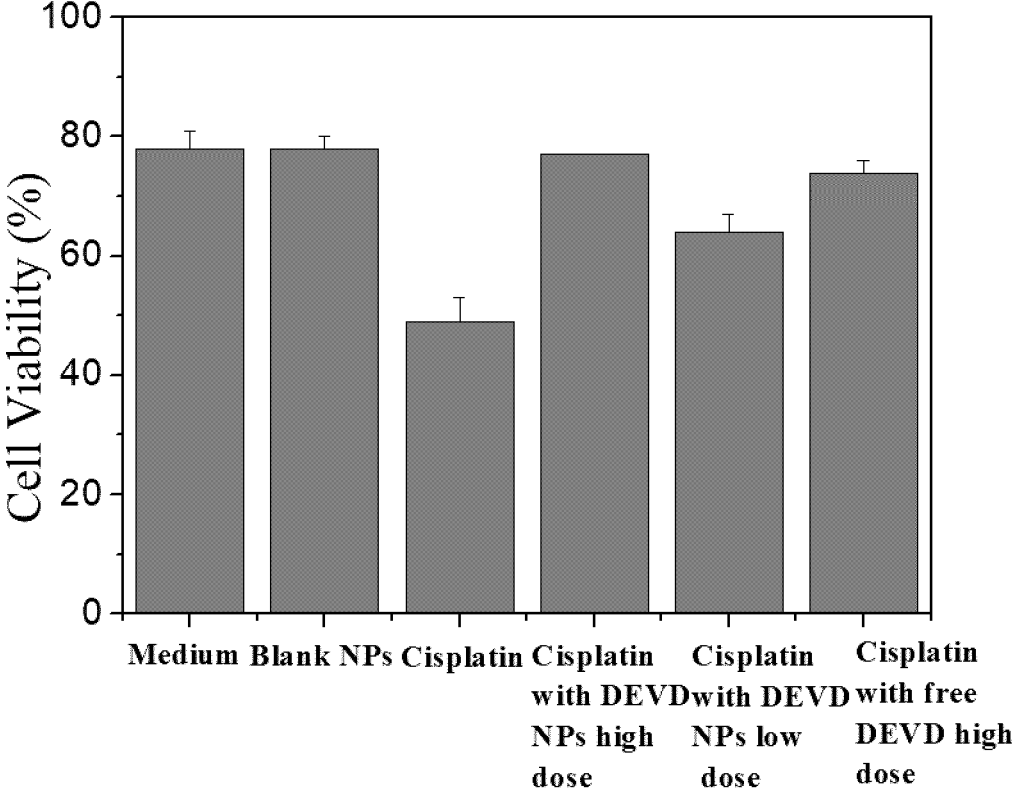
FIG. 35: shows the DEVD-TPN attenuation of cisplatin induced cytotoxicity toward different heterozygous mouse embryonic fibroblasts (MEF) cells. (Medium: Saline; Cisplatin: 75 μM; DEVD-TPN high dose: 75 μM; DEVD-TPN low dose: 25 μM, Free DEVD high dose: 75 μM).

Determination of DEVD-TPN Attenuation against Cisplatin Induced Cytotoxicity Toward Different MEF Cells Heterozygous mouse embryonic fibroblasts (MEF) were maintained at 37° C. and 6% $CO_2$, in Dulbecco's Modified Eagle Medium (DMEM) containing 10% heat inactivated fetal bovine serum (FBS), 100 units penicillin, 100 μg streptomycin and 2.9 mg/ml glutamine (Invitrogen, 10378016). Primary MEF lineages were derived from E14.5 littermates, and only cells of passages <6 were utilized. MEF cells were exposed to either vehicle: 0.9% saline, blank nanoparticles, 75 μM cisplatin, 75 μM cisplatin+75 μM free DEVD, 75 μM cisplatin+75 μM DEVD-TPN, or 75 μM cisplatin+25 μM DEVD-TPN. They were chronically exposed for 24 hours before examining their viability by trypan blue exclusion. The blank TPN did not induce cytotoxicity against MEF cells. The DEVD-TPN at higher dose showed more than 38.4% of attenuation against the cisplatin induced cytotoxicity, similar to the free DEVD (FIG. 35). Moreover, DEVD-TPN at 3 times lower dose showed more than 29.4% of attenuation against the cisplatin induced cytotoxicity.

Example 5

Synthesis and Characterization of Curcumin-TPN

Figure 36:
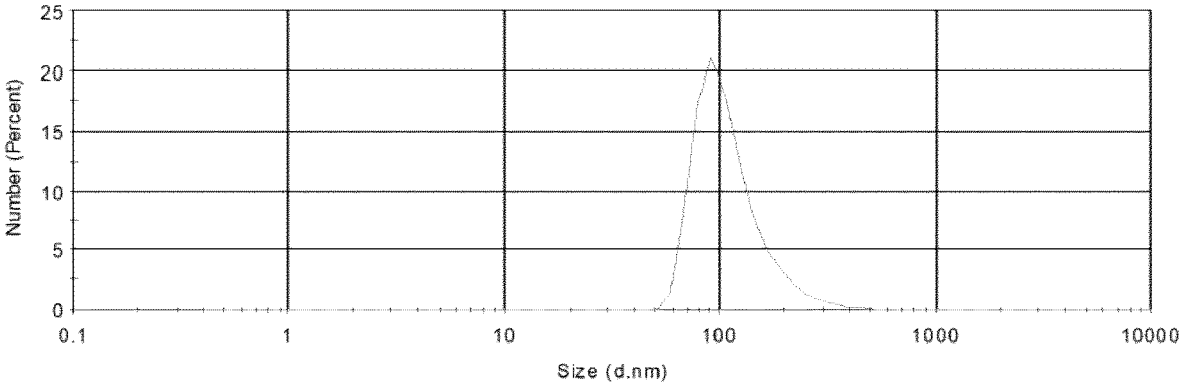
FIG. 36: shows the size distribution of curcumin-TPN.

To prepare the curcumin-TPN nanoparticles, 15 mg of ethyl arachidate was added to a 15 mL conical tube and heated to 65° C. until the lipid was melted. 100 μL of 100 g/L PF 68 solution, 100 μL of 5 mg/mL curcumin in $CHCl_3$, 200 μL of 40 mg/mL terpolymer-lipid solution was added and stirred for 20 min. The mixture was then ultrasonicated using a Hielscher UP 100H probe ultrasonicator at 80% peak amplitude and 5 mm probe depth in solution for 10 minutes. Finally, the emulsion was quickly transferred into 1 mL of saline being stirred on ice. The particle size of NP is measured using a Zetasizer Nano system (FIG. 36). The average nanoparticle size, PDI and zeta potential were measured to be D=112.7±0.9 nm, PDI=0.213 (data not shown), and ξ=−45.5±1.2 mV (data not shown), respectively. The drug loading content was obtained at 1.5%, based on the standard curve for curcumin at different concentration intervals by calculating UV-Vis spectrometer at 435 nm.

Determination of the Curcumin Release Kinetics from Curcumin-TPN

Figure 37:
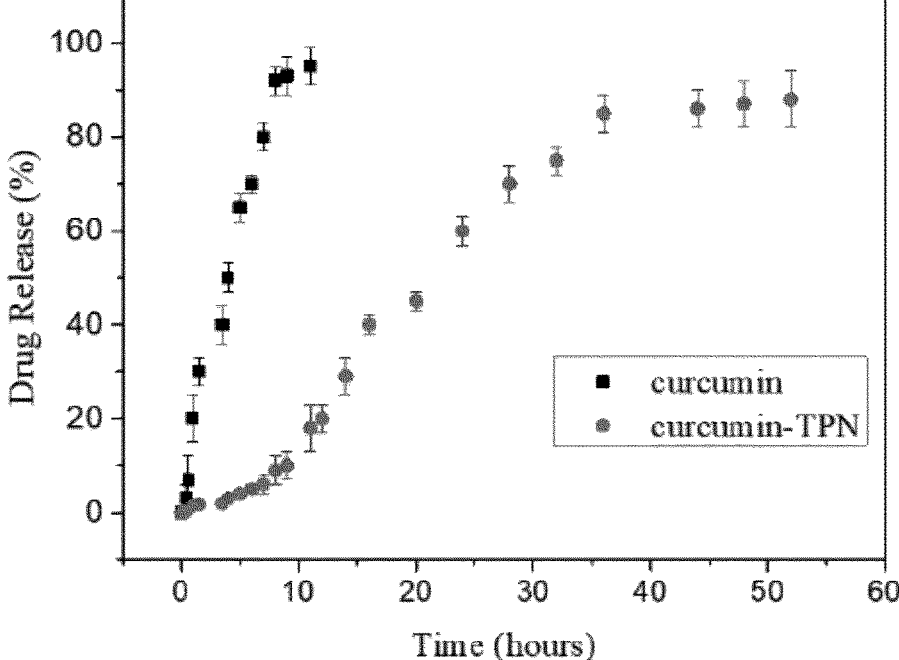
FIG. 37: shows the in vitro release profile of free curcumin and curcumin from the curcumin-TPN in the PBS (pH=7.4) at 37° C. determined by a dialysis method.

Drug-loaded nanoparticle suspensions (1 mL) or solutions containing free drug was dialyzed 200 mL of PBS (200 mL, pH=7.45, containing 0.5% SDS) using a 14 kDa MWCO membrane. The entire system was kept at 37° C. with continuous magnetic stirring. At selected time intervals, 1 mL of aqueous solution was withdrawn from the release media and the absorbance spectrum was measured, which was put back in the release system after measurement. Each experiment was repeated 3 times and the mean±standard deviation is reported in FIG. 37.

Example 6

Synthesis and Characterization of Multifunctional FK506-BTRA-NCs

The present invention discloses the synthesis of polymer-lipid nanoparticles that include or consist of both hydrophilic and hydrophobic domains to allow efficient loading of both hydrophilic and hydrophobic cargo materials in a single NC. The bioavailability hydrophobic drugs, such as FK506 is limited due to its poor solubility and low stability in aqueous media. The novel formulation is prepared by co-loading the precursor MDNPs and hydrophobic drug FK506 in a nanoparticle. First, precursor MDNPs are prepared using 1 mL of KMnO4 (25 mg/mL) in the presence of polyvinyl alcohol (PVA) at 41° C. In a separate vial phospholipid (phosphatidylcholine, 20 mg), FK506 (1 mg), and ethyl arachidate (4 mg) are dissolved in ethanol (5 mL) at 41° C. The ethanol-lipid-FK506 solution is then quickly injected in the MDNPs solution and mixed for 15 minutes to form the emulsion. Finally the 10 mL of BTP (1 mg/mL) is added and emulsion is processed through high pressure homogenizer (5 cycles) to obtain the stable FK506 and MDNPs loaded nano-suspension. The final nanoparticle solution is collected in 30 mL of ice cold double distilled water. The particle are washed and concentrated using the tangential flow filtration techniques and lyophilized using dextran as cryoprotectant. The particles are characterized using dynamic light scattering to obtain size distribution and zeta potential. ICP-AEOS is performed to determine the MDNPs content in nanoparticle formulation. The FK506 loading content was obtained be extracting the drug in ethanol using sonication to disrupt the particles and reading the UV-Vis spectrum at 230 nm. The drug calibration curve is used to determine the exact drug content. The in vitro efficacy of FK506-BTRA-NCs will be evaluated by bioassays using primary neurons and cell lines incubated under hypoxic or normoxic conditions.

Example 7

Synthesis and Characterization of Multifunctional DEVD-BTRA-NCs

The multifunctional formulation is prepared by loading both the hydrophilic MDNPs and Z-DEVD-FMK in nanoparticle formulation. To prepare this formulation first precursor MDNPs are synthesized using 1 mL of KMnO4 (25 mg/mL) as starting material and appropriate amount of polyvinyl alcohol (PVA) at 41° C. The reaction is monitored by measuring the UV-Vis spectrum at 325 nm to observe the complete conversion of $KMnO_4$ into MDNPs. Once the reaction is complete 200 µL of peptide solution (1 mg/ml in $CH_3CN/H_2O$ (⅖, v/v) mixture) is added, and solution is stirred for 5 minutes. In a separate vial phospholipid (phosphatidylcholine, 20 mg), and ethyl arachidate (4 mg) are dissolved in ethanol (5 mL) at 37-41° C. The ethanol-lipid solution is then quickly injected in the MDNPs+DEVD mixture and stirred for 15 minutes to form the pre-emulsion. Finally the 10 mL of BTP (1 mg/mL) is added and emulsion is processed through high pressure homogenizer (3 cycles) to obtain the stable DEVD and MDNPs loaded nanoparticles. The final nanoparticle solution is collected in 30 mL of ice cold double distilled water. Nano-suspension is washed and concentrated using the tangential flow filtration techniques. Multifunctional nanoparticles are finally lyophilized using dextran as cryoprotectant. The obtained particles are characterized using dynamic light scattering (DLS) to obtain size distribution and zeta potential. ICP-AEOS is performed to determine the Mn content in nanoparticle formulation. The DEVD loading content is obtained be extracting the drug in $CH_3CN/H_2O$ (⅖, v/v) mixture using sonication to disrupt the particles. The centrifuge filters are used to collect the drug. The drug loading content is measured by UV-Vis spectrophotometry. The drug calibration curve is used to determine the exact drug content in nanoparticle formulation. The in vitro efficacy of FK506-BTRA-NCs will be evaluated by bioassays using primary neurons and cell lines incubated under hypoxic or normoxic conditions.

Example 8

Synthesis and Characterization of RNA-BTRA-NCs

The nanoparticle based platform technology is synthesized under mild condition by keeping the industrial standard in place. Such carrier system is a potential candidate to deliver therapeutic biologics (RNAs) in combination with MDNPs. A siRNA, miRNA, long non-coding RNA, or modified RNA such as Gapmer antisense oligonucleotide is selected for targeting a specific mRNA associated with the disease. The RNA-BTRA-NCs can be synthesized with or without co-loading with MDNPs. To prepare the combined nanoparticle formulation, precursor MDNPs are first synthesized using 1 mL of KMnO4 (25 mg/mL) as starting material and appropriate amount of polyvinyl alcohol (PVA) at 37° C. The complete conversion of $KMnO_4$ to MDNPs is confirmed by measuring the UV-Vis spectrum at 325 nm and by XPS. Once the reaction is complete, 100 µL of aqueous solution of siRNA solution (4 nmole) is added, and solution is stirred for 5 minutes. In a separate vial phospholipid (phosphatidylcholine, 20 mg), and ethyl arachidate (4 mg) are dissolved in ethanol (5 mL) at 37° C. The ethanol-lipid solution is then quickly injected in the MDNPs+RNA mixture and stirred for 10 minutes to form the pre-emulsion. Finally the 10 mL of BTP (1 mg/mL) is added and solution is mixed for 10 minutes. Finally the emulsion is processed through high pressure homogenizer (3 cycles) to obtain the stable siRNA and MDNPs loaded nanoparticles. The final nanoparticle suspension is collected in 20 mL of ice cold double distilled water. Nano-suspension is washed and concentrated using the tangential flow filtration technique. Multifunctional nanoparticles are finally lyophilized using dextran as cryoprotectant. The RNA-nanoparticles without MDNPs are prepared similarly except no precursor MDNPs incorporated. The obtained particles are characterized using dynamic light scattering (DLS) to determine particle size distribution and zeta potential. ICP-AEOS is performed to determine the Mn content in the nanoparticles. The RNA loading content is obtained by reading the UV-Vis spectrum and gel electrophoresis. The efficiency of the nanoparticle delivered RNA will be assessed by RT-qPCR.

REFERENCES

[1] J. S. Lunn, S. A. Sakowski, J. Hur, E. L. Feldman, Stem cell technology for neurodegenerative diseases, Ann. Neurol., 70 (2011) 353-361.

[2] C. Soto, S. Pritzkow, Protein misfolding, aggregation, and conformational strains in neurodegenerative diseases, Nat. Neurosci., 21 (2018) 1332-1340.

[3] J. A. Bertout, S. A. Patel, M. C. Simon, The impact of O2 availability on human cancer, Nat. Rev. Cancer, 8 (2008) 967-975.

[4] J. W. Shim, J. R. Madsen, VEGF Signaling in Neurological Disorders, International journal of molecular sciences, 19 (2018) 275.

[5] K. Hu, S. Babapoor-Farrokhran, M. Rodrigues, M. Deshpande, B. Puchner, F. Kashiwabuchi, S. J. Hassan, L. Asnaghi, J. T. Handa, S. Merbs, C. G. Eberhart, G. L. Semenza, S. Montaner, A. Sodhi, Hypoxia-inducible factor 1 upregulation of both VEGF and ANGPTL4 is required to promote the angiogenic phenotype in uveal melanoma, Oncotarget, 7 (2016) 7816-7828.

[6] E. Storkebaum, P. Carmeliet, VEGF: a critical player in neurodegeneration, The Journal of clinical investigation, 113 (2004) 14-18.

[7] K. J. Barnham, C. L. Masters, A. I. Bush, Neurodegenerative diseases and oxidative stress, Nature reviews. Drug discovery, 3 (2004) 205-214.

[8] M. Schieber, N. S. Chandel, ROS function in redox signaling and oxidative stress, Curr. Biol., 24 (2014) R453-462.

[9] A. A. Dayem, H. Y. Choi, J. H. Kim, S. G. Cho, Role of oxidative stress in stem, cancer, and cancer stem cells, Cancers (Basel), 2 (2010) 859-884.

[10] F. Panza, M. Lozupone, G. Logroscino, B. P. Imbimbo, A critical appraisal of amyloid-beta-targeting therapies for Alzheimer disease, Nat. Rev. Neurol., 15 (2019) 73-88.

[11] D. G. Smith, R. Cappai, K. J. Barnham, The redox chemistry of the Alzheimer's disease amyloid beta peptide, Biochim. Biophys. Acta, 1768 (2007) 1976-1990.

[12] M. Rosini, E. Simoni, A. Milelli, A. Minarini, C. Melchiorre, Oxidative stress in Alzheimer's disease: are we connecting the dots?, J. Med. Chem., 57 (2014) 2821-2831.

[13] F. Zhang, R. Zhong, H. Qi, S. Li, C. Cheng, X. Liu, Y. Liu, W. Le, Impacts of Acute Hypoxia on Alzheimer's Disease-Like Pathologies in APP(swe)/PS1(dE9) Mice and Their Wild Type Littermates, Front. Neurosci., 12 (2018) 314-314.

[14] V. W. Chow, M. P. Mattson, P. C. Wong, M. Gleichman, An overview of APP processing enzymes and products, Neuromolecular Med., 12 (2010) 1-12.

[15] C. Kerridge, D. I. Kozlova, N. N. Nalivaeva, A. J. Turner, Hypoxia Affects Neprilysin Expression Through Caspase Activation and an APP Intracellular Domain-dependent Mechanism, Front. Neurosci., 9 (2015) 426-426.

[16] S. Varadarajan, S. Yatin, M. Aksenova, D. A. Butterfield, Review: Alzheimer's amyloid beta-peptide-associated free radical oxidative stress and neurotoxicity, J. Struct. Biol., 130 (2000) 184-208.

[17] T. Chitnis, H. L. Weiner, CNS inflammation and neurodegeneration, J. Clin. Invest., 127 (2017) 3577-3587.

[18] M. T. Heneka, M. J. Carson, J. El Khoury, G. E. Landreth, F. Brosseron, D. L. Feinstein, A. H. Jacobs, T. Wyss-Coray, J. Vitorica, R. M. Ransohoff, K. Herrup, S. A. Frautschy, B. Finsen, G. C. Brown, A. Verkhratsky, K. Yamanaka, J. Koistinaho, E. Latz, A. Halle, G. C. Petzold, T. Town, D. Morgan, M. L. Shinohara, V. H. Perry, C. Holmes, N. G. Bazan, D. J. Brooks, S. Hunot, B. Joseph, N. Deigendesch, O. Garaschuk, E. Boddeke, C. A. Dinarello, J. C. Breitner, G. M. Cole, D. T. Golenbock, M. P. Kummer, Neuroinflammation in Alzheimer's disease, Lancet Neurol., 14 (2015) 388-405.

[19] N. Pankratz, T. Foroud, Genetics of Parkinson disease, Genet. Med., 9 (2007) 801-811.

[20] A. R. Green, B. D. Mitchell, A. F. Tordoff, M. B. Youdim, Evidence for dopamine deamination by both type A and type B monoamine oxidase in rat brain in vivo and for the degree of inhibition of enzyme necessary for increased functional activity of dopamine and 5-hydroxytryptamine, Br. J. Pharmacol., 60 (1977) 343-349.

[21] T. Nagatsu, M. Sawada, Molecular mechanism of the relation of monoamine oxidase B and its inhibitors to Parkinson's disease: possible implications of glial cells, J. Neural Transm. Suppl., (2006) 53-65.

[22] H. L. Sun, B. L. Sun, D. W. Chen, Y. Chen, W. W. Li, M. Y. Xu, Y. Y. Shen, Z. Q. Xu, Y. J. Wang, X. L. Bu, Plasma α-synuclein levels are increased in patients with obstructive sleep apnea syndrome, Annals of Clinical and Translational Neurology, 6 (2019) 788-794.

[23] Q. Xu, H. Guo, X. Zhang, B. Tang, F. Cai, W. Zhou, W. Song, Hypoxia regulation of ATP13A2 (PARKS) gene transcription, J. Neurochem., 122 (2012) 251-259.

[24] F. Shephard, O. Greville-Heygate, S. Liddell, R. Emes, L. Chakrabarti, Analysis of Mitochondrial haemoglobin in Parkinson's disease brain, Mitochondrion, 29 (2016) 45-52.

[25] K. C. Arthur, A. Calvo, T. R. Price, J. T. Geiger, A. Chiò, B. J. Traynor, Projected increase in amyotrophic lateral sclerosis from 2015 to 2040, Nature communications, 7 (2016) 12408-12408.

[26] J. D. Rothstein, Current hypotheses for the underlying biology of amyotrophic lateral sclerosis, Ann. Neurol., 65 Suppl 1 (2009) S3-9.

[27] S. M. Kim, H. Kim, J. S. Lee, K. S. Park, G. S. Jeon, J. Shon, S. W. Ahn, S. H. Kim, K. M. Lee, J. J. Sung, K. W. Lee, Intermittent hypoxia can aggravate motor neuronal loss and cognitive dysfunction in ALS mice, PLoS One, 8 (2013) e81808-e81808.

[28] S. M. Kim, H. Kim, J. S. Lee, K. S. Park, G. S. Jeon, J. Shon, S. W. Ahn, S. H. Kim, K. M. Lee, J. J. Sung, K. W. Lee, Intermittent hypoxia can aggravate motor neuronal loss and cognitive dysfunction in ALS mice, PLoS One, 8 (2013) e81808.

[29] F. O. Walker, Huntington's disease, The Lancet, 369 (2007) 218-228.

[30] T. Velusamy, A. S. Panneerselvam, M. Purushottam, M. Anusuyadevi, P. K. Pal, S. Jain, M. M. Essa, G. J. Guillemin, M. Kandasamy, Protective Effect of Antioxidants on Neuronal Dysfunction and Plasticity in Huntington's Disease, Oxid. Med. Cell. Longev., 2017 (2017) 3279061.

[31] U. Bayani, V. S. Ajay, Z. Paolo, R. T. Mahajan, Oxidative Stress and Neurodegenerative Diseases: A Review of Upstream and Downstream Antioxidant Therapeutic Options, Curr. Neuropharmacol., 7 (2009) 65-74.

[32] R. Rodrigo, R. Fernández-Gajardo, R. Gutiérrez, J. M. Matamala, R. Carrasco, A. Miranda-Merchak, W. Feuerhake, Oxidative stress and pathophysiology of ischemic stroke: novel therapeutic opportunities, CNS Neurol. Disord. Drug Targets, 12 (2013) 698-714.

[33] C. Saraiva, C. Praça, R. Ferreira, T. Santos, L. Ferreira, L. Bernardino, Nanoparticle-mediated brain drug delivery: Overcoming blood-brain barrier to treat neurodegenerative diseases, J. Control. Release, 235 (2016) 34-47.

[34] W. Li, S. Yang, Targeting oxidative stress for the treatment of ischemic stroke: Upstream and downstream therapeutic strategies, Brain circulation, 2 (2016) 153-163.

[35] C. L. Allen, U. Bayraktutan, Oxidative stress and its role in the pathogenesis of ischaemic stroke, Int. J. Stroke, 4 (2009) 461-470.

[36] F. Lupoli, T. Vannocci, G. Longo, N. Niccolai, A. Pastore, The role of oxidative stress in Friedreich's ataxia, FEBS Lett., 592 (2018) 718-727.

[37] J. Tamarit, E. Obis, J. Ros, Oxidative stress and altered lipid metabolism in Friedreich ataxia, Free Radic. Biol. Med., 100 (2016) 138-146.

[38] Y. J. Yu, R. J. Watts, Developing therapeutic antibodies for neurodegenerative disease, Neurotherapeutics: the journal of the American Society for Experimental NeuroTherapeutics, 10 (2013) 459-472.

[39] A. Compston, A. Coles, Multiple sclerosis, The Lancet, 372 (2008) 1502-1517.

[40] X. M. Wang, B. Walitt, L. Saligan, A. F. Tiwari, C. W. Cheung, Z. J. Zhang, Chemobrain: a critical review and causal hypothesis of link between cytokines and epigenetic reprogramming associated with chemotherapy, Cytokine, 72 (2015) 86-96.

[41] J. Zhao, H. Zuo, K. Ding, X. Zhang, Z. Bi, H. Cheng, Changes in plasma IL-1β, TNF-α and IL-4 levels are involved in chemotherapy-related cognitive impairment in early-stage breast cancer patients, American journal of translational research, 12 (2020) 3046-3056.

[42] R. W. Paterson, R. L. Brown, L. Benjamin, R. Nortley, S. Wiethoff, T. Bharucha, D. L. Jayaseelan, G. Kumar, R. E. Raftopoulos, L. Zambreanu, V. Vivekanandam, A. Khoo, R. Geraldes, K. Chinthapalli, E. Boyd, H. Tuzlali, G. Price, G. Christofi, J. Morrow, P. McNamara, B. McLoughlin, S. T. Lim, P. R. Mehta, V. Levee, S. Keddie, W. Yong, S. A. Trip, A. J. M. Foulkes, G. Hotton, T. D. Miller, A. D. Everitt, C. Carswell, N. W. S. Davies, M. Yoong, D. Attwell, J. Sreedharan, E. Silber, J. M. Schott, A. Chandratheva, R. J. Perry, R. Simister, A. Checkley, N. Longley, S. F. Farmer, F. Carletti, C. Houlihan, M. Thom, M. P. Lunn, J. Spillane, R. Howard, A. Vincent, D. J. Werring, C. Hoskote, H. R. Jäger, H. Manji, M. S. Zandi, The emerging spectrum of COVID-19 neurology: clinical, radiological and laboratory findings, Brain, (2020).

[43] M. A. Ellul, L. Benjamin, B. Singh, S. Lant, B. D. Michael, A. Easton, R. Kneen, S. Defres, J. Sejvar, T. Solomon, Neurological associations of COVID-19, Lancet Neurol., 19 (2020) 767-783.

[44] P. Mehta, D. F. McAuley, M. Brown, E. Sanchez, R. S. Tattersall, J. J. Manson, COVID-19: consider cytokine storm syndromes and immunosuppression, Lancet, 395 (2020) 1033-1034.

[45] S. G. Schütz, J. Robinson-Papp, HIV-related neuropathy: current perspectives, HIV AIDS (Auckl.), 5 (2013) 243-251.

[46] L. Al-Harthi, E. Campbell, J. A. Schneider, D. A. Bennett, What HIV in the Brain Can Teach Us About SARS-CoV-2 Neurological Complications?, AIDS Res. Hum. Retroviruses, (2020).

[47] J. Lee, S. Giordano, J. H. Zhang, Autophagy, mitochondria and oxidative stress: cross-talk and redox signalling, Biochem. J., 441 (2012) 523-540.

[48] A. Kaus, D. Sareen, ALS Patient Stem Cells for Unveiling Disease Signatures of Motoneuron Susceptibility: Perspectives on the Deadly Mitochondria, ER Stress and Calcium Triad, Front. Cell. Neurosci., 9 (2015).

[49] D. P. Gelain, G. Antonio Behr, R. Birnfeld de Oliveira, M. Trujillo, Antioxidant therapies for neurodegenerative diseases: mechanisms, current trends, and perspectives, Oxid. Med. Cell. Longev., 2012 (2012) 895153-895153.

[50] H. Fritz, D. Kennedy, D. Fergusson, R. Fernandes, S. Doucette, K. Cooley, A. Seely, S. Sagar, R. Wong, D. Seely, Vitamin A and retinoid derivatives for lung cancer: a systematic review and meta analysis, PLoS One, 6 (2011) e21107.

[51] H. L. Wong, X. Y. Wu, R. Bendayan, Nanotechnological advances for the delivery of CNS therapeutics, Adv Drug Deliv Rev, 64 (2012) 686-700.

[52] D. Mehta, R. Jackson, G. Paul, J. Shi, M. Sabbagh, Why do trials for Alzheimer's disease drugs keep failing? A discontinued drug perspective for 2010-2015, Expert Opin. Investig. Drugs, 26 (2017) 735-739.

[53] K. Blennow, H. Zetterberg, The Past and the Future of Alzheimer's Disease Fluid Biomarkers, J. Alzheimers Dis., 62 (2018) 1125-1140.

[54] G. B. Frisoni, M. Boccardi, F. Barkhof, K. Blennow, S. Cappa, K. Chiotis, J. F. Démonet, V. Garibotto, P. Giannakopoulos, A. Gietl, O. Hansson, K. Herholz, C. R. Jack, Jr., F. Nobili, A. Nordberg, H. M. Snyder, M. Ten Kate, A. Varrone, E. Albanese, S. Becker, P. Bossuyt, M. C. Carrillo, C. Cerami, B. Dubois, V. Gallo, E. Giacobini, G. Gold, S. Hurst, A. Lönneborg, K. O. Lovblad, N. Mattsson, J. L. Molinuevo, A. U. Monsch, U. Mosimann, A. Padovani, A. Picco, C. Porteri, O. Ratib, L. Saint-Aubert, C. Scerri, P. Scheltens, J. M. Schott, I. Sonni, S. Teipel, P. Vineis, P. J. Visser, Y. Yasui, B. Winblad, Strategic roadmap for an early diagnosis of Alzheimer's disease based on biomarkers, Lancet Neurol., 16 (2017) 661-676.

[55] K. A. Johnson, N. C. Fox, R. A. Sperling, W. E. Klunk, Brain imaging in Alzheimer disease, Cold Spring Harb. Perspect. Med., 2 (2012) a006213.

[56] K. L. Viola, J. Sbarboro, R. Sureka, M. De, M. A. Bicca, J. Wang, S. Vasavada, S. Satpathy, S. Wu, H. Joshi, P. T. Velasco, K. MacRenaris, E. A. Waters, C. Lu, J. Phan, P. Lacor, P. Prasad, V. P. Dravid, W. L. Klein, Towards non-invasive diagnostic imaging of early-stage Alzheimer's disease, Nat Nano, 10 (2015) 91-98.

[57] H. Rusinek, S. De Santi, D. Frid, W. H. Tsui, C. Y. Tarshish, A. Convit, M. J. de Leon, Regional brain atrophy rate predicts future cognitive decline: 6-year longitudinal MR imaging study of normal aging, Radiology, 229 (2003) 691-696.

[58] A. Weller, J. L. Barber, Ø. E. Olsen, Gadolinium and nephrogenic systemic fibrosis: an update, Pediatr. Nephrol., 29 (2014) 1927-1937.

[59] J. A. Rees, G. J. Deblonde, D. D. An, C. Ansoborlo, S. S. Gauny, R. J. Abergel, Evaluating the potential of chelation therapy to prevent and treat gadolinium deposition from MRI contrast agents, Sci. Rep., 8 (2018) 4419.

[60] W. A. Banks, From blood-brain barrier to blood-brain interface: new opportunities for CNS drug delivery, Nat Rev Drug Discov, 15 (2016) 275-292.

[61] Y. Su, P. T. Chang, Acidic pH promotes the formation of toxic fibrils from beta-amyloid peptide, Brain Res., 893 (2001) 287-291.

[62] D. Pan, S. D. Caruthers, A. Senpan, A. H. Schmieder, S. A. Wickline, G. M. Lanza, Revisiting an old friend: manganese-based MRI contrast agents, Wiley Interdiscip Rev Nanomed Nanobiotechnol, 3 (2011) 162-173.

[63] M. A. Chishti, D. S. Yang, C. Janus, A. L. Phinney, P. Horne, J. Pearson, R. Strome, N. Zuker, J. Loukides, J. French, S. Turner, G. Lozza, M. Grilli, S. Kunicki, C. Morissette, J. Paquette, F. Gervais, C. Bergeron, P. E. Fraser, G. A. Carlson, P. S. George-Hyslop, D. Westaway, Early-onset amyloid deposition and cognitive deficits in transgenic mice expressing a double mutant form of amyloid precursor protein 695, J. Biol. Chem., 276 (2001) 21562-21570.

[64] C. R. Gordijo, A. Z. Abbasi, M. A. Amini, H. Y. Lip, A. Maeda, P. Cai, P. J. O'Brien, R. S. DaCosta, A. M. Rauth, X. Y. Wu, Design of Hybrid $MnO_2$-Polymer-Lipid Nanoparticles with Tunable Oxygen Generation Rates and Tumor Accumulation for Cancer Treatment, Adv. Func. Mater 25 (2015) 1858-1872.

[65] L. M. Shaw, M. Korecka, C. M. Clark, V. M. Lee, J. Q. Trojanowski, Biomarkers of neurodegeneration for diagnosis and monitoring therapeutics, Nat. Rev. Drug Discov., 6 (2007) 295-303.

[66] X. Feng, A. Chen, Y. Zhang, J. Wang, L. Shao, L. Wei, Central nervous system toxicity of metallic nanoparticles, Int J Nanomedicine, 10 (2015) 4321-4340.

[67] Y. Tanaka, Y. Tanaka, T. Furuta, Y. Yanagawa, T. Kaneko, The effects of cutting solutions on the viability of GABAergic interneurons in cerebral cortical slices of adult mice, J. Neurosci. Methods, 171 (2008) 118-125.

[68] C. Sciarretta, L. Minichiello, The preparation of primary cortical neuron cultures and a practical application using immunofluorescent cytochemistry, Methods Mol. Biol., 633 (2010) 221-231.

[69] A. Singhal, V. B. Morris, V. Labhasetwar, A. Ghorpade, Nanoparticle-mediated catalase delivery protects human neurons from oxidative stress, Cell Death Dis., 4 (2013) e903.

What is claimed is:

1. A theranostic nanoparticle for detecting a central nervous system (CNS) disease area behind the blood-brain barrier (BBB) and reducing reactive oxygen species (ROS) and oxidative stress in the CNS disease area, the theranostic nanoparticle comprising a metal oxide nanoparticle wherein the metal oxide acts both as (i) a contrast agent that reacts with hydrogen peroxide to produce paramagnetic ions that improve magnetic resonance imagining contrast and (ii) a therapeutic agent that reduces ROS and oxidative stress in the CNS disease area, the metal oxide nanoparticle being embedded in a matrix of lipids and a brain targeted polymer (BTP) that facilitates crossing the BBB and binds to the paramagnetic ions, and a functional moiety conjugated onto the BTP that binds to and/or complexes to a biomarker of the CNS disease thereby facilitating BBB penetration and accumulation of the theranostic nanoparticle in the disease area of the CNS, wherein the theranostic nanoparticle has a negative surface charge.

2. The theranostic nanoparticle of claim 1, wherein the biomarker of the CNS disease is a pathological biomarker of a neurodegenerative disease or stroke.

3. The theranostic nanoparticle of claim 2, wherein the neurodegenerative disease is one or more of Alzheimer disease (AD), Parkinson disease (PD), Huntington's disease (HD), Amyotrophic Lateral Sclerosis (ALS), Friedreich's ataxia (FRDA) and Multiple sclerosis (MS), viral or bacterial neuroinflammation and chemobrain.

4. The theranostic nanoparticle of claim 1, wherein the functional moiety is an antibody, a targeting moiety, a neurotrophic factor, a peptide, a nucleic acid, a small molecule modifiers of programmed cell death (PCD), a detectable moiety, a labeling agent, an imaging agent or mixtures thereof.

5. The theranostic nanoparticle of claim 1, wherein the theranostic nanoparticle is formulated with a pharmaceutically acceptable vehicle suitable for intravenous injection.

6. The theranostic nanoparticle of claim 1, wherein the functional moiety is an anti-amyloid $\beta$-42 antibody (aA$\beta$).

7. The theranostic nanoparticle of claim 1, wherein the theranostic nanoparticle further includes a therapeutic agent embedded into the matrix of lipids and BTP.

8. The theranostic nanoparticle of claim 7, wherein the therapeutic agent includes one or more of a nucleic acid, a peptide, a therapeutic antibody, a small molecule modifiers of programmed cell death (PCD), a neurotrophic factor, a growth factor, an immunosuppressive agent, an anti-inflammatory agent, an anti-apoptotic agent, a cytokine inhibitor, a metabolism modulator, a vascular modulator, and/or a cell proliferation inhibitor.

9. The theranostic nanoparticle of claim 7, wherein the therapeutic agent is one or more of tacrolimus (FK506), N-benzyloxycarbonyl-Asp (OMe)-Glu (OMe)-Val-Asp (OMe)-fluoromethylketone (Z-DEVD-FMK), curcumin, glial cell line-derived neurotrophic factor (GDNF), brain-derived neurotrophic factor (BDNF), neurotrophin, cerebral dopamine neurotrophic factor, mesencephalic or astrocyte-derived neurotrophic factor.

10. The theranostic nanoparticle of claim 1, wherein the theranostic nanoparticle has a particle size between about 40 nm and about 160 nm.

11. The theranostic nanoparticle of claim 1, wherein the theranostic nanoparticle is stabilized by a positively charged polyelectrolyte.

12. The theranostic nanoparticle of claim 1, wherein the metal oxide is $MnO_2$.

13. A method of preparing theranostic nanoparticles for detecting a central nervous system (CNS) disease area behind the blood-brain barrier (BBB) and reducing ROS and oxidative stress in the CNS disease area, the method comprising of steps of (a) coating metal oxide nanoparticles with a lipid or a polymer to obtain hydrophobic or hydrophilic nanoparticle surface, the metal oxide being reactive with hydrogen peroxide to produce paramagnetic ions that improve magnetic resonance imaging contrast; (b) mixing the coated metal oxide nanoparticles and a brain targeted polymer in a lipid matrix to form an emulsion, wherein the brain targeted polymer binds to the paramagnetic ions, and (c) ultrasonicating or high pressure homogenizing the emulsion to form the theranostic nanoparticles having a negative surface charge.

14. The method of claim 13, wherein the metal oxide nanoparticles are $KMnO_4$ nanoparticles, and the method further comprises mixing the $KMnO_4$ nanoparticles with a positively charged polyelectrolyte to obtain stabilized $MnO_4$ nanoparticles (MD NPs).

15. The method of claim 14, wherein the method comprises mixing the MD NPs with lipids to form an emulsion in which the MD NPs are coated with the lipids, coating the emulsion with a terpolymer, and homogenizing the emulsion coated with the terpolymer to obtain a homogeneous nanoparticle emulsion.

16. The method of claim 13, wherein the brain targeted polymer is an antibody to target a site in the central nervous system behind a blood-brain barrier.

17. The method of claim 13, wherein the brain targeted polymer is anti-amyloid $\beta$ (AB) antibody, GDNF, FK506, Z-DEVD-FMK or curcumin.

18. A method of treating and diagnosing ("theranostics") a central nervous system (CNS) disease or condition in a subject in need comprising, administering to the subject an effective amount of the theranostic nanoparticle of claim 1, wherein the biomarker of the CNS disease or condition is a pathological biomarker of a neurodegenerative disease or stroke, the metal oxide in the theranostic nanoparticle treating the subject by reducing ROS and oxidative stress in the CNS disease area, and detecting the produced paramagnetic ions in the CNS disease area using magnetic resonance imaging (MRI) and using said MRI images to diagnose the subject.

19. The method of claim 18, wherein the method comprises reducing hypoxia in the disease area by producing oxygen in the disease area.

20. A magnetic resonance (MR) contrast agent for a CNS disease-affected area, wherein the MR contrast agent comprises the theranostic nanoparticle of claim 1.

21. A method for acquiring an image of a subject using a magnetic resonance imaging (MRI) comprising: (a) administering to the subject an image enhancing amount of the theranostic nanoparticle of claim 12, (b) obtaining an MRI image of the subject in diseased regions where the MD NP react with ROS ($H_2O_2$) producing paramagnetic $Mn^{2+}$ ions that enhance the MRI contrast.

22. The theranostic nanoparticle of claim 1, wherein the BTP comprises poly(methacrylic acid) and polysorbate 80.

23. The method of claim 13, wherein the BTP comprises poly(methacrylic acid) and polysorbate 80.

* * * * *